(12) United States Patent
Torrens-Jover et al.

(10) Patent No.: US 10,071,968 B2
(45) Date of Patent: Sep. 11, 2018

(54) METHYL-1H-PYRAZOLE ALKYLAMINE COMPOUNDS HAVING MULTIMODAL ACTIVITY AGAINST PAIN

(71) Applicant: LABORATORIOS DEL DR. ESTEVE S.A., Barcelona (ES)

(72) Inventors: Antoni Torrens-Jover, Terrassa (ES); Josep Mas-Prio, Barcelona (ES); Carmen Almansa-Rosales, Barcelona (ES); Monica Garcia-Lopez, Barcelona (ES)

(73) Assignee: ESTEVE PHARMACEUTICALS S.A., Barcelona (ES)

( * ) Notice: Subject to any disclaimer, the term of this patent is extended or adjusted under 35 U.S.C. 154(b) by 0 days.

(21) Appl. No.: 15/531,810

(22) PCT Filed: Dec. 15, 2015

(86) PCT No.: PCT/EP2015/002526
§ 371 (c)(1),
(2) Date: May 31, 2017

(87) PCT Pub. No.: WO2016/096127
PCT Pub. Date: Jun. 23, 2016

(65) Prior Publication Data
US 2017/0305862 A1    Oct. 26, 2017

(30) Foreign Application Priority Data

Dec. 15, 2014 (EP) .................................... 14382516

(51) Int. Cl.
| | | |
|---|---|---|
| C07D 231/12 | (2006.01) |
| C07D 401/06 | (2006.01) |
| C07D 409/06 | (2006.01) |
| C07D 417/06 | (2006.01) |
| C07D 401/12 | (2006.01) |

(52) U.S. Cl.
CPC .......... C07D 231/12 (2013.01); C07D 401/12 (2013.01); C07D 409/06 (2013.01); C07D 417/06 (2013.01)

(58) Field of Classification Search
CPC .. C07D 231/12; C07D 401/06; C07D 409/06; C07D 417/06
See application file for complete search history.

(56) References Cited

U.S. PATENT DOCUMENTS

2002/0188017 A1    12/2002    Merce-Vidal

FOREIGN PATENT DOCUMENTS

| EP | 1642577 | 4/2006 |
| EP | 2395003 | 12/2011 |
| FR | 2681322 A1 * | 3/1993 |
| GB | 2435826 | 9/2007 |
| GB | 2435826 A * | 9/2007 |

OTHER PUBLICATIONS

An English translation of FR-2681322-A1, 1993.*
Dickenson, A.H., et al. European Journal of Pain, vol. 9, No. 2, p. 113-116, Apr. 1, 2005.
International Search Report for PCT/EP2015/002526 dated Feb. 10, 2016.

* cited by examiner

*Primary Examiner* — Laura L. Stockton
(74) *Attorney, Agent, or Firm* — Hueschen and Sage

(57) ABSTRACT

The present invention relates to compounds having dual pharmacological activity towards both the sigma (σ) receptor, and the μ-opiod receptor and more particularly to methyl-1H-pyrazole alkylamine compounds having this pharmacological activity, to processes of preparation of such compounds, to pharmaceutical compositions comprising them, and to their use in therapy, in particular for the treatment of pain.

11 Claims, No Drawings

METHYL-1H-PYRAZOLE ALKYLAMINE COMPOUNDS HAVING MULTIMODAL ACTIVITY AGAINST PAIN

FIELD OF THE INVENTION

The present invention relates to compounds having dual pharmacological activity towards both the sigma (σ) receptor, and the μ-opiod receptor (MOR or mu-opioid receptor) and more particularly to methyl-1H-pyrazole alkylamine derivatives having this pharmacological activity, to processes of preparation of such compounds, to pharmaceutical compositions comprising them, and to their use in therapy, in particular for the treatment of pain.

BACKGROUND OF THE INVENTION

The adequate management of pain constitutes an important challenge, since currently available treatments provide in many cases only modest improvements, leaving many patients unrelieved [Turk D C, Wilson H D, Cahana A. Treatment of chronic non-cancer pain. *Lancet* 377, 2226-2235 (2011)]. Pain affects a big portion of the population with an estimated prevalence of around 20% and its incidence, particularly in the case of chronic pain, is increasing due to the population ageing. Additionally, pain is clearly related to comorbidities, such as depression, anxiety and insomnia, which lead to important productivity losses and socio-economical burden [Goldberg D S, McGee S J. Pain as a global public health priority. *BMC Public Health.* 11, 770 (2011)]. Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

As mentioned before, there are few available therapeutic classes for the treatment of pain, and opioids are among the most effective, especially when addressing severe pain states. They act through three different types of opioid receptors (mu, kappa and gamma) which are transmembrane G-protein coupled receptors (GPCRs). Still, the main analgesic action is attributed to the activation of the μ-opioid receptor (MOR). However, the general administration of MOR agonists is limited due to their important side effects, such as constipation, respiratory depression, tolerance, emesis and physical dependence [Meldrum, M. L. (Ed.). Opioids and Pain Relief: A Historical Perspective. Progress in Pain Research and Management, Vol 25. IASP Press, Seattle, 2003]. Additionally, MOR agonists are not optimal for the treatment of chronic pain as indicated by the diminished effectiveness of morphine against chronic pain conditions. This is especially proven for the chronic pain conditions of neuropathic or inflammatory origin, in comparison to its high potency against acute pain. The finding that chronic pain can lead to MOR down-regulation may offer a molecular basis for the relative lack of efficacy of morphine in long-term treatment settings [Dickenson, A. H., Suzuki, R. Opioids in neuropathic pain: Clues from animal studies. *Eur J Pain* 9, 113-6 (2005)]. Moreover, prolonged treatment with morphine may result in tolerance to its analgesic effects, most likely due to treatment-induced MOR down-regulation, internalization and other regulatory mechanisms. As a consequence, long-term treatment can result in substantial increases in dosing in order to maintain a clinically satisfactory pain relief, but the narrow therapeutic window of MOR agonists finally results in unacceptable side effects and poor patient compliance.

The sigma-1 ($\sigma_1$) receptor was discovered 35 years ago and initially assigned to a new subtype of the opioid family, but later on and based on the studies of the enantiomers of SKF-10,047, its independent nature was established. The first link of the $\sigma_1$ receptor to analgesia was established by Chien and Pasternak [Chien C C, Pasternak G W. Sigma antagonists potentiate opioid analgesia in rats. *Neurosci. Lett.* 190, 137-9 (1995)], who described it as an endogenous anti-opioid system, based on the finding that $\sigma_1$ receptor agonists counteracted opioid receptor mediated analgesia, while $\sigma_1$ receptor antagonists, such as haloperidol, potentiated it.

Many additional preclinical evidences have indicated a clear role of the $\sigma_1$ receptor in the treatment of pain [Zamanillo D, Romero L, Merlos M, Vela J M. Sigma 1 receptor: A new therapeutic target for pain. *Eur. J. Pharmacol,* 716, 78-93 (2013)]. The development of the $\sigma_1$ receptor knockout mice, which show no obvious phenotype and perceive normally sensory stimuli, was a key milestone in this endeavour. In physiological conditions the responses of the $\sigma_1$ receptor knockout mice to mechanical and thermal stimuli were found to be undistinguishable from WT ones but they were shown to possess a much higher resistance to develop pain behaviours than WT mice when hypersensitivity entered into play. Hence, in the $\sigma_1$ receptor knockout mice capsaicin did not induce mechanical hypersensitivity, both phases of formalin-induced pain were reduced, and cold and mechanical hypersensitivity were strongly attenuated after partial sciatic nerve ligation or after treatment with paclitaxel, which are models of neuropathic pain. Many of these actions were confirmed by the use of $\sigma_1$ receptor antagonists and led to the advancement of one compound, S1RA, into clinical trials for the treatment of different pain states. Compound S1RA exerted a substantial reduction of neuropathic pain and anhedonic state following nerve injury (i.e., neuropathic pain conditions) and, as demonstrated in an operant self-administration model, the nerve-injured mice, but not sham-operated mice, acquired the operant responding to obtain it (presumably to get pain relief), indicating that $\sigma_1$ receptor antagonism relieves neuropathic pain and also address some of the comorbidities (i.e., anhedonia, a core symptom in depression) related to pain states.

Pain is multimodal in nature, since in nearly all pain states several mediators, signaling pathways and molecular mechanisms are implicated. Consequently, monomodal therapies fail to provide complete pain relief. Currently, combining existing therapies is a common clinical practice and many efforts are directed to assess the best combination of available drugs in clinical studies [Mao J, Gold M S, Backonja M. Combination drug therapy for chronic pain: a call for more clinical studies. *J. Pain* 12, 157-166 (2011)]. Hence, there is an urgent need for innovative therapeutics to address this unmet medical need.

As mentioned previously, opioids are among the most potent analgesics but they are also responsible for various adverse effects which seriously limit their use.

Accordingly, there is still a need to find compounds that have an alternative or improved pharmacological activity in the treatment of pain, being both effective and showing the desired selectivity, and having good "drugability" properties, i.e. good pharmaceutical properties related to administration, distribution, metabolism and excretion.

Thus, the technical problem can therefore be formulated as finding compounds that have an alternative or improved pharmacological activity in the treatment of pain.

In view of the existing results of the currently available therapies and clinical practices, the present invention offers a solution by combining in a single compound binding to two different receptors relevant for the treatment of pain. This was mainly achieved by providing the compounds according to the invention that bind both to the μ-opiod receptor and to the σ$_1$ receptor.

SUMMARY OF THE INVENTION

In this invention a family of structurally distinct methyl-1H-pyrazole alkylamine derivatives which have a dual pharmacological activity towards both the sigma (σ) receptor, and the μ-opiod receptor was identified thus solving the above problem of identifying alternative or improved pain treatments by offering such dual compounds.

The invention is in one aspect directed to a compound having a dual activity binding to the σ$_1$ receptor and the μ-opioid receptor for use in the treatment of pain.

As this invention is aimed at providing a compound or a chemically related series of compounds which act as dual ligands of the σ$_1$ receptor and the μ-opioid receptor it is a very preferred embodiment if the compound has a binding expressed as K$_i$ which is preferably <1000 nM for both receptors, more preferably <500 nM, even more preferably <100 nM.

The invention is directed in a main aspect to a compound of general Formula (I),

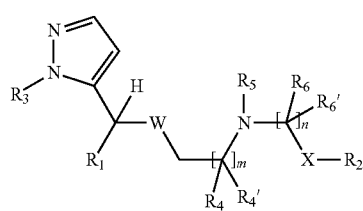

wherein R$_1$, R$_2$, R$_3$, R$_4$, R$_4$', R$_5$, R$_6$, R$_6$', W, X, m and n are as defined below in the detailed description.

DETAILED DESCRIPTION OF THE INVENTION

The invention is directed to a family of structurally distinct methyl-1H-pyrazole alkylamine derivatives which have a dual pharmacological activity towards both the sigma (σ) receptor and the μ-opiod receptor, thus solving the above problem of identifying alternative or improved pain treatments by offering such dual compounds.

The invention is in one aspect directed to a compound having a dual activity binding to the σ$_1$ receptor and the μ-opioid receptor for use in the treatment of pain.

As this invention is aimed at providing a compound or a chemically related series of compounds which act as dual ligands of the σ$_1$ receptor and the μ-opioid receptor it is a preferred embodiment if the compound has a binding expressed as K$_i$ which is preferably <1000 nM for both receptors, more preferably <500 nM, even more preferably <100 nM.

The applicant has surprisingly found that the problem on which the present invention is based can be solved by using a multimodal balanced analgesic approach combining two different synergistic activities in a single drug (i.e., dual ligands which are bifunctional and bind to μ-opioid receptor and to σ$_1$ receptor), thereby enhancing the opioid analgesia through the σ$_1$ activation without increasing the undesirable side effects. This supports the therapeutic value of a dual MOR/σ$_1$ receptor compound whereby the σ$_1$ receptor binding component acts as an intrinsic adjuvant of the MOR binding component.

This solution offered the advantage that the two mechanisms complement each other in order to treat pain and chronic pain using lower and better tolerated doses needed based on the potentiation of analgesia but avoiding the adverse events of μ-opioid receptor agonists.

A dual compound that possess binding to both the μ-opiod receptor and to the σ$_1$ receptor shows a highly valuable therapeutic potential by achieving an outstanding analgesia (enhanced in respect to the potency of the opioid component alone) with a reduced side-effect profile (safety margin increased compared to that of the opioid component alone) versus existing opioid therapies.

Advantageously, the dual compounds according to the present invention would in addition show one or more the following functionalities: σ$_1$ receptor antagonism and μ-opioid receptor agonism. It has to be noted, though, that both functionalities "antagonism" and "agonism" are also subdivided in their effect into subfunctionalities like partial agonism or inverse agonism. Accordingly, the functionalities of the dual compound should be considered within a relatively broad bandwidth.

An antagonist on one of the named receptors blocks or dampens agonist-mediated responses. Known subfunctionalities are neutral antagonists or inverse agonists.

An agonist on one of the named receptors increases the activity of the receptor above its basal level. Known subfunctionalities are full agonists, or partial agonists.

In addition, the two mechanisms complement each other since MOR agonists are only marginally effective in the treatment of neuropathic pain, while σ$_1$ receptor antagonists show outstanding effects in preclinical neuropathic pain models. Thus, the σ$_1$ receptor component adds unique analgesic actions in opioid-resistant pain. Finally, the dual approach has clear advantages over MOR agonists in the treatment of chronic pain as lower and better tolerated doses would be needed based on the potentiation of analgesia but not of the adverse events of MOR agonists.

A further advantage of using designed multiple ligands is a lower risk of drug-drug interactions compared to cocktails or multi-component drugs, thus involving simpler pharmacokinetics and less variability among patients. Additionally, this approach may improve patient compliance and broaden the therapeutic application in relation to monomechanistic drugs, by addressing more complex aetiologies. It is also seen as a way of improving the R&D output obtained using the "one drug-one target" approach, which has been questioned over the last years [Bornot A, Bauer U, Brown A, Firth M, Hellawell C, Engkvist O. Systematic Exploration of Dual-Acting Modulators from a Combined Medicinal Chemistry and Biology Perspective. *J. Med. Chem*, 56, 1197-1210 (2013)].

In a particular aspect, the present invention is directed to compounds of general Formula (I):

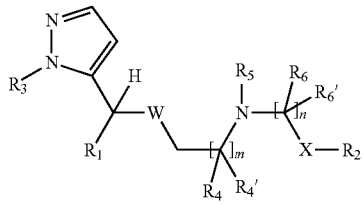

wherein
n is 1, 2, 3, 4, 5 or 6;
m is 1 or 2;
W is —O—, —NR$_w$—, —S— or —S(O)—;
X is selected from a bond, and —CR$_x$R$_{x'}$;
R$_1$ is substituted or unsubstituted cycloalkyl, substituted or unsubstituted aryl, or substituted or unsubstituted heterocyclyl;
R$_2$ is substituted or unsubstituted cycloalkyl, substituted or unsubstituted aryl, or substituted or unsubstituted heterocyclyl;
R$_3$ is hydrogen, or substituted or unsubstituted C$_{1-6}$ alkyl, substituted or unsubstituted C$_{2-6}$ alkenyl, or substituted or unsubstituted C$_{2-6}$ alkynyl;
R$_4$ and R$_{4'}$ are independently selected from hydrogen, unsubstituted C$_{1-6}$ alkyl, unsubstituted C$_{2-6}$ alkenyl, and unsubstituted C$_{2-6}$ alkynyl;
R$_5$ is selected from hydrogen, substituted or unsubstituted C$_{1-6}$ alkyl, substituted or unsubstituted C$_{2-6}$ alkenyl, and substituted or unsubstituted C$_{2-6}$ alkynyl;
R$_6$ and R$_{6'}$ are independently selected from hydrogen, substituted or unsubstituted C$_{1-6}$ alkyl, substituted or unsubstituted C$_{2-6}$ alkenyl, substituted or unsubstituted C$_{2-6}$ alkynyl, —C(O)OR$_{10}$ and —C(O)NR$_{10}$R$_{10'}$;
    wherein R$_{10}$ and R$_{10'}$ are independently selected from hydrogen, unsubstituted C$_{1-6}$ alkyl, unsubstituted C$_{2-6}$ alkenyl and unsubstituted C$_{2-6}$ alkynyl;
R$_x$ is selected from hydrogen, halogen, —OR$_{11}$, substituted or unsubstituted C$_{1-6}$ alkyl, substituted or unsubstituted C$_{2-6}$ alkenyl, substituted or unsubstituted C$_{2-6}$ alkynyl, —C(O)OR$_{11}$, —C(O)NR$_{11}$R$_{11'}$, —NR$_{11}$C(O)R$_{11'}$, and —NR$_{11}$R$_{11'''}$;
R$_{x'}$ is selected from hydrogen, substituted or unsubstituted C$_{1-6}$ alkyl, substituted or unsubstituted C$_{2-6}$ alkenyl and substituted or unsubstituted C$_{2-6}$ alkynyl;
    wherein R$_{11}$, R$_{11'}$ and R$_{11''}$ are independently selected from hydrogen, unsubstituted C$_{1-6}$ alkyl, unsubstituted C$_{2-6}$ alkenyl, unsubstituted C$_{2-6}$ alkynyl, and unsubstituted acetyl;
    and wherein R$_{11'''}$ is selected from hydrogen, unsubstituted C$_{1-6}$ alkyl, unsubstituted C$_{2-6}$ alkenyl, unsubstituted C$_{2-6}$ alkynyl and -Boc;
R$_w$ is selected from hydrogen, substituted or unsubstituted C$_{1-6}$ alkyl, substituted or unsubstituted C$_{2-6}$ alkenyl, substituted or unsubstituted C$_{2-6}$ alkynyl, —C(O)R$_{12}$, —C(O)OR$_{12}$, and —C(O)NR$_{12}$R$_{12'}$;
    wherein R$_{12}$ and R$_{12'}$ are independently selected from hydrogen, unsubstituted C$_{1-6}$ alkyl, unsubstituted C$_{2-6}$ alkenyl and unsubstituted C$_{2-6}$ alkynyl.

These compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a particular embodiment the following compound is excluded:

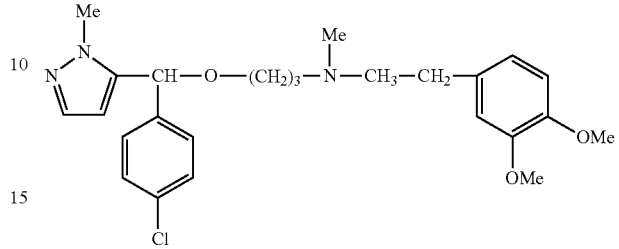

In the context of this invention, alkyl is understood as meaning saturated, linear or branched hydrocarbons, which may be unsubstituted or substituted once or several times. It encompasses e.g. —CH$_3$ and —CH$_2$—CH$_3$. In these radicals, C$_{1-2}$-alkyl represents C1- or C2-alkyl, C$_{1-3}$-alkyl represents C1-, C2- or C3-alkyl, C$_{1-4}$-alkyl represents C1-, C2-, C3- or C4-alkyl, C$_{1-5}$-alkyl represents C1-, C2-, C3-, C4-, or C5-alkyl, C$_{1-6}$-alkyl represents C1-, C2-, C3-, C4-, C5- or C6-alkyl, C$_{1-7}$-alkyl represents C1-, C2-, C3-, C4-, C5-, C6- or C7-alkyl, C$_{1-8}$-alkyl represents C1-, C2-, C3-, C4-, C5-, C6-, C7- or C8-alkyl, C$_{1-10}$-alkyl represents C1-, C2-, C3-, C4-, C5-, C6-, C7-, C8-, C9- or C10-alkyl and C$_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also CHF$_2$, CF$_3$ or CH$_2$OH etc. Preferably alkyl is understood in the context of this invention as C$_{1-8}$alkyl like methyl, ethyl, propyl, butyl, pentyl, hexyl, heptyl, or octyl; preferably is C$_{1-6}$alkyl like methyl, ethyl, propyl, butyl, pentyl, or hexyl; more preferably is C$_{1-4}$alkyl like methyl, ethyl, propyl or butyl.

Alkenyl is understood as meaning unsaturated, linear or branched hydrocarbons, which may be unsubstituted or substituted once or several times. It encompasses groups like e.g. —CH=CH—CH$_3$. The alkenyl radicals are preferably vinyl (ethenyl), allyl (2-propenyl). Preferably in the context of this invention alkenyl is C$_{2-10}$-alkenyl or C$_{2-8}$-alkenyl like ethylene, propylene, butylene, pentylene, hexylene, heptylene or octylene; or is C$_{2-6}$-alkenyl like ethylene, propylene, butylene, pentylene, or hexylene; or is C$_{2-4}$-alkenyl, like ethylene, propylene, or butylenes.

Alkynyl is understood as meaning unsaturated, linear or branched hydrocarbons, which may be unsubstituted or substituted once or several times. It encompasses groups like e.g. —C≡C—CH$_3$ (1-propinyl). Preferably alkynyl in the context of this invention is C$_{2-10}$-alkynyl or C$_{2-8}$-alkynyl like ethyne, propyne, butyene, pentyne, hexyne, heptyne, or octyne; or is C$_{2-6}$-alkynyl like ethyne, propyne, butyene, pentyne, or hexyne; or is C$_{2-4}$-alkynyl like ethyne, propyne, butyene, pentyne, or hexyne.

In the context of this invention cycloalkyl is understood as meaning saturated and unsaturated (but not aromatic) cyclic hydrocarbons (without a heteroatom in the ring), which can be unsubstituted or once or several times substituted. Furthermore, C$_{3-4}$-cycloalkyl represents C3- or C4-cycloalkyl, C$_{3-5}$-cycloalkyl represents C3-, C4- or C5-cycloalkyl, C$_{3-6}$- cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-6}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantyl. Preferably in the context of this invention cycloalkyl is $C_{3-8}$cycloalkyl like cyclopropyl, cyclobutyl, cyclopentyl, cyclohexyl, cycloheptyl, or cyclooctyl; or is $C_{3-7}$cycloalkyl like cyclopropyl, cyclobutyl, cyclopentyl, cyclohexyl, or cycloheptyl; or is $C_{3-6}$cycloalkyl like cyclopropyl, cyclobutyl, cyclopentyl or cyclohexyl, especially cyclopentyl or cyclohexyl.

In connection with alkyl (also in alkylaryl, alkylheterocyclyl or alkylcycloalkyl), alkenyl, alkynyl and O-alkyl—unless defined otherwise—the term substituted in the context of this invention is understood as meaning replacement of at least one hydrogen radical on a carbon atom by halogen (F, Cl, Br, I), $-NR_cR_{c'''}$, $-SR_c$, $-S(O)R_c$, $-S(O)_2R_c$, $-OR_c$, $-C(O)OR_c$, $-CN$, $-C(O)NR_cR_{c'}$, haloalkyl, haloalkoxy or $-OC_{1-4}$alkyl being unsubstituted or substituted by one or more of $-OR_c$ or halogen (F, Cl, I, Br), being $R_c$ represented by $R_{13}$, (being $R_{c'}$ represented by $R_{13'}$, being $R_{c''}$ represented by $R_{13''}$; being $R_{c'''}$ represented by $R_{13'''}$), wherein $R_1$ to $R_{14'''}$ and $R_w$ and $R_x$ are as defined in the description, and wherein when different radicals $R_1$ to $R_{14'''}$ and $R_w$ and $R_x$ are present simultaneously in Formula I they may be identical or different.

More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. $-CH(OH)-CH=CH-CHCl_2$.

In the context of this invention haloalkyl is understood as meaning an alkyl being substituted once or several times by a halogen (selected from F, Cl, Br, I). It encompasses e.g. $-CH_2Cl$, $-CH_2F$, $-CHCl_2$, $-CHF_2$, $-CCl_3$, $-CF_3$ and $-CH_2-CHCl_2$. Preferably haloalkyl is understood in the context of this invention as halogen-substituted $C_{1-4}$-alkyl representing halogen substituted C1-, C2-, C3- or C4-alkyl. The halogen-substituted alkyl radicals are thus preferably methyl, ethyl, propyl, and butyl. Preferred examples include $-CH_2Cl$, $-CH_2F$, $-CHCl_2$, $-CHF_2$, and $-CF_3$.

In the context of this invention haloalkoxy is understood as meaning an $-O$-alkyl being substituted once or several times by a halogen (selected from F, Cl, Br, I). It encompasses e.g. $-OCH_2Cl$, $-OCH_2F$, $-OCHCl_2$, $-OCHF_2$, $-OCCl_3$, $-OCF_3$ and $-OCH_2-CHCl_2$. Preferably haloalkoxy is understood in the context of this invention as halogen-substituted $-OC_{1-4}$-alkyl representing halogen substituted C1-, C2-, C3- or C4-alkoxy. The halogen-substituted alkyl radicals are thus preferably O-methyl, O-ethyl, O-propyl, and O-butyl. Preferred examples include $-OCH_2Cl$, $-OCH_2F$, $-OCHCl_2$, $-OCHF_2$, and $-OCF_3$.

Most preferably in connection with alkyl (also in alkylaryl, alkylheterocyclyl or alkylcycloalkyl), alkenyl, alkynyl or O-alkyl, substituted is understood in the context of this invention that any alkyl (also in alkylaryl, alkylheterocyclyl or alkylcycloalkyl), alkenyl, alkynyl or O-alkyl which is substituted with one or more of halogen (F, Cl, Br, I), $-OR_c$, $-CN$, haloalkyl, haloalkoxy or $-OC_{1-4}$alkyl being unsubstituted or substituted by one or more of $-OR_c$ or halogen (F, Cl, I, Br), being $R_c$ represented by $R_{13}$, (being $R_{c'}$ represented by $R_{13'}$; being $R_{c''}$ represented by $R_{13''}$; being $R_{c'''}$ represented by $R_{13'''}$), wherein $R_1$ to $R_{14'''}$ and $R_w$ and $R_x$ are as defined in the description, and wherein when different radicals $R_1$ to $R_{14'''}$ and $R_w$ and $R_x$ are present simultaneously in Formula I they may be identical or different.

Aryl is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or once or several times substituted. Most preferably aryl is understood in the context of this invention as phenyl, naphtyl or anthracenyl, preferably is phenyl.

In the context of this invention alkylaryl is understood as meaning an aryl group (see above) being connected to another atom through a $C_{1-6}$-alkyl (see above) which may be branched or linear and is unsubstituted or substituted once or several times. Preferably alkylaryl is understood as meaning an aryl group (see above) being connected to another atom through 1 to 4 ($-CH_2-$) groups. Most preferably alkylaryl is benzyl (i.e. $-CH_2$-phenyl).

In the context of this invention alkylheterocyclyl is understood as meaning an heterocyclyl group being connected to another atom through a $C_{1-6}$-alkyl (see above) which may be branched or linear and is unsubstituted or substituted once or several times. Preferably alkylheterocyclyl is understood as meaning an heterocyclyl group (see above) being connected to another atom through 1 to 4 ($-CH_2-$) groups. Most preferably alkylheterocyclyl is $-CH_2$-pyridine.

In the context of this invention alkylcycloalkyl is understood as meaning an cycloalkyl group being connected to another atom through a $C_{1-6}$-alkyl (see above) which may be branched or linear and is unsubstituted or substituted once or several times. Preferably alkylcycloalkyl is understood as meaning an cycloalkyl group (see above) being connected to another atom through 1 to 4 ($-CH_2-$) groups. Most preferably alkylcycloalkyl is $-CH_2$-cyclopropyl.

A heterocyclyl radical or group (also called heterocyclyl hereinafter) is understood as meaning heterocyclic ring systems, with at least one saturated or unsaturated ring which contains one or more heteroatoms from the group consisting of nitrogen, oxygen and/or sulfur in the ring. A heterocyclic group can also be substituted once or several times.

Examples include non-aromatic heterocyclyls such as tetrahydropyrane, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, thiazole, benzothiazole, indole, benzotriazole, carbazole and quinazoline.

Subgroups inside the heterocyclyls as understood herein include heteroaryls and non-aromatic heterocyclyls.

the heteroaryl (being equivalent to heteroaromatic radicals or aromatic heterocyclyls) is an aromatic heterocyclic ring system of one or more rings of which at least one aromatic ring contains one or more heteroatoms from the group consisting of nitrogen, oxygen and/or sulfur in the ring; preferably is an aromatic heterocyclic ring system of one or two rings of which at least one aromatic ring contains one or more heteroatoms from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;

the non-aromatic heterocyclyl is a heterocyclic ring system of one or more rings of which at least one ring—with this (or these) ring(s) then not being aromatic—contains one or more heteroatoms from the group consisting of nitrogen, oxygen and/or sulfur in the ring; preferably is a heterocyclic ring system of one or two rings of which one or both rings—with this one or two rings then not being aromatic—contain/s one or more heteroatoms from the group consisting of nitrogen, oxygen and/or sulfur in the ring, more preferably is selected from oxazepam, pyrrolidine, piperidine, piperazine, tetrahydropyran, morpholine, indoline, oxopyrrolidine, benzodioxane, especially is benzodioxane, morpholine, tetrahydropyran, piperidine, oxopyrrolidine, and pyrrolidine.

Preferably in the context of this invention heterocyclyl is defined as a heterocyclic ring system of one or more saturated or unsaturated rings of which at least one ring contains one or more heteroatoms from the group consisting of nitrogen, oxygen and/or sulfur in the ring. Preferably it is a heterocyclic ring system of one or two saturated or unsaturated rings of which at least one ring contains one or more heteroatoms from the group consisting of nitrogen, oxygen and/or sulfur in the ring.

Preferred examples of heterocyclyls include oxazepan, pyrrolidine, imidazole, oxadiazole, tetrazole, pyridine, pyrimidine, piperidine, piperazine, benzofuran, benzimidazole, indazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyrane, pyrazole, imidazole, piperidine, thiophene, indole, benzimidazole, pyrrolo[2,3b]pyridine, benzoxazole, oxopyrrolidine, pyrimidine, oxazepane and pyrrolidine.

In the context of this invention oxopyrrolidine is understood as meaning pyrrolidin-2-one.

In connection with aromatic heterocyclyls (heteroaryls), non-aromatic heterocyclyls, aryls and cycloalkyls, when a ring system falls within two or more of the above cycle definitions simultaneously, then the ring system is defined first as an aromatic heterocyclyl (heteroaryl) if at least one aromatic ring contains a heteroatom. If no aromatic ring contains a heteroatom, then the ring system is defined as a non-aromatic heterocyclyl if at least one non-aromatic ring contains a heteroatom. If no non-aromatic ring contains a heteroatom, then the ring system is defined as an aryl if it contains at least one aryl cycle. If no aryl is present, then the ring system is defined as a cycloalkyl if at least one non-aromatic cyclic hydrocarbon is present.

Preferably, the aryl is a monocyclic aryl.
Preferably, the heteroaryl is a monocyclic heteroaryl.
Preferably, the non-aromatic heterocyclyl is a monocyclic non-aromatic heterocyclyl.
Preferably, the cycloalkyl is a monocyclic cycloalkyl.

In connection with aryl (including alkyl-aryl), cycloalkyl (including alkyl-cycloalkyl), or heterocyclyl (including alkyl-heterocyclyl), substituted is understood—unless defined otherwise—as meaning substitution of the ring-system of the aryl or alkyl-aryl, cycloalkyl or alkyl-cycloalkyl; heterocyclyl or alkyl-heterocyclyl with one or more of halogen (F, Cl, Br, I), —$R_c$, —$OR_c$, —CN, —$NO_2$, —$NR_cR_{c'''}$, —$C(O)OR_c$, $NR_cC(O)R_{c'}$, —$C(O)NR_cR_{c'}$, —$NR_cS(O)_2R_{c'}$, =O, —$OCH_2CH_2OH$, —$NR_cC(O)NR_{c'}R_{c''}$, —$S(O)_2NR_cR_{c'}$, —$NR_cS(O)_2NR_{c'}R_{c''}$, haloalkyl, haloalkoxy, —$SR_c$, —$S(O)R_c$, —$S(O)_2R_c$ or $C(CH_3)OR_c$; $NR_cR_{c'''}$, with $R_c$ and $R_{c'''}$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl-group; a saturated or unsaturated, linear or branched, substituted or unsubstituted —C(O)—O—$C_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl, being $R_c$ one of $R_8$, $R_9$ or $R_{14}$, (being $R_{c'}$ one of $R_{8'}$, $R_{9'}$ or $R_{14'}$, being $R_{c''}$ one of $R_{8'}$, $R_{9'}$ or $R_{14'}$; being $R_{c'''}$ one of $R_{8''}$, $R_{9''}$ or $R_{14''}$; being $R_{c''''}$ one of $R_{8'''}$, $R_{9'''}$ or $R_{14'''}$), wherein $R_1$ to $R_{14'''}$ and $R_w$ and $R_x$ are as defined in the description, and wherein when different radicals $R_1$ to $R_{14'''}$ and $R_w$ and $R_x$ are present simultaneously in Formula I they may be identical or different.

Most preferably in connection with aryl (including alkyl-aryl), cycloalkyl (including alkyl-cycloalkyl), or heterocyclyl (including alkyl-heterocyclyl), substituted is understood in the context of this invention that any aryl, cycloalkyl and heterocyclyl which is substituted is substituted (also in an alyklaryl, alkylcycloalkyl or alkylheterocyclyl) with one or more of halogen (F, Cl, Br, I), —$R_c$, —$OR_c$, —CN, —$NO_2$, —$NR_cR_{c'''}$, $NR_cC(O)R_{c'}$, —$NR_cS(O)_2R_{c'}$, =O, haloalkyl, haloalkoxy, or $C(CH_3)OR_c$; —$OC_{1-4}$alkyl being unsubstituted or substituted with one or more of $OR_c$ or halogen (F, Cl, I, Br), —CN, or —$C_{1-4}$alkyl being unsubstituted or substituted with one or more of $OR_c$ or halogen (F, Cl, I, Br), being $R_c$ one of $R_8$, $R_9$ or $R_{14}$, (being $R_{c'}$ one of $R_{8'}$, $R_{9'}$ or $R_{14'}$; being $R_{c''}$ one of $R_{8'}$, $R_{9'}$ or $R_{14'}$; being $R_{c'''}$ one of $R_{8''}$, $R_{9''}$ or $R_{14''}$; being $R_{c''''}$ one of $R_{8'''}$, $R_{9'''}$ or $R_{14'''}$), wherein $R_1$ to $R_{14'''}$ and $R_w$ and $R_x$ are as defined in the description, and wherein when different radicals $R_1$ to $R_{14'''}$ and $R_w$ and $R_x$ are present simultaneously in Formula I they may be identical or different.

Additionally to the above-mentioned substitutions, in connection with cycloalkyl (including alkyl-cycloalkyl), or heterocycly (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl; non-aromatic heterocyclyl or non aromatic alkylheterocyclyl with

or =O.

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—) or mesylate.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with $NH_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or of a nitrogen by $^{15}N$-enriched nitrogen are within the scope of this invention.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts. This applies also to its solvates or prodrugs.

In a further embodiment the compound according to the invention of general Formula (I) is a compound wherein n is 1, 2, 3, 4, 5 or 6;

m is 1 or 2;

W is —O—, —$NR_w$—, —S— or —S(O)—;

X is selected from a bond, and —$CR_xR_{x'}$—;

$R_1$ is substituted or unsubstituted cycloalkyl, substituted or unsubstituted aryl, or substituted or unsubstituted heterocyclyl;

wherein said cycloalkyl, aryl or heterocyclyl in $R_1$, if substituted, being substituted with one or more substituent/s selected from halogen, —$R_8$, —$OR_8$, —$NO_2$, —$NR_8R_{8'''}$, $NR_8C(O)R_{8'}$, —$NR_8S(O)_2R_{8'}$, —$S(O)_2NR_8$ $R_{8'}$, —$NR_8C(O)NR_{8'}R_{8''}$, —$SR_8$, —$S(O)R_8$, $S(O)_2$ $R_8$, —CN, haloalkyl, haloalkoxy, —$C(O)OR_8$, —$C(O)NR_8R_{8'}$, —$OCH_2CH_2OH$, —$NR_8S(O)_2$ $NR_8R_{8''}$ and —$C(CH_3)_2OR_8$;

wherein $R_8$, $R_{8'}$ and $R_{8''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl, unsubstituted alkylcycloalkyl, unsubstituted heterocyclyl and unsubstituted alkyheterocyclyl;

and wherein $R_{8'''}$ is selected from hydrogen, unsubstituted $C_{1-8}$ alkyl, unsubstituted $C_{2-6}$ alkenyl, unsubstituted $C_{2-6}$ alkynyl and -Boc;

$R_2$ is substituted or unsubstituted cycloalkyl, substituted or unsubstituted aryl, or substituted or unsubstituted heterocyclyl;

wherein said cycloalkyl, aryl or heterocyclyl in $R_2$, if substituted, is substituted with one or more substituent/s selected from halogen, —$R_9$, —$OR_9$, —$NO_2$, —$NR_9R_{9'''}$, $NR_9C(O)R_{9'}$, —$NR_9S(O)_2R_{9'}$, —$S(O)_2$ $NR_9$ $R_{9'}$, —$NR_9C(O)NR_{9'}R_{9''}$, —$SR_9$, —$S(O)R_9$, $S(O)_2$ $R_9$, —CN, haloalkyl, haloalkoxy, —$C(O)NR_9R_{9'}$, —$OCH_2CH_2OH$, —$NR_9S(O)_2NR_9R_{9''}$ and $C(CH_3)_2OR_9$;

wherein $R_9$, $R_{9'}$ and $R_{9''}$ are independently selected from hydrogen, unsubstituted $C_{1-6}$ alkyl, and unsubstituted $C_{2-6}$ alkenyl, unsubstituted $C_{2-6}$ alkynyl;

and wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

$R_3$ is hydrogen, or substituted or unsubstituted $C_{1-6}$ alkyl, substituted or unsubstituted $C_{2-6}$ alkenyl, or substituted or unsubstituted $C_{2-6}$ alkynyl;

$R_4$ and $R_{4'}$ are independently selected from hydrogen, unsubstituted $C_{1-6}$ alkyl, unsubstituted $C_{2-6}$ alkenyl, and unsubstituted $C_{2-6}$ alkynyl;

$R_5$ is selected from hydrogen, substituted or unsubstituted $C_{1-6}$ alkyl, substituted or unsubstituted $C_{2-6}$ alkenyl, and substituted or unsubstituted $C_{2-6}$ alkynyl;

$R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)OR$_{10}$ and —C(O)NR$_{10}$R$_{10'}$;
  wherein $R_{10}$ and $R_{10'}$ are independently selected from hydrogen, unsubstituted $C_{1-6}$ alkyl, unsubstituted $C_{2-6}$ alkenyl and unsubstituted $C_{2-6}$ alkynyl;

$R_x$ is selected from hydrogen, halogen, —OR$_{11}$, substituted or unsubstituted $C_{1-6}$ alkyl, substituted or unsubstituted $C_{2-6}$ alkenyl, substituted or unsubstituted $C_{2-6}$ alkynyl, —C(O)OR$_{11}$, —C(O)NR$_{11}$R$_{11'}$, —NR$_{11}$C(O)R$_{11''}$, and —NR$_{11}$R$_{11'''}$;

$R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
  wherein $R_{11}$, $R_{11'}$ and $R_{11''}$ are independently selected from hydrogen, unsubstituted $C_{1-6}$ alkyl, unsubstituted $C_{2-6}$ alkenyl, and unsubstituted $C_{2-6}$ alkynyl;
  and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

$R_w$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)R$_{12}$, —C(O)OR$_{12}$, and —C(O)NR$_{12}$R$_{12'}$;
  wherein $R_{12}$ and $R_{12'}$ are independently selected from hydrogen, unsubstituted $C_{1-6}$ alkyl, unsubstituted $C_{2-6}$ alkenyl and unsubstituted $C_{2-6}$ alkynyl;

and/or
wherein the alkyl, alkylene or alkynyl, other than those defined in $R_1$ or $R_2$, if substituted, is substituted with one or more substituents selected from —OR$_{13}$, halogen, —CN, haloalkyl, haloalkoxy, —NR$_{13}$R$_{13'''}$, —SR$_{13}$, —S(O)R$_{13}$, and —S(O)$_2$R$_{13}$;
  wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;
  and wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

and/or
wherein the aryl, heterocyclyl or cycloalkyl, also in alkylaryl, alkylcycloalkyl and alkylheterocyclyl, other than those defined in $R_1$ or $R_2$, if substituted, is substituted with one or more substituents selected from halogen, —R$_{14}$, —OR$_{14}$, —NO$_2$, —NR$_{14}$R$_{14'''}$, NR$_{14}$C(O)R$_{14'}$, —NR$_{14}$S(O)$_2$ R$_{14'}$, —S(O)$_2$NR$_{14}$R$_{14'}$, —NR$_{14}$C(O)NR$_{14'}$R$_{14'''}$, —SR$_{14}$, —S(O)R$_{14}$, S(O)$_2$R$_{14}$, —CN, haloalkyl, haloalkoxy, —C(O)OR$_{14}$, —C(O)NR$_{14}$R$_{14'}$, —OCH$_2$CH$_2$OH, —NR$_{14}$S(O)$_2$ NR$_{14'}$R$_{14''}$ and C(CH$_3$)$_2$OR$_{14}$;
  wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl, unsubstituted alkylcycloalkyl, unsubstituted heterocyclyl and unsubstituted alkyheterocylcyl;
  and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

These preferred compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
  n is 1, 2, 3, 4, 5 or 6;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
  n is 1 or 2;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
  m is 1 or 2;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general f Formula (I) is a compound wherein
  W is —O—, —NR$_w$—, —S— or —S(O)—;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
  X is selected from a bond and —CR$_x$R$_{x'}$;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
  $R_1$ is substituted or unsubstituted cycloalkyl, substituted or unsubstituted aryl, or substituted or unsubstituted heterocyclyl;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is substituted or unsubstituted aryl or substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is substituted or unsubstituted cycloalkyl, substituted or unsubstituted aryl, or substituted or unsubstituted heteroaryl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is substituted or unsubstituted cycloalkyl, substituted or unsubstituted aryl, or substituted or unsubstituted heterocyclyl; optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_3$ is hydrogen, or substituted or unsubstituted $C_{1-6}$ alkyl, substituted or unsubstituted $C_{2-6}$ alkenyl, or substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_3$ is substituted or unsubstituted $C_{1-6}$ alkyl, substituted or unsubstituted $C_{2-6}$ alkenyl, or substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_3$ is substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_4$ and $R_{4'}$ are independently selected from hydrogen, unsubstituted $C_{1-6}$ alkyl, unsubstituted $C_{2-6}$ alkenyl, and unsubstituted $C_{2-6}$ alkynyl, preferably $R_4$ and $R_{4'}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_5$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)OR$_7$ and —C(O)NR$_7$R$_{7'}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_5$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_5$ is selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)OR$_{10}$ and —C(O)NR$_{10}$R$_{10'}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_6$ and $R_{6'}$ are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_7$ and $R_{7'}$ are independently selected from hydrogen, unsubstituted $C_{1-6}$ alkyl, unsubstituted $C_{2-6}$ alkenyl and unsubstituted $C_{2-6}$ alkynyl, preferably $R_7$ and $R_{7'}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_8$, $R_{8'}$ and $R_{8''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl, unsubstituted alkylcycloalkyl, unsubstituted heterocyclyl and unsubstituted alkyheterocyclyl;

and wherein $R_{8'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_8$, $R_{8'}$ and $R_{8''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl, unsubstituted alkylcycloalkyl, unsubstituted heterocyclyl and unsubstituted alkyheterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_8$, $R_{8'}$ and $R_{8''}$ are independently selected from hydrogen, unsubstituted $C_{1-6}$ alkyl, unsubstituted $C_{2-6}$ alkenyl and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_8$, $R_{8'}$ and $R_{8''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{8'''}$ is selected from hydrogen, unsubstituted $C_{1-6}$ alkyl, unsubstituted $C_{2-6}$ alkenyl, unsubstituted $C_{2-6}$ alkynyl and -Boc, preferably, $R_{8'''}$ is selected from hydrogen, unsubstituted $C_{1-6}$ alkyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_9$, $R_{9'}$ and $R_{9''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_9$, $R_{9'}$ and $R_{9''}$ are independently selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_9$, $R_{9'}$ and $R_{9''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc, preferably, $R_{9'''}$ is selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{10}$ and $R_{10'}$ are independently selected from hydrogen, unsubstituted $C_{1-6}$ alkyl, unsubstituted $C_{2-6}$ alkenyl and unsubstituted $C_{2-6}$ alkynyl, preferably, $R_{10}$ and $R_{10'}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11}$, $R_{11'}$ and $R_{11''}$ are independently selected from hydrogen, unsubstituted $C_{1-6}$ alkyl, unsubstituted $C_{2-6}$ alkenyl, and unsubstituted $C_{2-6}$ alkynyl, preferably, $R_{11}$, $R_{11'}$ and $R_{11''}$ are independently selected from hydrogen and unsubstituted $C_{1-6}$ alkyl; and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11}$, $R_{11'}$ and $R_{11''}$ are independently selected from hydrogen, unsubstituted $C_{1-6}$ alkyl, unsubstituted $C_{2-6}$ alkenyl, and unsubstituted $C_{2-6}$ alkynyl, preferably, $R_{11}$, $R_{11'}$ and $R_{11''}$ are independently selected from hydrogen, unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc, preferably $R_{11'''}$ is selected from hydrogen, unsubstituted $C_{1-6}$ alkyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12}$ and $R_{12'}$ are independently selected from hydrogen, unsubstituted $C_{1-6}$ alkyl, unsubstituted $C_{2-6}$ alkenyl and unsubstituted $C_{2-6}$ alkynyl, preferably $R_{12}$ and $R_{12'}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl, preferably $R_{13}$, $R_{13'}$ and $R_{13''}$ are independently selected from hydrogen and unsubstituted $C_{1-6}$ alkyl; optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc, preferably $R_{13'''}$ is selected from hydrogen, unsubstituted $C_{1-6}$ alkyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl, unsubstituted alkylcycloalkyl, unsubstituted heterocyclyl and unsubstituted alkyheterocylcyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl, unsubstituted alkylcycloalkyl, unsubstituted heterocyclyl and unsubstituted alkyheterocylcyl, preferably $R_{14}$, $R_{14'}$ and $R_{14''}$ are independently selected from hydrogen, unsubstituted $C_{1-6}$ alkyl, unsubstituted aryl, unsubstituted alkylaryl, unsubstituted cycloalkyl, unsubstituted alkylcycloalkyl, unsubstituted heterocyclyl and unsubstituted alkyheterocylcyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc, preferably $R_{14'''}$ is selected from hydrogen, unsubstituted $C_{1-6}$ alkyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_x$ is selected from hydrogen, halogen, —$OR_{11}$, substituted or unsubstituted $C_{1-6}$ alkyl, substituted or unsubstituted $C_{2-6}$ alkenyl, substituted or unsubstituted $C_{2-6}$ alkynyl, —$C(O)OR_{11}$, —$C(O)NR_{11}R_{11'}$, —$NR_{11}C(O)R_{11'}$, and —$NR_{11}R_{11'''}$;

$R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_x$ is selected from hydrogen, halogen, —$OR_{11}$, substituted or unsubstituted $C_{1-6}$ alkyl, substituted or unsubstituted $C_{2-6}$ alkenyl, substituted or unsubstituted $C_{2-6}$ alkynyl, —$C(O)OR_{11}$, —$C(O)NR_{11}R_{11'}$, —$NR_{11}C(O)R_{11'}$, and —$NR_{11}R_{11'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_x$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_x$ is selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{x'}$ is selected from hydrogen, substituted or unsubstituted $C_{1-6}$ alkyl, substituted or unsubstituted $C_{2-6}$ alkenyl substituted or unsubstituted $C_{2-6}$ alkynyl, preferably $R_{x'}$ is selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_w$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —$C(O)R_{12}$, —$C(O)OR_{12}$, and —$C(O)NR_{12}R_{12'}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_w$ is selected from hydrogen, substituted or unsubstituted $C_{1-6}$ alkyl, substituted or unsubstituted $C_{2-6}$ alkenyl, substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_w$ is selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein W is —O—, —$NR_w$—, —S— or —S(O)—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein W is —O—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein X is a bond;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein X is —$CR_xR_x$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein X is —$CH_2$—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein X is —CH(methyl)-;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein m is 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein m is 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 1, X is a bond and $R_2$ is substituted or unsubstituted phenyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 1, X is a bond, $R_1$ is substituted or unsubstituted phenyl and $R_2$ is substituted or unsubstituted phenyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 1, X is a bond, $R_1$ is substituted or unsubstituted thiophen and $R_2$ is substituted or unsubstituted phenyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 2, X is a bond and $R_2$ is substituted or unsubstituted phenyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 2, X is a bond, $R_1$ is substituted or unsubstituted phenyl and $R_2$ is substituted or unsubstituted phenyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 2, X is a bond, $R_1$ is substituted or unsubstituted thiophen and $R_2$ is substituted or unsubstituted phenyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 1, 2, 3, 4, 5 or 6, preferably n is 1 or 2; and/or
m is 1 or 2; and/or
W is —O—, —$NR_w$—, —S— or —S(O)—; and/or
X is selected from a bond, and —$CR_xR_x$; and/or $R_1$ is substituted or unsubstituted cycloalkyl, substituted or unsubstituted aryl, or substituted or unsubstituted heterocyclyl wherein the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocyclyl is pyridine, thiophen or thiazole;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_2$ is substituted or unsubstituted cycloalkyl, substituted or unsubstituted aryl, or substituted or unsubstituted heterocyclyl;

wherein the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocyclyl is pyridine;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or $R_3$ is hydrogen, or substituted or unsubstituted $C_{1-6}$ alkyl, substituted or unsubstituted $C_{2-6}$ alkenyl, or substituted or unsubstituted $C_{2-6}$ alkynyl; wherein the $C_{1-6}$ alkyl is preferably selected from methyl, ethyl, propyl, butyl, pentyl, hexyl, isopropyl, or 2-methylpropyl, more preferably the $C_{1-6}$ alkyl is methyl;
and/or the $C_{2-6}$-alkenyl is preferably selected from ethylene, propylene, butylene, pentylene or hexylene;
and/or the $C_{2-6}$-alkynyl is preferably selected from ethyne, propyne, butyne, pentyne or hexyne;
and/or $R_4$ and $R_{4'}$ are independently selected from hydrogen, unsubstituted $C_{1-6}$ alkyl, unsubstituted $C_{2-6}$ alkenyl, and unsubstituted $C_{2-6}$ alkynyl;

the $C_{1-6}$ alkyl is preferably selected from methyl, ethyl, propyl, butyl, pentyl, hexyl, isopropyl, or 2-methylpropyl;
and/or the $C_{2-6}$-alkenyl is preferably selected from ethylene, propylene, butylene, pentylene or hexylene;
and/or the $C_{2-6}$-alkynyl is preferably selected from ethyne, propyne, butyne, pentyne or hexyne;
and/or $R_5$ is selected from hydrogen, substituted or unsubstituted $C_{1-6}$ alkyl, substituted or unsubstituted $C_{2-6}$ alkenyl and substituted or unsubstituted $C_{2-6}$ alkynyl, wherein the $C_{1-6}$ alkyl is preferably selected from methyl, ethyl, propyl, butyl, pentyl, hexyl, isopropyl, or 2-methylpropyl, more preferably the $C_{1-6}$ alkyl is methyl or isopropyl;
and/or the $C_{2-6}$-alkenyl is preferably selected from ethylene, propylene, butylene, pentylene or hexylene;
and/or the $C_{2-6}$-alkynyl is preferably selected from ethyne, propyne, butyne, pentyne or hexyne;
and/or $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, $-C(O)OR_{10}$ and $-C(O)NR_{10}R_{10'}$; wherein the $C_{1-6}$ alkyl is preferably selected from methyl, ethyl, propyl, butyl, pentyl, hexyl, isopropyl, or 2-methylpropyl, more preferably the $C_{1-6}$ alkyl is methyl;
and/or the $C_{2-6}$-alkenyl is preferably selected from ethylene, propylene, butylene, pentylene or hexylene;
and/or the $C_{2-6}$-alkynyl is preferably selected from ethyne, propyne, butyne, pentyne or hexyne;
and/or In another preferred embodiment of the compound according to the invention of general Formula (I) is a compound wherein $R_7$ and $R_{7'}$ are independently selected from hydrogen, unsubstituted $C_{1-6}$ alkyl, unsubstituted $C_{2-6}$ alkenyl and unsubstituted $C_{2-6}$ alkynyl; wherein the $C_{1-6}$ alkyl is preferably selected from methyl, ethyl, propyl, butyl, pentyl, hexyl, isopropyl, or 2-methylpropyl,
and/or the $C_{2-6}$-alkenyl is preferably selected from ethylene, propylene, butylene, pentylene or hexylene;
and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof;
and/or $R_8$, $R_{8'}$ and $R_{8''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl, unsubstituted alkylcycloalkyl, unsubstituted heterocyclyl and unsubstituted alkyheterocylcyl; wherein the alkyl is $C_{1-6}$ alkyl like methyl, ethyl, propyl, butyl, pentyl or hexyl;
and/or the $C_{1-6}$ alkyl is preferably selected from methyl, ethyl, propyl, butyl, pentyl, hexyl, isopropyl, or 2-methylpropyl; more preferably the $C_{1-6}$ alkyl is methyl;
and/or the $C_{2-6}$-alkenyl is preferably selected from ethylene, propylene, butylene, pentylene or hexylene;
and/or the $C_{2-6}$-alkynyl is preferably selected from ethyne, propyne, butyne, pentyne or hexyne;
and/or the aryl is selected from phenyl, naphtyl, or anthracene; preferably is napthyl and phenyl;
and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;
and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or $R_{8'''}$ is selected from hydrogen, unsubstituted $C_{1-6}$ alkyl, unsubstituted $C_{2-6}$ alkenyl, unsubstituted $C_{2-6}$ alkynyl and -Boc; wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_9$, $R_{9'}$ and $R_{9''}$ are independently selected from hydrogen, unsubstituted $C_{1-6}$ alkyl, unsubstituted $C_{2-6}$ alkenyl, and unsubstituted $C_{2-6}$ alkynyl;

the $C_{1-6}$ alkyl is preferably selected from methyl, ethyl, propyl, butyl, pentyl, hexyl, isopropyl, or 2-methylpropyl, more preferably the $C_{1-6}$ alkyl is methyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_{9'''}$ is selected from hydrogen, unsubstituted $C_{1-6}$ alkyl, unsubstituted $C_{2-6}$ alkenyl, unsubstituted $C_{2-6}$ alkynyl and -Boc; wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_{10}$ and $R_{10'}$ are independently selected from hydrogen, unsubstituted $C_{1-6}$ alkyl, unsubstituted $C_{2-6}$ alkenyl and unsubstituted $C_{2-6}$ alkynyl; wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_x$ is selected from hydrogen, halogen, —$OR_{11}$, substituted or unsubstituted $C_{1-6}$ alkyl, substituted or unsubstituted $C_{2-6}$ alkenyl, substituted or unsubstituted $C_{2-6}$ alkynyl, —$C(O)OR_{11}$, —$C(O)NR_{11}R_{11'}$, —$NR_{11}C(O)R_{11'}$, and —$NR_{11}R_{11'''}$; wherein the $C_{1-6}$ alkyl is preferably selected from methyl, ethyl, propyl, butyl, pentyl, hexyl, isopropyl, or 2-methylpropyl, more preferably the alkyl is methyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl; wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_w$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —$C(O)R_{12}$, —$C(O)OR_{12}$, and —$C(O)NR_{12}R_{12'}$; wherein the $C_{1-6}$ alkyl is preferably selected from methyl, ethyl, propyl, butyl, pentyl, hexyl, isopropyl, or 2-methylpropyl, more preferably the $C_{1-6}$ alkyl is methyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_{11}$, $R_{11'}$ and $R_{11''}$ are independently selected from hydrogen, unsubstituted $C_{1-6}$ alkyl, unsubstituted $C_{2-6}$ alkenyl, and unsubstituted $C_{2-6}$ alkynyl; wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_{11'''}$ is selected from hydrogen, unsubstituted $C_{1-6}$ alkyl, unsubstituted $C_{2-6}$ alkenyl, unsubstituted $C_{2-6}$ alkynyl and -Boc; wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_{12}$ and $R_{12'}$ are independently selected from hydrogen, unsubstituted $C_{1-6}$ alkyl, unsubstituted $C_{2-6}$ alkenyl and unsubstituted $C_{2-6}$ alkynyl; wherein the $C_{1-6}$ alkyl is preferably selected from methyl, ethyl, propyl, butyl, pentyl, hexyl, isopropyl, or 2-methylpropyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
and/or
$R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl; wherein
the $C_{1-6}$ alkyl is preferably selected from methyl, ethyl, propyl, butyl, pentyl, hexyl, isopropyl, or 2-methylpropyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
and/or
$R_{13'''}$ is selected from hydrogen, unsubstituted $C_{1-6}$ alkyl, unsubstituted $C_{2-6}$ alkenyl, unsubstituted $C_{2-6}$ alkynyl and -Boc; wherein
the $C_{1-6}$ alkyl is preferably selected from methyl, ethyl, propyl, butyl, pentyl, hexyl, isopropyl, or 2-methylpropyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
and/or
$R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl, unsubstituted alkylcycloalkyl, unsubstituted heterocyclyl and unsubstituted alkyheterocylcyl; wherein
the alkyl is $C_{1-6}$ alkyl like methyl, ethyl, propyl, butyl, pentyl or hexyl;
and/or
the $C_{1-6}$ alkyl is preferably selected from methyl, ethyl, propyl, butyl, pentyl, hexyl, isopropyl, or 2-methylpropyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
and/or
the aryl is selected from phenyl, naphtyl, or anthracene; preferably is napthyl and phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or
$R_{14'''}$ is selected from hydrogen, unsubstituted $C_{1-6}$ alkyl, unsubstituted $C_{2-6}$ alkenyl, unsubstituted $C_{2-6}$ alkynyl and -Boc; wherein
the $C_{1-6}$ alkyl is preferably selected from methyl, ethyl, propyl, butyl, pentyl, hexyl, isopropyl, or 2-methylpropyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_1$ as defined in any of the embodiments,
the aryl is selected from phenyl, naphtyl, and anthracene; preferably is napthyl and phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocyclyl is pyridine, thiophen or thiazole;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_2$ as defined in any of the embodiments, the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocyclyl is pyridine;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_w$ as defined in any of the embodiments, the $C_{1-6}$ alkyl is preferably selected from methyl, ethyl, propyl, butyl, pentyl, hexyl, isopropyl, or 2-methylpropyl, more preferably the $C_{1-6}$ alkyl is methyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_x$ as defined in any of the embodiments, the $C_{1-6}$ alkyl is preferably selected from methyl, ethyl, propyl, butyl, pentyl, hexyl, isopropyl, or 2-methylpropyl, more preferably the $C_{1-6}$ alkyl is methyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{x'}$ as defined in any of the embodiments, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_3$ as defined in any of the embodiments, the $C_{1-6}$ alkyl is preferably selected from methyl, ethyl, propyl, butyl, pentyl, hexyl, isopropyl, or 2-methylpropyl, more preferably the $C_{1-6}$ alkyl is methyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_4$ and $R_{4'}$ as defined in any of the embodiments, the $C_{1-6}$ alkyl is preferably selected from methyl, ethyl, propyl, butyl, pentyl, hexyl, isopropyl, or 2-methylpropyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_5$ as defined in any of the embodiments,
the $C_{1-6}$ alkyl is preferably selected from methyl, ethyl, propyl, butyl, pentyl, hexyl, isopropyl, or 2-methylpropyl, more preferably the $C_{1-6}$ alkyl is methyl or isopropyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_6$ and $R_{6'}$ as defined in any of the embodiments,
the $C_{1-6}$ alkyl is preferably selected from methyl, ethyl, propyl, butyl, pentyl, hexyl, isopropyl, or 2-methylpropyl, more preferably the $C_{1-6}$ alkyl is methyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_7$ and $R_{7'}$ as defined in any of the embodiments,
the $C_{1-6}$ alkyl is preferably selected from methyl, ethyl, propyl, butyl, pentyl, hexyl, isopropyl, or 2-methylpropyl,
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_8$, $R_{8'}$ and $R_{8''}$ as defined in any of the embodiments,
the alkyl is $C_{1-6}$ alkyl like methyl, ethyl, propyl, butyl, pentyl or hexyl;
and/or
the $C_{1-6}$ alkyl is preferably selected from methyl, ethyl, propyl, butyl, pentyl, hexyl, isopropyl, or 2-methylpropyl; more preferably the $C_{1-6}$ alkyl is methyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
and/or
the aryl is selected from phenyl, naphtyl, or anthracene; preferably is napthyl and phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{8'''}$ as defined in any of the embodiments,
the $C_{1-6}$ alkyl is preferably selected from methyl, ethyl, propyl, butyl, pentyl, hexyl, isopropyl, or 2-methylpropyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_9$, $R_{9'}$ and $R_{9''}$ as defined in any of the embodiments,
- the $C_{1-6}$ alkyl is preferably selected from methyl, ethyl, propyl, butyl, pentyl, hexyl, isopropyl, or 2-methylpropyl, more preferably the $C_{1-6}$ alkyl is methyl;
- and/or
- the $C_{2-6}$-alkenyl is preferably selected from ethylene, propylene, butylene, pentylene or hexylene;
- and/or
- the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{9'''}$ as defined in any of the embodiments,
- the $C_{1-6}$ alkyl is preferably selected from methyl, ethyl, propyl, butyl, pentyl, hexyl, isopropyl, or 2-methylpropyl;
- and/or
- the $C_{2-6}$-alkenyl is preferably selected from ethylene, propylene, butylene, pentylene or hexylene;
- and/or
- the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{10}$ and $R_{10'}$ as defined in any of the embodiments,
- the $C_{1-6}$ alkyl is preferably selected from methyl, ethyl, propyl, butyl, pentyl, hexyl, isopropyl, or 2-methylpropyl;
- and/or
- the $C_{2-6}$-alkenyl is preferably selected from ethylene, propylene, butylene, pentylene or hexylene;
- and/or
- the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11}$, $R_{11'}$ and $R_{11''}$ as defined in any of the embodiments,
- the $C_{1-6}$ alkyl is preferably selected from methyl, ethyl, propyl, butyl, pentyl, hexyl, isopropyl, or 2-methylpropyl;
- and/or
- the $C_{2-6}$-alkenyl is preferably selected from ethylene, propylene, butylene, pentylene or hexylene;
- and/or
- the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11'''}$ as defined in any of the embodiments,
- the $C_{1-6}$ alkyl is preferably selected from methyl, ethyl, propyl, butyl, pentyl, hexyl, isopropyl, or 2-methylpropyl;
- and/or
- the $C_{2-6}$-alkenyl is preferably selected from ethylene, propylene, butylene, pentylene or hexylene;
- and/or
- the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{12}$ and $R_{12'}$ as defined in any of the embodiments,
- the $C_{1-6}$ alkyl is preferably selected from methyl, ethyl, propyl, butyl, pentyl, hexyl, isopropyl, or 2-methylpropyl;
- and/or
- the $C_{2-6}$-alkenyl is preferably selected from ethylene, propylene, butylene, pentylene or hexylene;
- and/or
- the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{13}$, $R_{13'}$ and $R_{13''}$ as defined in any of the embodiments,
- the $C_{1-6}$ alkyl is preferably selected from methyl, ethyl, propyl, butyl, pentyl, hexyl, isopropyl, or 2-methylpropyl;
- and/or
- the $C_{2-6}$-alkenyl is preferably selected from ethylene, propylene, butylene, pentylene or hexylene;
- and/or
- the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{13'''}$ as defined in any of the embodiments,
- the $C_{1-6}$ alkyl is preferably selected from methyl, ethyl, propyl, butyl, pentyl, hexyl, isopropyl, or 2-methylpropyl;
and/or
- the $C_{2-6}$-alkenyl is preferably selected from ethylene, propylene, butylene, pentylene or hexylene;
and/or
- the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{14}$, $R_{14'}$ and $R_{14''}$ as defined in any of the embodiments,
- the alkyl is $C_{1-6}$ alkyl like methyl, ethyl, propyl, butyl, pentyl or hexyl;
and/or
- the $C_{1-6}$ alkyl is preferably selected from methyl, ethyl, propyl, butyl, pentyl, hexyl, isopropyl, or 2-methylpropyl;
and/or
- the $C_{2-6}$-alkenyl is preferably selected from ethylene, propylene, butylene, pentylene or hexylene;
and/or
- the $C_{2-6}$-alkynyl is preferably selected from ethyne, propyne, butyne, pentyne or hexyne;
and/or
- the aryl is selected from phenyl, naphtyl, or anthracene; preferably is napthyl and phenyl;
and/or
- the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;
and/or
- the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{14'''}$ as defined in any of the embodiments,
- the $C_{1-6}$ alkyl is preferably selected from methyl, ethyl, propyl, butyl, pentyl, hexyl, isopropyl, or 2-methylpropyl;
and/or
- the $C_{2-6}$-alkenyl is preferably selected from ethylene, propylene, butylene, pentylene or hexylene;
and/or
- the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein
n is 1, 2, 3, 4, 5 or 6, preferably n is 1 or 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein
X is selected from a bond, and $—CR_xR_{x'}$—, preferably X is a bond;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein
W is —O—, —NR$_w$—, —S— or —S(O)—, preferably W is —O—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment
$R_1$ is a substituted or unsubstituted group selected from phenyl, pyridine, thiophen and thiazole.
In another preferred embodiment
$R_1$ is a substituted or unsubstituted group selected from phenyl and thiophen.
In a most preferred embodiment
$R_1$ is substituted or unsubstituted phenyl.
In another preferred embodiment
$R_1$ is substituted or unsubstituted thiophen.
In a preferred embodiment
$R_2$ is a substituted or unsubstituted phenyl or a substituted or unsubstituted pyridine.
In a preferred embodiment
$R_3$ is substituted or unsubstituted methyl.
In a preferred embodiment
$R_4$ and $R_{4'}$ are both hydrogen.
In a preferred embodiment
$R_5$ is a substituted or unsubstituted group selected from methyl and isopropyl.
In a preferred embodiment
$R_6$ is selected from hydrogen and substituted or unsubstituted methyl.
In another preferred embodiment
$R_{6'}$ is hydrogen.
In another preferred embodiment
$R_6$ is hydrogen or substituted or unsubstituted methyl while and $R_{6'}$ is hydrogen.
In another preferred embodiment
$R_6$ is substituted or unsubstituted methyl while $R_{6'}$ is hydrogen.
In another preferred embodiment
$R_6$ and $R_{6'}$ are both hydrogen.

In a preferred embodiment
$R_8$ is selected from hydrogen and unsubstituted methyl.
In a preferred embodiment
$R_9$ is unsubstituted methyl.
In a preferred embodiment
$R_x$ is selected from hydrogen and substituted or unsubstituted methyl.
In a preferred embodiment
$R_x'$ is hydrogen.
In a preferred embodiment
$R_x$ is hydrogen or substituted or unsubstituted methyl while $R_x'$ is hydrogen.
In a preferred embodiment
$R_x$ is substituted or unsubstituted methyl while $R_x'$ is hydrogen.
In a preferred embodiment
$R_x$ and $R_x'$ are both hydrogen.
In a preferred embodiment
$R_w$ is substituted or unsubstituted methyl.
In another preferred embodiment
n is 1 or 2.
In another preferred embodiment
m is 1 or 2.
In another preferred embodiment
W is —O—, —N(methyl)-, —S—, or —S(O)—.
In another preferred embodiment
X is a bond, —CH$_2$—, or —CH(methyl)-.
In an particular embodiment
the halogen is fluorine, chlorine, iodine or bromine.
In an particular embodiment
the halogen is fluorine or chlorine.
In a preferred further embodiment, the compounds of the general Formula (I) are selected from

| EX | Chemical name |
|---|---|
| 1 | N-benzyl-N-methyl-2-((1-methyl-1H-pyrazol-5-yl)(thiophen-2-yl)methoxy)ethanamine |
| 2 | N-((6-methoxypyridin-3-yl)methyl)-N-methyl-2-((1-methyl-1H-pyrazol-5-yl)(phenyl)methoxy)ethanamine |
| 3 | N-methyl-2-((1-methyl-1H-pyrazol-5-yl)(phenyl)methoxy)-N-((6-(trifluoromethyl)pyridin-3-yl)methyl)ethanamine |
| 4 | N-methyl-2-((1-methyl-1H-pyrazol-5-yl)(thiophen-2-yl)methoxy)-N-phenethylethanamine |
| 5 | N-(4-fluorobenzyl)-N-methyl-2-((1-methyl-1H-pyrazol-5-yl)(thiophen-2-yl)methoxy)ethanamine |
| 6 | N-benzyl-N-methyl-2-((1-methyl-1H-pyrazol-5-yl)(phenyl)methoxy)ethanamine |
| 7 | N-methyl-2-((1-methyl-1H-pyrazol-5-yl)(phenyl)methoxy)-N-phenethylethanamine |
| 8 | N-(4-fluorobenzyl)-N-methyl-2-((1-methyl-1H-pyrazol-5-yl)(phenyl)methoxy)ethanamine |
| 9 | (R)-N-benzyl-N-methyl-2-((1-methyl-1H-pyrazol-5-yl)(phenyl)methoxy)ethanamine |
| 10 | (R)-N-(4-fluorobenzyl)-N-methyl-2-((1-methyl-1H-pyrazol-5-yl)(phenyl)methoxy)ethanamine |
| 11 | (R)-N-methyl-2-((1-methyl-1H-pyrazol-5-yl)(phenyl)methoxy)-N-phenethylethanamine |
| 12 | N-(4-chloro-2-fluorobenzyl)-N-methyl-2-((1-methyl-1H-pyrazol-5-yl)(thiophen-2-yl)methoxy)ethanamine |
| 13 | N-(4-chloro-2-fluorobenzyl)-N-methyl-2-((1-methyl-1H-pyrazol-5-yl)(phenyl)methoxy)ethanamine |
| 14 | N-methyl-2-((1-methyl-1H-pyrazol-5-yl)(thiophen-2-yl)methoxy)-N-(1-phenylethyl)ethanamine |
| 15 | N-methyl-2-((1-methyl-1H-pyrazol-5-yl)(thiophen-2-yl)methoxy)-N-(3-methylbenzyl)ethanamine |
| 16 | N-methyl-2-((1-methyl-1H-pyrazol-5-yl)(phenyl)methoxy)-N-(1-phenylethyl)ethanamine |
| 17 | N-methyl-2-((1-methyl-1H-pyrazol-5-yl)(phenyl)methoxy)-N-(3-methylbenzyl)ethanamine |
| 18 | (R)-N-benzyl-N-methyl-2-((1-methyl-1H-pyrazol-5-yl)(thiophen-2-yl)methoxy)ethanamine |
| 19 | (S)-N-methyl-2-((1-methyl-1H-pyrazol-5-yl)(phenyl)methoxy)-N-phenethylethanamine |
| 20 | (R)-N-methyl-2-((1-methyl-1H-pyrazol-5-yl)(thiophen-2-yl)methoxy)-N-phenethylethanamine |
| 21 | (S)-N-benzyl-N-methyl-2-((1-methyl-1H-pyrazol-5-yl)(phenyl)methoxy)ethanamine |
| 22 | (S)-N-(4-fluorobenzyl)-N-methyl-2-((1-methyl-1H-pyrazol-5-yl)(phenyl)methoxy)ethanamine |
| 23 | N-(3-methoxybenzyl)-N-methyl-2-((1-methyl-1H-pyrazol-5-yl)(phenyl)methoxy)ethanamine |
| 24 | N-(3-fluorobenzyl)-N-methyl-2-((1-methyl-1H-pyrazol-5-yl)(phenyl)methoxy)ethanamine |
| 25 | N-(3-chlorobenzyl)-N-methyl-2-((1-methyl-1H-pyrazol-5-yl)(phenyl)methoxy)ethanamine |

| EX | Chemical name |
|---|---|
| 26 | (S)-N-(3-fluorobenzyl)-N-methyl-2-((1-methyl-1H-pyrazol-5-yl)(phenyl)methoxy)ethanamine |
| 27 | N-benzyl-N-(2-((1-methyl-1H-pyrazol-5-yl)(phenyl)methoxy)ethyl)propan-2-amine |
| 28 | N-(3-fluorobenzyl)-N-methyl-2-((1-methyl-1H-pyrazol-5-yl)(thiophen-2-yl)methoxy)ethanamine |
| 29 | N-(3-fluorobenzyl)-N-(2-((1-methyl-1H-pyrazol-5-yl)(phenyl)methoxy)ethyl)propan-2-amine |
| 30 | (S)-N-benzyl-N-methyl-2-((1-methyl-1H-pyrazol-5-yl)(3-methylthiophen-2-yl)methoxy)ethanamine |
| 31 | (R)-N-benzyl-N-methyl-2-((1-methyl-1H-pyrazol-5-yl)(3-methylthiophen-2-yl)methoxy)ethanamine |
| 32 | N-(3,4-dichlorophenethyl)-N-methyl-2-((1-methyl-1H-pyrazol-5-yl)(thiophen-2-yl)methoxy)ethanamine |
| 33 | N-benzyl-N-methyl-2-((1-methyl-1H-pyrazol-5-yl)(phenyl)methylthio)ethanamine |
| 34 | N-benzyl-N-methyl-2-((1-methyl-1H-pyrazol-5-yl)(phenyl)methylsulfinyl)ethanamine |
| 35 | N-benzyl-N-methyl-2-((1-methyl-1H-pyrazol-5-yl)(3-methylthiophen-2-yl)methoxy)ethanamine |
| 36 | N-benzyl-2-((2-fluorophenyl)(1-methyl-1H-pyrazol-5-yl)methoxy)-N-methylethanamine |
| 37 | 2-((2-fluorophenyl)(1-methyl-1H-pyrazol-5-yl)methoxy)-N-methyl-N-phenethylethanamine |
| 38 | 2-((2-methoxyphenyl)(1-methyl-1H-pyrazol-5-yl)methoxy)-N-methyl-N-phenethylethanamine |
| 39 | N-benzyl-2-((2-methoxyphenyl)(1-methyl-1H-pyrazol-5-yl)methoxy)-N-methylethanamine |
| 40 | N-benzyl-N-methyl-2-((1-methyl-1H-pyrazol-5-yl)(pyridin-2-yl)methoxy)ethanamine |
| 41 | N-benzyl-N-methyl-2-((1-methyl-1H-pyrazol-5-yl)(thiazol-5-yl)methoxy)ethanamine |
| 42 | N-benzyl-N-methyl-3-((1-methyl-1H-pyrazol-5-yl)(phenyl)methoxy)propan-1-amine |
| 43 | N-(3-fluorobenzyl)-N-methyl-2-((1-methyl-1H-pyrazol-5-yl)(3-methylthiophen-2-yl)methoxy)ethanamine |
| 44 | N-benzyl-N-methyl-3-((1-methyl-1H-pyrazol-5-yl)(thiophen-2-yl)methoxy)propan-1-amine |
| 45 | N-benzyl-N-methyl-2-((1-methyl-1H-pyrazol-5-yl)(pyridin-3-yl)methoxy)ethanamine |
| 46 | N-(3-fluorobenzyl)-N-methyl-2-((1-methyl-1H-pyrazol-5-yl)(pyridin-3-yl)methoxy)ethanamine |
| 47 | N-(3-fluorobenzyl)-2-((2-fluorophenyl)(1-methyl-1H-pyrazol-5-yl)methoxy)-N-methylethanamine |
| 48 | N-(3-fluorobenzyl)-2-((2-methoxyphenyl)(1-methyl-1H-pyrazol-5-yl)methoxy)-N-methylethanamine |
| 49 | N-(3-fluorobenzyl)-N-methyl-2-((1-methyl-1H-pyrazol-5-yl)(thiazol-5-yl)methoxy)ethanamine |
| 50 | N1-benzyl-N1,N2-dimethyl-N2-((1-methyl-1H-pyrazol-5-yl)(phenyl)methyl)ethane-1,2-diamine |
| 51 | 4-((2-(benzyl(methyl)amino)ethoxy)(1-methyl-1H-pyrazol-5-yl)methyl)phenol |
| 52 | 2-((2-(benzyl(methyl)amino)ethoxy)(1-methyl-1H-pyrazol-5-yl)methyl)phenol |
| 53 | 2-((2-((3-fluorobenzyl)(methyl)amino)ethoxy)(1-methyl-1H-pyrazol-5-yl)methyl)phenol | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I), is a compound wherein W is —O— the compound being exemplified in examples 1 to 32 and 35 to 53;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I), is a compound wherein n is 1, X is a bond and $R_2$ is substituted or unsubstituted phenyl, the compound being exemplified in examples 1, 5, 6, 8 to 10, 12 to 18, 21 to 31, 33 to 36, 39 to 53;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I), is a compound wherein n is 1, X is a bond, $R_1$ is substituted or unsubstituted phenyl and $R_2$ is substituted or unsubstituted phenyl, the compound being exemplified in examples 6, 8 to 10, 13, 16, 17, 21 to 27, 29, 33, 34, 36, 39, 42, 47, 48, 50 to 53;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I), is a compound wherein n is 1, X is a bond, $R_1$ is substituted or unsubstituted thiophen and $R_2$ is substituted or unsubstituted phenyl, the compound being exemplified in examples 1. 5, 12, 14, 15, 18, 28, 30, 31, 35, 43 and 44;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I) is a compound wherein
n is 1, the compound being exemplified in examples 1 to 3, 5, 6, 8 to 10, 12 to 18, 21 to 31, 33 to 36 and 39 to 53;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I) is a compound wherein
n is 2, the compound being exemplified in examples 4, 7, 11, 19, 20, 32, 37 and 38;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I) is a compound wherein
m is 1, the compound being exemplified in examples 1 to 41, 43 and 45 to 53;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I) is a compound wherein
m is 2, the compound being exemplified in examples 42 and 44;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I)
$R_1$ is substituted or unsubstituted cycloalkyl, substituted or unsubstituted aryl, or substituted or unsubstituted heterocyclyl;
wherein said cycloalkyl, aryl or heterocyclyl in $R_1$, if substituted, being substituted with one or more substituent/s selected from halogen, —$R_8$, —$OR_8$, —$NO_2$, —$NR_8R_{8'''}$, $NR_8C(O)R_{8'}$, —$NR_8S(O)_2R_{8'}$, —$S(O)_2NR_8$ $R_{8'}$, —$NR_8C(O)NR_8R_{8''}$, —$SR_8$, —$S(O)R_8$, $S(O)_2$ $R_8$, —CN, haloalkyl, haloalkoxy, —$C(O)OR_8$, —$C(O)NR_8R_{8'}$, —$OCH_2CH_2OH$, —$NR_8S(O)_2NR_8R_{8''}$ and $C(CH_3)_2OR_8$;
wherein $R_8$, $R_{8'}$ and $R_{8''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl or unsubstituted alkylaryl, unsubstituted cycloalkyl or unsubstituted alkylcycloalkyl, unsubstituted heterocyclyl and unsubstituted alkyheterocylcyl;
and wherein $R_{8'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I),
$R_2$ is substituted or unsubstituted cycloalkyl, substituted or unsubstituted aryl, or substituted or unsubstituted heteroaryl;
wherein said cycloalkyl, aryl or heteroaryl in $R_2$, if substituted, is substituted with one or more substituent/s selected from halogen, —$R_9$, —$OR_9$, —$NO_2$, —$NR_9R_{9'''}$, $NR_9C(O)R_{9'}$, —$NR_9S(O)_2R_{9'}$, —$S(O)_2NR_9$ $R_{9'}$, —$NR_9C(O)NR_9R_{9''}$, —$SR_9$, —$S(O)R_9$, $S(O)_2$ $R_9$, —CN, haloalkyl, haloalkoxy, —$C(O)OR_9$, —$C(O)NR_9R_{9'}$, —$OCH_2CH_2OH$, —$NR_9S(O)_2NR_9R_{9''}$ and $C(CH_3)_2OR_9$;
wherein $R_9$, $R_{9'}$ and $R_{9''}$ are independently selected from hydrogen, unsubstituted $C_{1-6}$ alkyl, unsubstituted $C_{2-6}$ alkenyl, and unsubstituted $C_{2-6}$ alkynyl;
and wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I),
$R_2$ is substituted or unsubstituted cycloalkyl, substituted or unsubstituted aryl, or substituted or unsubstituted heterocyclyl;
wherein said cycloalkyl, aryl or heterocyclyl in $R_2$, if substituted, is substituted with one or more substituent/s selected from halogen, —$R_9$, —$OR_9$, —$NO_2$, —$NR_9R_{9'''}$, $NR_9C(O)R_{9'}$, —$NR_9S(O)_2R_{9'}$, —$S(O)_2NR_9$ $R_{9'}$, —$NR_9C(O)NR_9R_{9''}$, —$SR_9$, —$S(O)R_9$, $S(O)_2$ $R_9$, —CN, haloalkyl, haloalkoxy, —$C(O)NR_9R_{9'}$, —$OCH_2CH_2OH$, —$NR_9S(O)_2NR_9R_{9''}$ and $C(CH_3)_2$ $OR_9$;
wherein $R_9$, $R_{9'}$ and $R_{9''}$ are independently selected from hydrogen, unsubstituted $C_{1-6}$ alkyl, unsubstituted $C_{2-6}$ alkenyl, and unsubstituted $C_{2-6}$ alkynyl;
and wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I),
the alkyl, alkylene or alkynyl, other than those defined in $R_1$ or $R_2$, if substituted, is substituted with one or more substituents selected from —$OR_{13}$, halogen, —CN, haloalkyl, haloalkoxy, —$NR_{13}R_{13'''}$, —$SR_{13}$, —$S(O)R_{13}$, and —$S(O)_2R_{13}$;

wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I), the aryl, heterocyclyl or cycloalkyl, also in alkylaryl, alkylcycloalkyl and alkylheterocyclyl, other than those defined in $R_1$ or $R_2$, if substituted, is substituted with one or more substituents selected from halogen, —$R_{14}$, —$OR_{14}$, —$NO_2$, —$NR_{14}R_{14'''}$, $NR_{14}C(O)_{14'}$, —$NR_{14}S(O)_2R_{14'}$, —$S(O)_2NR_{14}R_{14'}$, —$NR_{14}C(O)NR_{14'}R_{14'''}$, —$SR_{14}$, —$S(O)R_{14}$, $S(O)_2R_{14}$, —CN, haloalkyl, haloalkoxy, —$C(O)OR_{14}$, —$C(O)NR_{14}R_{14'}$, —$OCH_2CH_2OH$, —$NR_{14}S(O)_2NR_{14'}R_{14''}$ and $C(CH_3)_2OR_{14}$;

wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl, unsubstituted alkylcycloalkyl, unsubstituted heterocyclyl and unsubstituted alkyheterocylcyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_1$ of any of the previous embodiments, the cycloalkyl, aryl or heterocyclyl in $R_1$, if substituted, being substituted with one or more substituent/s selected from halogen, —$R_8$, —$OR_8$, —$NO_2$, —$NR_8R_{8'''}$, $NR_8C(O)R_{8'}$, —$NR_8S(O)_2R_{8'}$, —$S(O)_2NR_8 R_{8'}$, —$NR_8C(O)NR_{8'}R_{8'''}$, —$SR_8$, —$S(O)R_8$, $S(O)_2 R_8$, —CN, haloalkyl, haloalkoxy, —$C(O)OR_8$, —$C(O)NR_8R_{8'}$, —$OCH_2CH_2OH$, —$NR_8S(O)_2NR_{8'}R_{8''}$ and $C(CH_3)_2OR_8$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_1$ of any of the previous embodiments, the cycloalkyl or heterocyclyl in $R_1$, also in alkylcycloalkyl and alkylheterocyclyl, if substituted, is substituted with

or =O;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the previous embodiments, the cycloalkyl, aryl or heteroaryl in $R_2$, if substituted, is substituted with one or more substituent/s selected from halogen, —$R_9$, —$OR_9$, —$NO_2$, —$NR_9R_{9'''}$, $NR_9C(O)R_{9'}$, —$NR_9S(O)_2R_{9'}$, —$S(O)_2NR_9R_{9'}$, —$NR_9C(O)NR_9R_{9'''}$, —$SR_9$, —$S(O)R_9$, $S(O)_2R_9$, —CN, haloalkyl, haloalkoxy, —$C(O)OR_9$, —$C(O)NR_9R_{9'}$, —$OCH_2CH_2OH$, —$NR_9S(O)_2 NR_{9'}R_{9''}$ and $C(CH_3)_2OR_9$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the previous embodiments, the cycloalkyl, aryl or heterocyclyl in $R_2$, if substituted, is substituted with one or more substituent/s selected from halogen, —$R_9$, —$OR_9$, —$NO_2$, —$NR_9R_{9'''}$, $NR_9C(O)R_{9'}$, —$NR_9S(O)_2R_{9'}$, —$S(O)_2NR_9R_{9'}$, —$NR_9C(O)NR_9R_{9'''}$, —$SR_9$, —$S(O)R_9$, $S(O)_2R_9$, —CN, haloalkyl, haloalkoxy, —$C(O)NR_9R_{9'}$, —$OCH_2CH_2OH$, —$NR_9S(O)_2NR_9R_{9''}$ and $C(CH_3)_2OR_9$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the previous embodiments, additionally, cycloalkyl in $R_2$, if substituted, is substituted with

or =O;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to alkyls other than those defined in $R_1$ or $R_2$ of any of the previous embodiments, the alkyl, alkylene or alkynyl, other than those defined in $R_1$ or $R_2$, if substituted, is substituted with one or more substituents selected from —OR$_{13}$, halogen, —CN, haloalkyl, haloalkoxy, —NR$_{13}$R$_{13'''}$, —SR$_{13}$, —S(O)R$_{13}$, and —S(O)$_2$R$_{13}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to alkyls other than those defined in R$_1$ or R$_2$ of any of the previous embodiments, the aryl, heterocyclyl or cycloalkyl, also in alkylaryl, alkylcycloalkyl and alkylheterocyclyl, other than those defined in R$_1$ or R$_2$, if substituted, is substituted with one or more substituents selected from halogen, —R$_{14}$, —OR$_{14}$, —NO$_2$, —NR$_{14}$R$_{14'''}$, NR$_{14}$C(O)R$_{14'}$, —NR$_{14}$S(O)$_2$R$_{14'}$, —S(O)$_2$NR$_{14}$R$_{14'}$, —NR$_{14}$C(O)NR$_{14'}$R$_{14'''}$, —SR$_{14}$, —S(O)R$_{14}$, S(O)$_2$R$_{14}$, —CN, haloalkyl, haloalkoxy, —C(O)OR$_{14}$, —C(O)NR$_{14}$R$_{14'}$, —OCH$_2$CH$_2$OH, —NR$_{14}$S(O)$_2$NR$_{14'}$R$_{14'''}$ and C(CH$_3$)$_2$OR$_{14}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I), the halogen is fluorine, chlorine, iodine or bromine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a most preferred embodiment of the compound according to the invention of general Formula (I)

the halogen is fluorine or chlorine optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I), the haloalkyl is —CF$_3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the compound according to the invention of general Formula (I), the haloalkoxy is —OCF$_3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

As this invention is aimed at providing a compound or a chemically related series of compounds which act as dual ligands of the σ$_1$ receptor and the μ-opiod receptor it is a very preferred embodiment in which the compounds are selected which act as dual ligands of the σ$_1$ receptor and the μ-opiod receptor and especially compounds which have a binding expressed as K$_i$ which is preferably <1000 nM for both receptors, more preferably <500 nM, even more preferably <100 nM.

In the following the phrase "compound of the invention" is used. This is to be understood as any compound according to the invention as described above according to general Formula (I).

The compounds of the invention represented by the above described Formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

In general the processes are described below in the experimental part. The starting materials are commercially available or can be prepared by conventional methods.

A preferred aspect of the invention is also a process for the production of a compound according to formula I, following schemes 1, 2 or 3.

A preferred embodiment of the invention is a process for the production of a compound according to Formula (I), wherein m, n, R$_1$, R$_2$, R$_3$, R$_4$, R$_{4'}$, R$_5$, R$_6$, R$_{6'}$ and X have the meanings defined above, and W is —O—, following scheme 1.

In a particular embodiment there is a process for the production of a compound according to Formula (I),

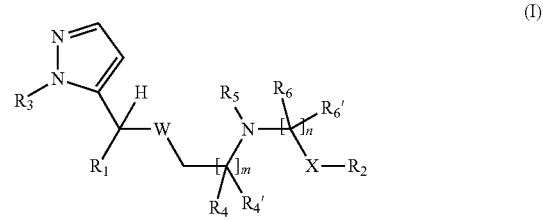

(I)

said process comprises alkylating a compound of Formula (XIII)

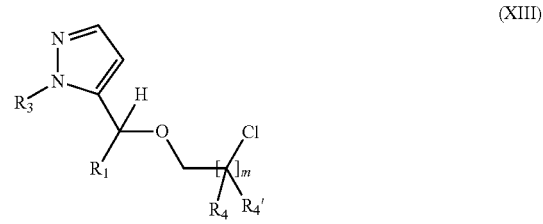

(XIII)

with a compound of Formula (XIV)

(XIV)

wherein m, n, R$_1$, R$_2$, R$_3$, R$_4$, R$_{4'}$, R$_5$, R$_6$, R$_{6'}$ and X have the meaning as defined above in the description and W is —O—.

In another embodiment there is a process for the production of a compound according to Formula (I),

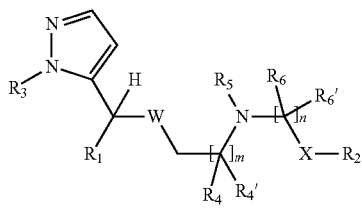
(I)

said process comprises reacting a carbinol of Formula (IIa)

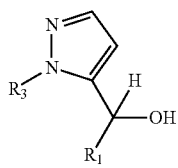
(IIa)

with a compound of general Formula (XV)

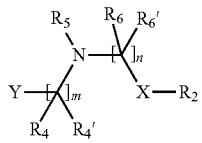
(XV)

wherein m, n, $R_1$, $R_2$, $R_3$, $R_4$, $R_{4'}$, $R_5$, $R_6$, $R_{6'}$ and X have the meaning as defined above in the description, W is —O—, and Y is a hydroxyl group or a leaving group such as chloro, bromo, mesylate or tosylate.

In another embodiment there is a process for the production of a compound according to Formula (I),

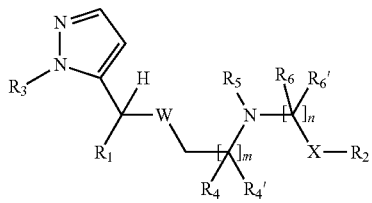
(I)

said process comprises reacting a compound of general Formula (V)

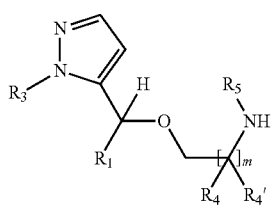
(V)

with a suitable reagent of Formula (VIa) or (VIb)

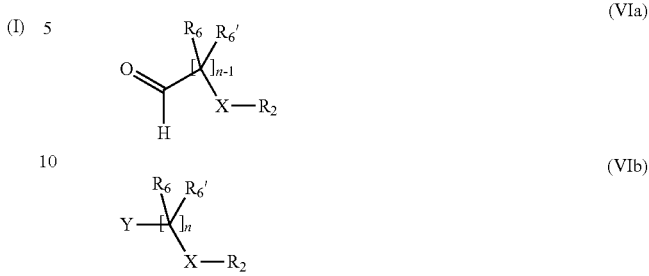
(VIa)

(VIb)

wherein m, n, $R_1$, $R_2$, $R_3$, $R_4$, $R_{4'}$, $R_5$, $R_6$, $R_{6'}$ and X have the meaning as defined above in the description, W is —O— and Y is a hydroxyl group or a leaving group such as chloro, bromo, mesylate or tosylate.

In another embodiment there is a process for the production of a compound according to Formula (I),

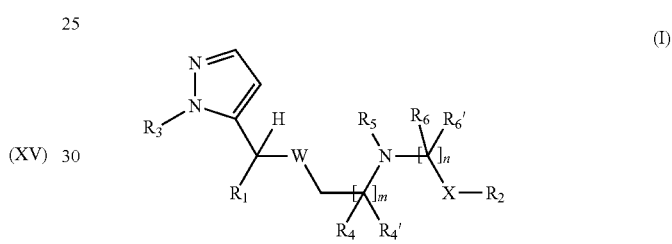
(I)

said process comprises the reduction of a compound of Formula (VIII)

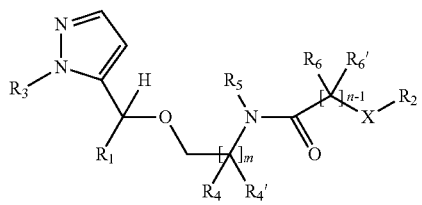
(VIII)

wherein m, n, $R_1$, $R_2$, $R_3$, $R_4$, $R_{4'}$, $R_5$, $R_6$, $R_{6'}$ and X have the meaning as defined above in the description and W is —O—.

In a particular embodiment a compound of Formula (IIa),

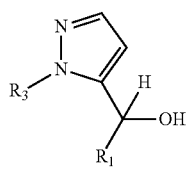
(IIa)

wherein $R_1$ and $R_3$ have the meaning as defined above in the description, is used for the preparation of compounds of Formula (I) wherein W is —O—.

In another particular embodiment a compound of Formula (III),

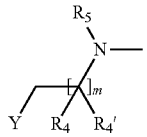

(III)

wherein m, $R_4$, $R_{4'}$ and $R_5$, have the meaning as defined above in the description, and Y is a hydroxyl group or a leaving group such as chloro, bromo, mesylate or tosylate, is used for the preparation of compounds of Formula (I) wherein W is —O—.

In a particular embodiment a compound of Formula (IV)

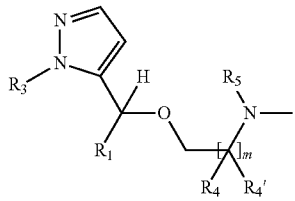

(IV)

wherein m, $R_1$, $R_3$, $R_4$, $R_{4'}$ and $R_5$ have the meaning as defined above in the description, is used for the preparation of compounds of Formula (I) wherein W is —O—

In a particular embodiment a compound of Formula (V)

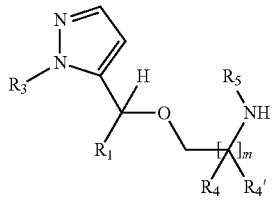

(V)

wherein m, $R_1$, $R_3$, $R_4$, $R_{4'}$, and $R_5$ have the meaning as defined above in the description, is used for the preparation of compounds of Formula (I) wherein W is —O—

In a particular embodiment a compound of Formula (VIa)

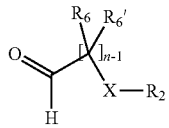

(VIa)

wherein n, $R_2$, $R_6$, $R_{6'}$ and X have the meaning as defined above in the description, is used for the preparation of compounds of Formula (I) wherein W is —O—.

In a particular embodiment a compound of Formula (VIb)

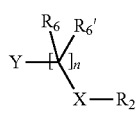

(VIb)

wherein n, $R_2$, $R_6$, $R_{6'}$ and X have the meaning as defined above in the description, and Y is a hydroxyl group or a leaving group such as chloro, bromo, mesylate or tosylate, is used for the preparation of compounds of Formula (I) wherein W is —O—.

In a particular embodiment a compound of Formula (VII)

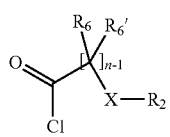

(VII)

wherein n, $R_2$, $R_6$, $R_{6'}$ and X have the meaning as defined above in the description, is used for the preparation of compounds of Formula (I) wherein W is —O—.

In a particular embodiment a compound of Formula (VIII)

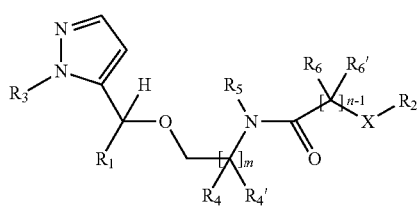

(VIII)

wherein m, n, $R_1$, $R_2$, $R_3$, $R_4$, $R_{4'}$, $R_5$, $R_6$, $R_{6'}$ and X have the meaning as defined above in the description, is used for the preparation of compounds of Formula (I) wherein W is —O—.

In a particular embodiment a compound of Formula (IX)

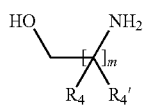

(IX)

wherein m, $R_4$ and $R_{4'}$ have the meaning as defined above in the description, is used for the preparation of compounds of Formula (I) wherein W is —O—.

In a particular embodiment a compound of Formula (X)

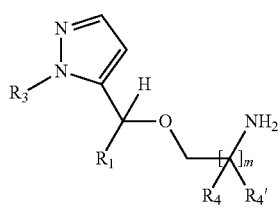

(X)

wherein m, $R_1$, $R_3$, $R_4$ and $R_{4'}$ have the meaning as defined above in the description, is used for the preparation of compounds of Formula (I) wherein W is —O—.

In a particular embodiment a compound of Formula (XI)

$$R_5=O \qquad (XI)$$

wherein $R_5$ has the meaning as defined above in the description, is used for the preparation of compounds of Formula (I) wherein W is —O—.

In a particular embodiment a compound of Formula (XII)

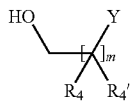

(XII)

wherein m, $R_4$ and $R_{4'}$ have the meaning as defined above in the description, and Y is a hydroxyl group or a leaving group such as chloro, bromo, mesylate or tosylate, is used for the preparation of compounds of Formula (I) wherein W is —O—.

In a particular embodiment a compound of Formula (XIII)

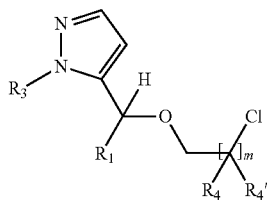

(XIII)

wherein m, $R_1$, $R_3$, $R_4$ and $R_{4'}$ have the meaning as defined above in the description, is used for the preparation of compounds of Formula (I) wherein W is —O—.

In a particular embodiment a compound of Formula (XIV)

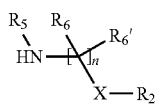

(XIV)

wherein n, $R_2$, $R_5$, $R_6$, $R_{6'}$ and X have the meaning as defined above in the description, is used for the preparation of compounds of Formula (I) wherein W is —O—

In a particular embodiment a compound of Formula (XV)

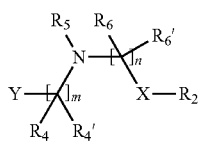

(XV)

wherein m, n, $R_2$, $R_4$, $R_{4'}$, $R_5$, $R_6$, $R_{6'}$ and X have the meaning as defined above in the description, and Y is a hydroxyl group or a leaving group such as chloro, bromo, mesylate or tosylate, is used for the preparation of compounds of Formula (I) wherein W is —O—.

A preferred embodiment of the invention is a process for the production of a compound according to formula I, wherein m, n, $R_1$, $R_2$, $R_3$, $R_4$, $R_{4'}$, $R_5$, $R_6$, $R_{6'}$ and X have the meanings defined above, and W is —S— or —S(O)—, following scheme 2.

In a particular embodiment there is a process for the production of a compound according to formula I wherein W is —S(O)—,

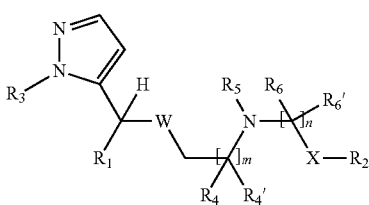

(I)

said process comprises the oxidation of a compound of formula I wherein W is —S—, wherein m, n, $R_1$, $R_2$, $R_3$, $R_4$, $R_{4'}$, $R_5$, $R_6$, $R_{6'}$ and X have the meaning as defined above in the description.

In a particular embodiment there is a process for the production of a compound according to formula I wherein W is —S—,

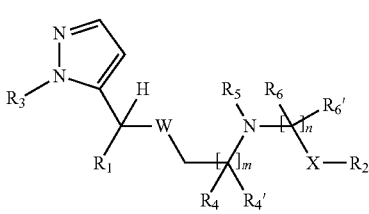

(I)

said process comprises reacting compound of formula IIb

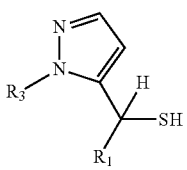

(IIb)

with an alkylating agent of formula XV

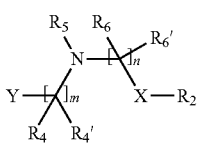

(XV)

wherein m, n, $R_1$, $R_2$, $R_3$, $R_4$, $R_{4'}$, $R_5$, $R_6$, $R_{6'}$ and X have the meaning as defined above in the description, and Y is a hydroxyl group or a leaving group such as chloro, bromo, mesylate or tosylate.

In a particular embodiment a compound of Formula (IIa),

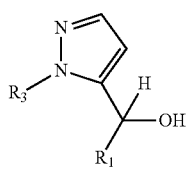

wherein $R_1$ and $R_3$ have the meaning as defined above in the description, is used for the preparation of compounds of Formula (I) wherein W is —S— or —S(O)—

In a particular embodiment a compound of Formula (IIb),

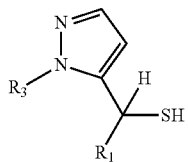

wherein $R_1$ and $R_3$ have the meaning as defined above in the description, is used for the preparation of compounds of Formula (I) wherein W is —S— or —S(O)—

In a particular embodiment a compound of Formula (XV),

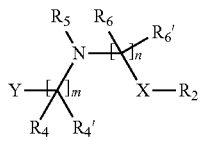

wherein m, n, $R_2$, $R_4$, $R_{4'}$, $R_5$, $R_6$, $R_{6'}$ and X have the meaning as defined above in the description, and Y is a hydroxyl group or a leaving group such as chloro, bromo, mesylate or tosylate, is used for the preparation of compounds of Formula (I) wherein W is —S— or —S(O)—.

In a particular embodiment a compound of Formula (I), wherein W is —S—,

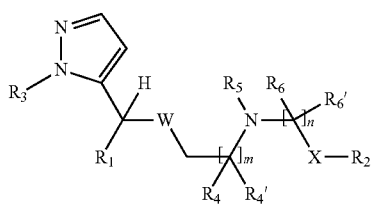

is used for the preparation of compounds of Formula (I) wherein W is —S(O)—,
wherein m, n, $R_1$, $R_2$, $R_3$, $R_4$, $R_{4'}$, $R_5$, $R_6$, $R_{6'}$ and X have the meaning as defined above in the description.

A preferred embodiment of the invention is a process for the production of a compound according to Formula (I), wherein m, n, $R_1$, $R_2$, $R_3$, $R_4$, $R_{4'}$, $R_5$, $R_6$, $R_{6'}$ and X have the meaning as defined above, and W is —$NR_w$—, following scheme 3.

In a particular embodiment there is a process for the production of a compound according to Formula (I)

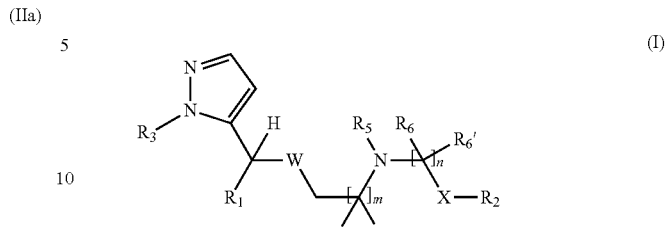

said process comprises treating a compound of general Formula (XIX)

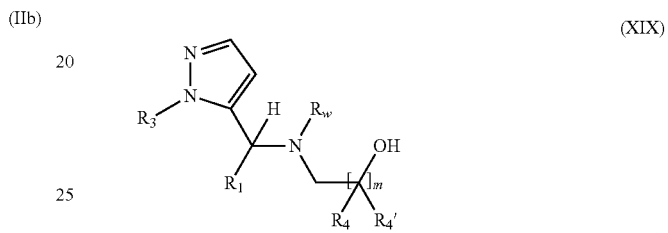

with thionyl chloride and subsequently reacting of the alkyl chloride intermediate with an amine compound of Formula (XIV).

wherein m, n, $R_1$, $R_2$, $R_3$, $R_4$, $R_{4'}$, $R_5$, $R_6$, $R_{6'}$ and X have the meaning as defined above in the description, and W is —$NR_w$—.

In a particular embodiment a compound of Formula (IIa),

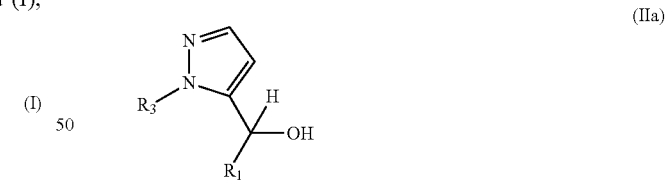

wherein $R_1$ and $R_3$ have the meaning as defined above in the description, is used for the preparation of compounds of Formula (I) wherein W is —$NR_w$—.

In a particular embodiment a compound of Formula (XVI),

wherein m, $R_4$ and $R_{4'}$ have the meaning as defined above in the description, is used for the preparation of compounds of Formula (I) wherein W is —$NR_w$—.

In a particular embodiment a compound of Formula (XVII),

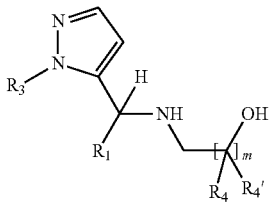

(XVII)

wherein m, $R_1$, $R_3$, $R_4$ and $R_{4'}$ have the meaning as defined above in the description, is used for the preparation of compounds of Formula (I) wherein W is —$NR_w$—.

In a particular embodiment a compound of Formula (XVIII), $R_wZ$   (XVIII)

wherein $R_w$ has the meaning as defined above in the description, and wherein Z is a =O group or a halogen atom, is used for the preparation of compounds of Formula (I) wherein W is —$NR_w$—.

In a particular embodiment a compound of Formula (XIX),

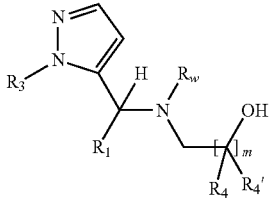

(XIX)

wherein m, $R_w$, $R_1$, $R_3$, $R_4$ and $R_{4'}$ have the meaning as defined above in the description, is used for the preparation of compounds of Formula (I) wherein W is —$NR_w$—.

In a particular embodiment a compound of Formula (XIV),

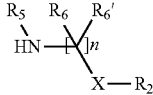

(XIV)

wherein n, $R_2$, $R_5$, $R_6$, $R_{6'}$ and X have the meaning as defined above in the description, is used for the preparation of compounds of Formula (I) wherein W is —$NR_w$—.

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formula I or a pharmaceutically acceptable salt or stereoisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound of the invention or a pharmaceutically acceptable salt or isomer thereof in the manufacture of a medicament.

Another aspect of the invention refers to a compound of the invention according as described above according to general formula I, or a pharmaceutically acceptable salt or isomer thereof, for use as a medicament for the treatment of pain. Preferably the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia.

Another aspect of the invention refers to the use of a compound of the invention in the manufacture of a medicament for the treatment or prophylaxis of pain.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, cancer pain, migraine, inflammatory pain, acute pain or neuropathic pain, allodynia or hyperalgesia, whereas this could also include mechanical allodynia or thermal hyperalgesia.

The present invention is illustrated below with the aid of examples. These illustrations are given solely by way of example and do not limit the general spirit of the present inventionEquipment of the Synthesis and Analysis

EXAMPLES

General Experimental Part (Methods and

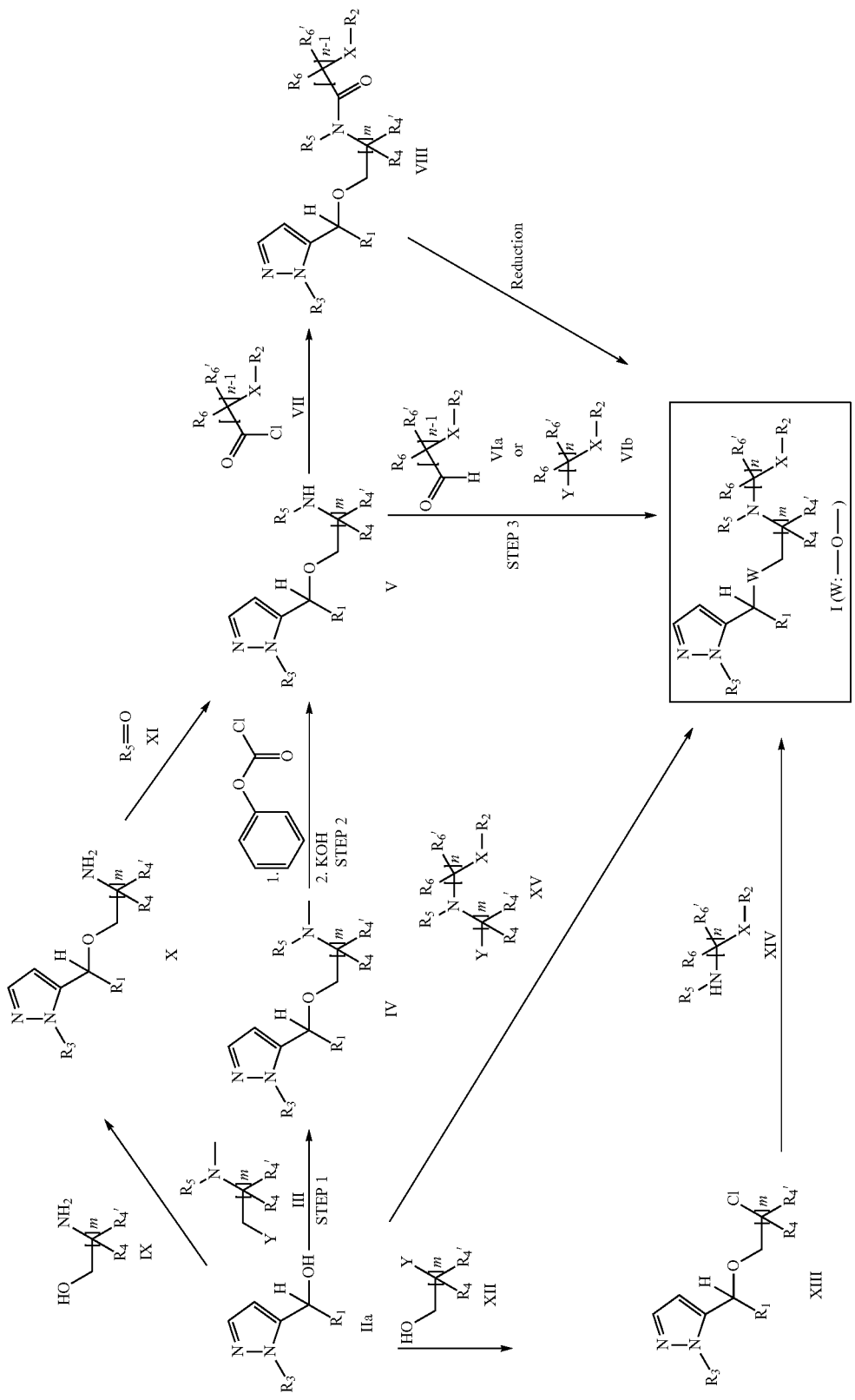
Scheme 1

A 3-step process is described in Scheme 1 for the preparation of compounds of general formula I, wherein $R_1$, $R_2$, $R_3$, $R_4$, $R_{4'}$, $R_5$, $R_6$, $R_{6'}$ and X have the meanings defined above, and W is —O—.

Where Y is a hydroxyl group or a leaving group such as chloro, bromo, mesylate or tosylate.

This process is carried out as described below:

Step 1: A compound of formula IV is prepared by treating a carbinol of general formula IIa with an alkylating agent of general formula III. The alkylation reaction is carried out in the presence of a phase transfer catalyst such as tetrabutylammonium bromide and an inorganic base such as KOH or NaOH; in a suitable solvent such as mixtures of water and toluene, acetonitrile, dichloromethane or 1,4-dioxane, preferably in toluene; at a suitable temperature comprised between room temperature and the reflux temperature, preferably heating, or alternatively in a microwave reactor.

Step 2: A compound of formula V is prepared by reaction of a compound of formula IV with phenyl chloroformate, in a suitable solvent such as dichloromethane, in the presence of an inorganic base such as $K_2CO_3$ or $Cs_2CO_3$, at a suitable temperature comprised between room temperature and the reflux temperature, preferably at room temperature, followed by hydrolysis of the carbamate intermediate thus obtained with a suitable inorganic base such as NaOH or KOH, in a suitable solvent such as ethylene glycol, at a suitable temperature comprised between 80 and 160° C.

An alternative two step procedure can be effected for the transformation of a compound of formula IIa to a compound of formula V as described in scheme 1. In this alternative method, a compound of general formula X is prepared by reacting a carbinol of general formula IIa with an alcohol of general formula IX in the presence of p-toluensulfonic acid, in a suitable solvent such as toluene at reflux temperature.

In a second step, compound of general formula V is obtained by reductive amination reaction between a compound of general formula X and a compound of general formula XI in the presence of a reductive reagent, preferably $NaBH_4$ in AcOH, at a suitable temperature comprised between room temperature and the reflux temperature.

Step 3: The compounds of general formula I are prepared by reacting a compound of general formula V with a suitable reagent of formula VIa-b, using different conditions depending on the reagent nature. Thus:

The reductive amination between a compound of formula V and a compound of formula VIa, is carried out in the presence of a reductive reagent, preferably sodium triacetoxyborohydride, in an aprotic solvent, preferably tetrahydrofuran or dichloroethane, at a suitable temperature comprised between room temperature and the reflux temperature, preferably in a microwave reactor.

The alkylation reaction between a compound of formula V and a compound of formula VIb is carried out in a suitable solvent, such as acetonitrile, dichloromethane, 1,4-dioxane or dimethylformamide, preferably in acetonitrile; in the presence of an inorganic base such as $K_2CO_3$ or $Cs_2CO_3$, or an organic base such as triethylamine or diisopropylethylamine, preferably $K_2CO_3$; at a suitable temperature comprised between room temperature and the reflux temperature, preferably heating, or alternatively, the reactions can be carried out in a microwave reactor. Additionally, an activating agent such as NaI can be used.

Alternatively, the transformation of a compound of formula V to a compound of formula I, wherein W is —O—, can be effected in a two step procedure, involving acylation of V with an acid chloride of formula VII to give a compound of formula VIII, which is then reduced. The acylation reaction can be carried out using DIPEA in a suitable solvent such as dichloromethane at a suitable temperature, preferably room temperature. The reduction reaction can be effected with a reducing agent such as aluminium hydride, in a suitable solvent such as tetrahydrofuran, at a suitable temperature comprised between 0° C. and room temperature, preferably at 0° C.

The process described by steps 1 to 3 represents the most general route for the preparation of compounds of formula I. Additionally, the compounds of general formula I, wherein W is —O—, can be prepared in a two step procedure, involving reaction of compound of formula IIa with an alcohol of formula XII, in the presence of p-toluensulfonic acid, in a suitable solvent such as toluene at reflux temperature to give a compound of formula XIII. In a second step, a compound of formula XIII is alkylated with an amine compound of formula XIV, in a suitable solvent, preferably in dimethylformamide; in the presence of an inorganic base, preferably $K_2CO_3$; at a suitable temperature comprised between room temperature and the reflux temperature, preferably reflux temperature Additionally, the compounds of general formula I, wherein W is —O—, can be obtained in a single step procedure, involving reaction of carbinol IIa with a compound of general formula XV using different conditions depending on the reagent nature. Thus:

The Williamson ether synthesis reaction between a compound of formula IIa and a organohalide of formula XV, where Y is a leaving group, is carried out in the presence of a phase transfer catalyst such as tetrabutylammonium bromide and an inorganic base such as KOH or NaOH; in a suitable solvent such as mixtures of water and toluene, acetonitrile, dichloromethane or 1,4-dioxane, preferably in toluene; at a suitable temperature comprised between room temperature and the reflux temperature, preferably at reflux temperature.

The dehydration reaction between a compound of formula IIa and an alcohol of formula XV where Y is a hydroxyl group, is carried out in the presence of $H_2SO_4$ in a suitable solvent such as toluene, at reflux temperature.

A process for the preparation of compounds of general formula I, wherein $R_1$, $R_2$, $R_3$, $R_4$, $R_{4'}$, $R_5$, $R_6$, $R_{6'}$ and X have the meanings as defined above, and W is —S— or —S(O) is described in Scheme 2:

Scheme 2

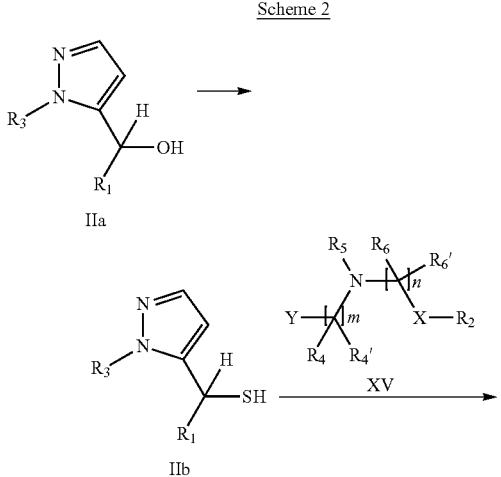

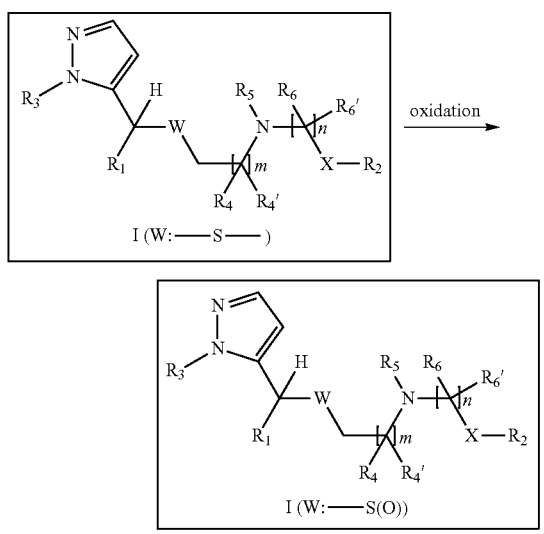

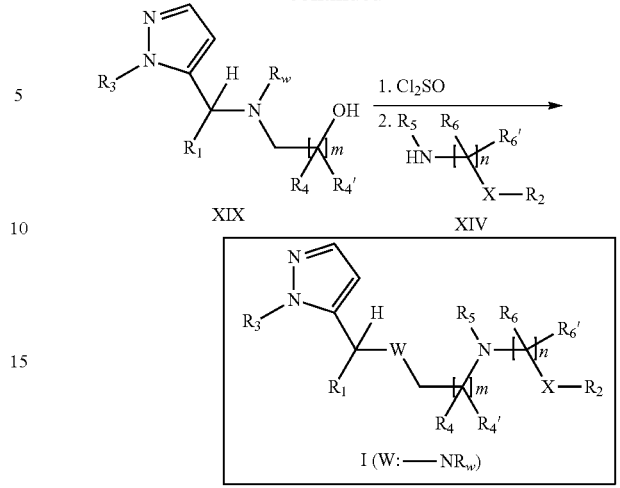

A compound of formula XVII is obtained by treating a compound of formula IIa with hydrobromic acid and subsequently reaction of the bromide intermediate with amine-alcohol compounds of formula XVI. The alkylation reaction is carried out in a suitable solvent, such as acetonitrile, dichloromethane, 1,4-dioxane or dimethylformamide or, preferably, in the absence of solvent, at a suitable temperature comprised between room temperature and the reflux temperature, preferably at 50° C.

A compound of formula XIX is prepared by reaction of a compound of formula XVII with a compound of formula XVIII, where Z is a =O group or a halogen atom. When Z is a =O group the reductive amination reaction is carried out in similar conditions than the ones described in step 3 (scheme 1). When Z is a halogen atom the reaction is carried out under alkylation or acylation conditions such as the ones described in step 3 (scheme 1).

The compounds of general formula I, wherein W is —NR$_w$ are obtained by treating a compound of general formula XIX with thionyl chloride and subsequently reaction of the alkyl chloride intermediate with amine compound of formula XIV. The alkylation reaction is carried out in the presence of an inorganic base, preferably K$_2$CO$_3$; in a suitable solvent such as acetonitrile, at a suitable temperature, preferably reflux temperature.

A compound of formula IIb is prepared by treating a carbinol of formula IIa with Lawesson's reagent in a suitable solvent such as toluene, at a suitable temperature comprised between room temperature and the reflux temperature, preferably at 50° C.

Compounds of general formula I, wherein W is —S— are prepared by treating compound of formula IIb with alkylating agents of formula XV where Y is a suitable leaving group. The alkylation reaction is carried out in the presence an inorganic aqueous base such as KOH or NaOH; in a suitable solvent such as ethanol, at a suitable temperature, preferably room temperature.

Compounds of general formula I, wherein W is —S(O) are prepared by an oxidation reaction of compounds of general formula I, wherein W is —S—, by treatment with a suitable oxidizing agent, such as hydrogen peroxide in a suitable solvent, such as methanol at room temperature.

A process for the preparation of compounds of general formula I, wherein R$_1$, R$_2$, R$_3$, R$_4$, R$_4'$, R$_5$, R$_6$, R$_6'$ and X have the meanings as defined above, and W is —NR$_w$ is described in Scheme 3:

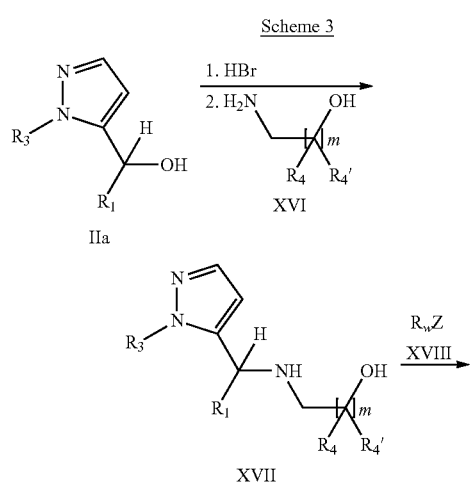

EXAMPLES

Intermediates and Examples

The following abbreviations are used in the examples:
ACN: acetonitrile
AcOH: acetic acid
Boc: tert-butoxycarbonyl
DCM: dichloromethane
DCE: 1,2-dichloroethane
DIPEA: diisopropylethylamine
DMF: dimethylformamide
EDC: N-(3-Dimethylaminopropyl)-N-ethylcarbodiimide
EtOH: ethanol
h: hour/s
HPLC: high performance liquid chromatography
MeOH: methanol
MS: mass spectrometry
Min.: minutes Ret.: retention time r.t.: room temperature THF: tetrahydrofuran The following methods were used to determine the HPLC-MS spectra:

A: Column: XBridge C18 4.6×50 mm 2.5 μm; flow rate: 2 mL/min; temperature: 35° C., A: NH₄HCO₃ 10 mM; B: ACN; gradient: 0.3 min in 98% A, 98% A to 5% A in 4 min, 1.5 min in 5% A, 5% A to 98% A in 0.5 min, 1 min in 98% A.

B: Column Acquity BEH C18 2.1×50 mm, 1.7 μm; flow rate 0.61 mL/min; temperature: 35° C., A: NH₄HCO₃ 10 mM; B: ACN; gradient: 0.3 min in 98% A, 98% A to 5% A in 2.52 min, 1.02 min in 5% A, 5% A to 98% A in 0.34 min, 0.57 min in 98% A.

Intermediate 1A. (1-Methyl-1H-pyrazol-5-yl)(3-methylthiophen-2-yl)methanol

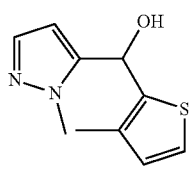

A solution of N-methylpyrazol (4.16 mL, 50 mmol) in anhydrous THF (70 mL) was cooled to −78° C. using a dry ice/acetone bath. After addition of buthyllithium (25 mL, 2M in cyclohexanes, 50 mmol), the reaction mixture was stirred at −78° C. for 30 min. 3-Methyl-2-thiophen carboxaldehyde (5.3 mL, 49 mmol) was then added and the reaction mixture was allowed to reach room temperature and stirred overnight. The solvent was removed in vacuo, and the residue was partioned between water and DCM. The aqueous layer was extracted three times with DCM. The combined organic layers were washed with brine and water, dried over Na₂SO₄, filtered and concentrated. The crude residue was purified by flash chromatography on silica gel, gradient chloroform to MeOH:chloroform (10:90) to give the title compound as a solid (5.6 g, yield 55.3%).

HPLC-MS (Method A): Ret, 2.10 min; ESI⁺-MS m/z, 209.1 (M+1).

This method was used for the preparation of intermediates 1B-I using suitable starting materials:

| INT | Structure | Chemical name | Method | Ret (min) | MS (M + H) |
|---|---|---|---|---|---|
| 1B | | (1-methyl-1H-pyrazol-5-yl)(thiophen-2-yl)methanol. | B | 1.15 | 195 |
| 1C | 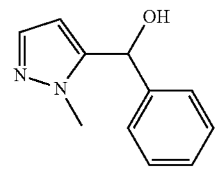 | (1-methyl-1H-pyrazol-5-yl)(phenyl)methanol | B | 1.23 | 189.1 |
| 1D | 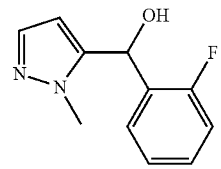 | (2-fluorophenyl)(1-methyl-1H-pyrazol-5-yl)methanol | A | 0.95 | 207.1 |
| 1E | 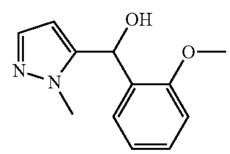 [SMILES: COc1ccccc1C(O)c1ccnn1C] | (2-methoxyphenyl)(1-methyl-1H-pyrazol-5-yl)methanol | A | 1.25 | 219.1 |
| 1F | 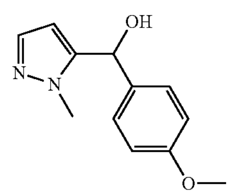 [SMILES: COc1ccc(C(O)c2ccnn2C)cc1] | (4-methoxyphenyl)(1-methyl-1H-pyrazol-5-yl)methanol | B | 1.23 | 219.1 |
| 1G | 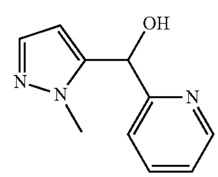 | (1-methyl-1H-pyrazol-5-yl)(pyridin-2-yl)methanol | A | 0.96 | 190.1 |
| 1H | 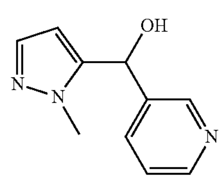 | (1-methyl-1H-pyrazol-5-yl)(pyridin-3-yl)methanol | A | 0.82 | 190.1 |
| 1I | 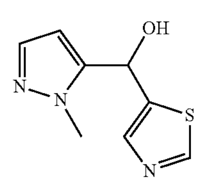 | (1-methyl-1H-pyrazol-5-yl)(thiazol-5-yl)methanol | A | 0.87 | 196 |

Intermediate 1J.
2-(hydroxy(1-methyl-1H-pyrazol-5-yl)methyl)phenol

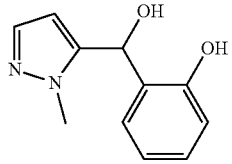

a) (2-Methoxyphenyl)(1-methyl-1H-pyrazol-5-yl) methanone

A mixture of (2-methoxyphenyl)(1-methyl-1H-pyrazol-5-yl)methanol (intermediate 1E, 460 mg, 2.11 mmol) and manganese dioxide (1.8 g, 21 mmol) in chloroform (20 mL) was refluxed overnight. Then, the reaction mixture was filtered through dicalite and washed with chloroform. The combined organic layers were evaporated to dryness to give the title compound as amber oil (420 mg, yield 92%) that was used in the next step without further purification.

HPLC-MS (Method B): Ret, 1.56 min; ESI$^+$-MS m/z, 217.2 (M+1).

b) (2-Hydroxyphenyl)(1-methyl-1H-pyrazol-5-yl) methanone

The compound obtained in the previous step (420 mg, 1.9 mmol) was treated with hydrobromic acid (48% wt in water, 5 mL) and stirred at 80° C. overnight. The reaction mixture was concentrated in vacuo and the crude residue was partioned between water and DCM. The aqueous layer was extracted with DCM (×4) and the organic layer was washed with water. The combined organic layers were dried over Na$_2$SO$_4$, filtered and concentrated to dryness. The resulting brown solid was purified by flash chromatography on silica gel, gradient cyclohexane: ethyl acetate from (90:10) to (80:20) to give the title compound as a yellow solid (230 mg, yield 59%).

HPLC-MS (Method B): Ret, 1.63 min; ESI$^+$-MS m/z, 203.1 (M+1).

c) Title Compound

To a solution of the compound obtained in step b (230 mg, 1.13 mmol) in methanol (8 mL), NaBH$_4$ (130 mg, 3.4 mmol) was added. The reaction mixture was stirred at 50° C. overnight, and then the solvent was evaporated. Water was added and the solution was acidified to pH=6 with acetic acid and extracted with ethyl acetate. The organic phases were combined, washed with water, dried over Na$_2$SO$_4$, filtered and concentrated to dryness to give the title compound as an amber oil (160 mg, yield 94.7%).

HPLC-MS (Method B): Ret, 1.04 min; ESI$^+$-MS m/z, 205.1 (M+1).

A similar method was used for the preparation of intermediate 1K, using intermediate 1F as starting material:

| INT | Structure | Chemical name | Method | Ret (min) | MS (M + H) |
|---|---|---|---|---|---|
| 1K | 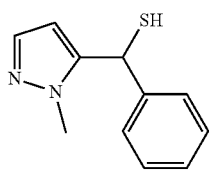 | 4-(hydroxy(1-methyl-1H-pyrazol-5-yl)methyl)phenol | B | 0.86 | 205.1 |

Intermediate 1L.
(1-Methyl-1H-pyrazol-5-yl)(phenyl)methanethiol (1-Methyl-1H-pyrazol-5-yl)(phenyl)methanol (intermediate 1C, 5.6 g, 30 mmol) was suspended in toluene (130 mL) and Lawesson's reagent (6.07 g, 15 mmol) was added. The reaction mixture was stirred at 50° C. during 2 h, and then 20 mL of water was added and the resulting mixture was cooled to room temperature and stirred for 1 h. The organic layer was separated and washed with NaHCO$_3$ saturated aqueous solution and brine, dried over Na$_2$SO$_4$, filtered and concentrated to dryness to give the title compound as a crude product (1.28 g, yield 8.5%) that was used for the synthesis of example 26 without further purification.

HPLC-MS (Method A): Ret, 3.82 min; ESI$^+$-MS m/z, 205.3 (M+1).

Intermediate 1M. (R)-(1-methyl-1H-pyrazol-5-yl)(phenyl)methanol

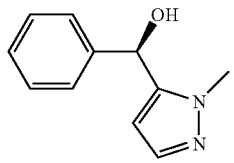

To a stirred solution of (R)-2-methyl-CBS-oxazaborolidine (1M in toluene, 7.5 mL, 7.5 mmol) under argon cooled to −10° C., a solution of catecholborane (1M in THF, 100 mL, 100 mmol) was slowly added. To the mixture was then added a solution of (1-methyl-1H-pyrazol-5-yl)(phenyl)methanone (prepared from intermediate 1C, as described for intermediate 1J, step a, 9.3 g, 50 mmol) in dry toluene (100 mL) and the reaction was stirred 1 h at −15° C. and 20 h at r.t. MeOH (10 mL) was added carefully with stirring for 2 h. The mixture was concentrated under vacuo to 100 mL, washed successively with water, HCl 1N and brine, dried over $Na_2SO_4$, filtered and concentrated to give an oil that was purified by flash chromatography on silica gel, eluents ethyl acetate:petroleum ether (7:3) to give the title compound (7.82 g, 83% yield, 98% ee).

HPLC-MS (Method B): Ret, 1.23 min; $ESI^+$-MS m/z, 189.1 (M+1).

A similar method was used for the preparation of intermediates 1N-R

| INT | Structure | Chemical name | Method | Ret (min) | MS (M + H) |
|---|---|---|---|---|---|
| 1N | 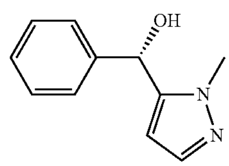 | (S)-(1-methyl-1H-pyrazol-5-yl)(phenyl)methanol | B | 1.23 | 189.1 |
| 1O | 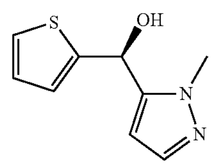 | (S)-(1-methyl-1H-pyrazol-5-yl)(thiophen-2-yl)methanol | B | 1.15 | 195 |
| 1P | 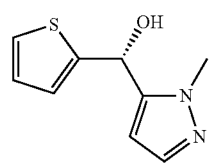 | (R)-(1-methyl-1H-pyrazol-5-yl)(thiophen-2-yl)methanol | B | 1.15 | 195 |
| 1Q | 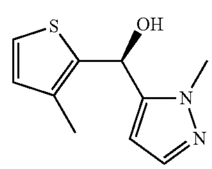 | (S)-(1-methyl-1H-pyrazol-5-yl)(3-methylthiophen-2-yl)methanol | A | 2.11 | 209.1 |
| 1R | 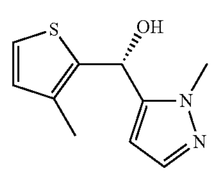 | (R)-(1-methyl-1H-pyrazol-5-yl)(3-methylthiophen-2-yl)methanol | A | 2.11 | 209.1 |

Intermediate 2A. N-methyl-2-(1-methyl-1H-pyrazol-5-yl)(thiophen-2-yl)methoxy)ethanamine

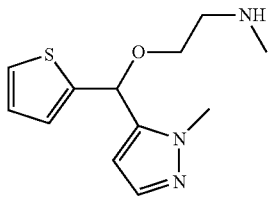 [SMILES: CNCCOC(c1cccs1)c1ccnn1C]

a) N,N-dimethyl-2-((1-methyl-1H-pyrazol-5-yl)(thiophen-2-yl)methoxy)ethanamine A mixture of (1-methyl-1H-pyrazol-5-yl)(thiophen-2-yl)methanol (intermediate 1B, 18 g, 92.7 mmol), 2-chloro-N,N-dimethylethanamine hydrochloride (26.7 g, 188 mmol), tetrabutylammonium bromide (1 g, 3 mmol) in NaOH (50% in water, 150 mL) and toluene (300 mL) was refluxed for 24 h. Then, it was cooled and the organic layer was separated, washed with water, dried over $Na_2SO_4$, filtered and concentrated to dryness to give the title compound as an oil (21.4 g, yield 87%).

HPLC-MS (Method B): Ret, 1.26 min; $ESI^+$-MS m/z, 266 (M+1).

b) Phenyl methyl(2-((1-methyl-1H-pyrazol-5-yl)(thiophen-2-yl)methoxy)ethyl)carbamate A solution of phenyl chloroformate (2.55 g, 1.63 mmol) in DCM (10 mL) was added dropwise to a mixture of the compound obtained in the previous step (3.85 g, 14.85 mmol) and $K_2CO_3$ (4.4 g, 32.1 mmol) in DCM (50 mL). The mixture was stirred for 4 days at room temperature. Then the solid was filtered off, and the organic layer was washed with a diluted NaOH solution in water, dried over $Na_2SO_4$, filtered and concentrated. The residue was purified by flash chromatography on silica gel, eluent chloroform: MeOH (98:2) to afford the title compound as yellow oil (4.4 g, yield 81.5%).

c) Title Compound

A solution of the compound obtained in the previous step (4.4 g, 12.05 mmol) and KOH 85% (10.2 g, 155 mmol) in ethylene glycol (60 mL) was heated 1 h at 160° C. Then, the mixture was poured into 200 g of ice and extracted with ethyl ether. The organic layer was separated, washed with water and brine, dried over $Na_2SO_4$, filtered and concentrated. The residue was purified by flash chromatography on silica gel, eluent chloroform: MeOH (90:10) to afford the title compound as yellow oil (2.1 g, yield 71.2%).

HPLC-MS (Method B): Ret, 1.05 min; $ESI^+$-MS m/z, 252 (M+1).

A similar method was used for the preparation of intermediates 2B-H, using the corresponding intermediates 1 as starting materials:

| INT | Structure | Chemical name | Method | Ret (min) | MS (M + H) |
|---|---|---|---|---|---|
| 2B | 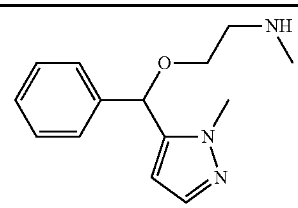 | N-methyl-2-((1-methyl-1H-pyrazol-5-yl)(phenyl)methoxy)ethanamine | B | 1.12 | 246.1 |
| 2C | 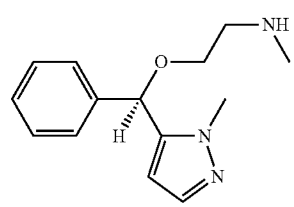 [SMILES: CNCCO[C@H](c1ccccc1)c1ccnn1C] | (R)-N-methyl-2-((1-methyl-1H-pyrazol-5-yl)(phenyl)methoxy)ethanamine | B | 1.12 | 246.1 |
| 2D | 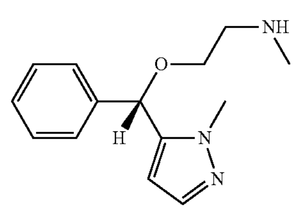 [SMILES: CNCCO[C@@H](c1ccccc1)c1ccnn1C] | (S)-N-methyl-2-((1-methyl-1H-pyrazol-5-yl)(phenyl)methoxy)ethanamine | B | 1.12 | 246.1 |
| 2E | 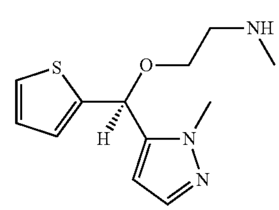 [SMILES: CNCCO[C@H](c1cccs1)c1ccnn1C] | (S)-N-methyl-2-((1-methyl-1H-pyrazol-5-yl)(thiophen-2-yl)methoxy)ethanamine | B | 1.05 | 252 |

| INT | Structure | Chemical name | Method | Ret (min) | MS (M + H) |
|---|---|---|---|---|---|
| 2F | 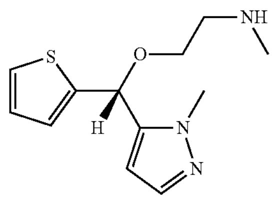 [SMILES: CNCCO[C@@H](c1cccs1)c1ccnn1C] | (R)-N-methyl-2-((1-methyl-1H-pyrazol-5-yl)(thiophen-2-yl)methoxy)ethanamine | B | 1.05 | 252 |
| 2G | 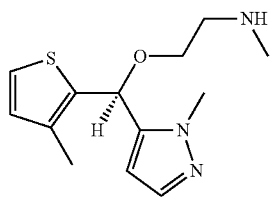 [SMILES: CNCCO[C@H](c1sccc1C)c1ccnn1C] | (S)-N-methyl-2-((1-methyl-1H-pyrazol-5-yl)(3-methylthiophen-2-yl)methoxy)ethanamine | | | |
| 2H | 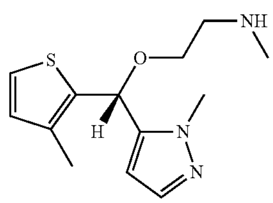 [SMILES: CNCCO[C@@H](c1sccc1C)c1ccnn1C] | (R)-N-methyl-2-((1-methyl-1H-pyrazol-5-yl)(3-methylthiophen-2-yl)methoxy)ethanamine | | | |

Intermediate 2I. N-(2-((1-Methyl-1H-pyrazol-5-yl)(phenyl)methoxy)ethyl)propan-2-amine

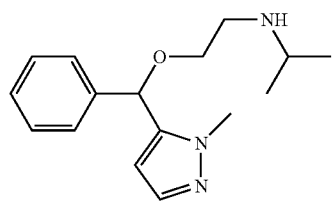 [SMILES: CC(C)NCCOC(c1ccccc1)c1ccnn1C]

Propan-2-one (865 μL, 11.7 mmol) was added to a solution of 2-((1-methyl-1H-pyrazol-5-yl)(phenyl)methoxy)ethanamine (intermediate 3D, 226.3 mg, 0.978 mmol) in AcOH (4 mL). The mixture was stirred at 45° C. for 1.5 h and then NaBH₄ (130 mg, 3.43 mmol) was added in three portions every 45 min. The reaction was stirred at 45° C. overnight and concentrated in vacuo. The residue was dissolved in water, the solution was basified with a saturated solution of K₂CO₃ to pH=10 and extracted with ethyl acetate. The organic layer was washed with water, dried over Na₂SO₄, filtered and concentrated to dryness to give the title compound as colorless oil (225 mg, yield 84%).

HPLC-MS (Method B): Ret, 1.33 min; ESI⁺-MS m/z, 274.1 (M+1).

Intermediate 3A. 5-((2-Chloroethoxy)(2-fluorophenyl)methyl)-1-methyl-1H-pyrazole

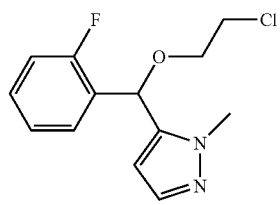 [SMILES: Cn1nccc1C(OCCCl)c1ccccc1F]

A solution of (2-fluorophenyl)(1-methyl-1H-pyrazol-5-yl)methanol (intermediate 1D, 146 mg, 0.708 mmol), 2-chloroethanol (100 μL, 1.47 mmol) and p-toluensulfonic acid monohydrate (10 mg, 0.047 mmol) in toluene (30 mL) was refluxed for 3 h, the water formed in the reaction being removed by azeotropic distillation with Dean-Stark. The reaction mixture was washed with water and with 5% NaHCO₃ aqueous solution. The organic layer was dried over Na₂SO₄, filtered, and concentrated to dryness to afford the title compound as amber oil (75 mg, yield 39.4%).

HPLC-MS (Method A): Ret, 1.52 min; ESI⁺-MS m/z, 269.1 (M+1).

A similar method was used for the preparation of intermediates 3B-3D, using suitable intermediates 1 as starting materials. For the synthesis of intermediate 3D, 2-aminoethanol was used instead of 2-chloroethanol.

| INT | Structure | Chemical name | Method | Ret (min) | MS (M + H) |
|---|---|---|---|---|---|
| 3B | 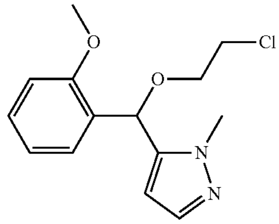 [SMILES: COc1ccccc1C(OCCCl)c1ccnn1C] | 5-((2-chloroethoxy)(2-methoxyphenyl)methyl)-1-methyl-1H-pyrazole | A | 2.42 | 281 |
| 3C | 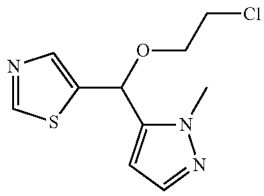 [SMILES: Cn1nccc1C(OCCCl)c1cncs1] | 5-((2-chloroethoxy)(1-methyl-1H-pyrazol-5-yl)methyl)thiazole | A | 1.12 | 258 |
| 3D | 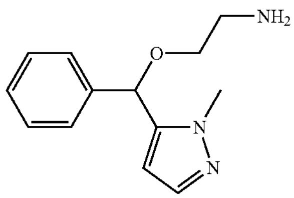 [SMILES: Cn1nccc1C(OCCN)c1ccccc1] | 2-((1-methyl-1H-pyrazol-5-yl)(phenyl)methoxy)ethanamine | B | 1.12 | 246.1 |

Example 1: N-benzyl-N-methyl-2-((1-methyl-1H-pyrazol-5-yl)(thiophen-2-yl)methoxy)ethanamine

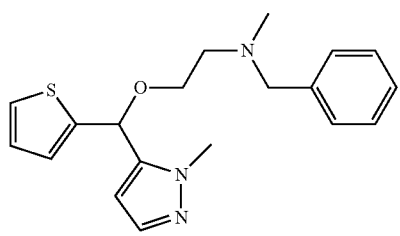 [SMILES: CN(CCOC(c1cccs1)c1ccnn1C)Cc1ccccc1]

N-methyl-2-((1-methyl-1H-pyrazol-5-yl)(thiophen-2-yl)methoxy)ethanamine (intermediate 2A, 222.5 mg, 0.885 mmol) was dissolved, under argon atmosphere, in DCE (4 mL) in a process vial. Benzaldehyde (180 µL, 1.77 mmol) and sodium triacetoxyborohydride (562 mg, 2.65 mmol) were added, and the vial was sealed with a septum. The suspension was subjected to microwave irradiating conditions for 12 min at 120° C. and then cooled. The crude product was evaporated to dryness and then suspended in aqueous NaHCO₃. The mixture was extracted with DCM and washed with saturated aqueous NaHCO₃. The organic layer was dried with Na₂SO₄, filtered and concentrated. The residue was purified by flash chromatography on silica gel, gradient chloroform to MeOH:chloroform (10:90) to afford the title compound as yellow oil (246 mg, yield 81%).

HPLC-MS (Method A): Ret, 3.26 min; ESI⁺-MS m/z, 342.2 (M+1).

A similar method was used for the preparation of examples 2-3, using intermediate 2B as starting material and suitable aldehydes:

| EX | Structure | Chemical name | Method | Ret (min) | MS (M + H) |
|---|---|---|---|---|---|
| 2 | 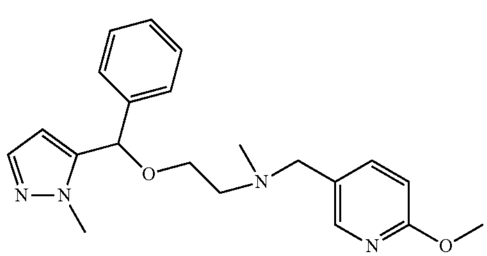 [SMILES: COc1ccc(CN(C)CCOC(c2ccccc2)c2ccnn2C)cn1] | N-((6-methoxypyridin-3-yl)methyl)-N-methyl-2-((1-methyl-1H-pyrazol-5-yl)(phenyl)methoxy)ethanamine | B | 1.88 | 367.9 |

| EX | Structure | Chemical name | Method | Ret (min) | MS (M + H) |
|---|---|---|---|---|---|
| 3 | 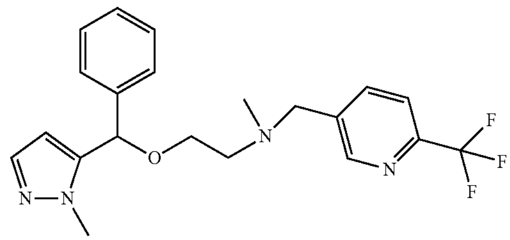 [SMILES: CN(CCOC(c1ccccc1)c1ccnn1C)Cc1ccc(C(F)(F)F)nc1] | N-methyl-2-((1-methyl-1H-pyrazol-5-yl)(phenyl)methoxy)-N-((6-(trifluoromethyl)pyridin-3-yl)methyl)ethanamine | B | 2.09 | 405.9 |

Example 4: N-methyl-2-((1-methyl-1H-pyrazol-5-yl)(thiophen-2-yl)methoxy)-N-phenethylethanamine

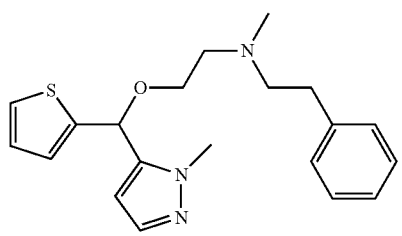 [SMILES: CN(CCOC(c1cccs1)c1ccnn1C)CCc1ccccc1]

To a suspension of $K_2CO_3$ (76.4 mg, 0.5 mmol) and N-methyl-2-((1-methyl-1H-pyrazol-5-yl)(thiophen-2-yl)methoxy)ethanamine (intermediate 2A, 45.2 mg, 0.18 mmol) in ACN (3 mL), 2-phenylethyl bromide (33 mg, 0.18 mmol) was added. The reaction was refluxed for 8 h and then it was cooled down to r.t. The solvent was evaporated and the residue was partioned between water and DCM. The aqueous layer was extracted with DCM and the combined organic layers were washed with water, dried over $Na_2SO_4$, filtered and concentrated to dryness to afford the title compound as yellow oil (45 mg, 55%).

HPLC-MS (Method A): Ret, 3.26 min; $ESI^+$-MS m/z, 356.2 (M+1).

A similar method was used for the preparation of examples 5-31, using the corresponding intermediates 2 as starting material and suitable alkylating agents:

| EX | Structure | Chemical name | Method | Ret (min) | MS (M + H) |
|---|---|---|---|---|---|
| 5 | 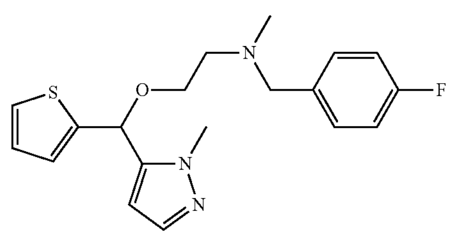 [SMILES: CN(CCOC(c1cccs1)c1ccnn1C)Cc1ccc(F)cc1] | N-(4-fluorobenzyl)-N-methyl-2-((1-methyl-1H-pyrazol-5-yl)(thiophen-2-yl)methoxy)ethanamine | A | 3.36 | 360.2 |
| 6 | 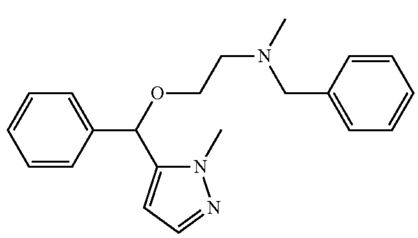 [SMILES: CN(CCOC(c1ccccc1)c1ccnn1C)Cc1ccccc1] | N-benzyl-N-methyl-2-((1-methyl-1H-pyrazol-5-yl)(phenyl)methoxy)ethanamine | A | 3.38 | 336.2 |
| 7 | 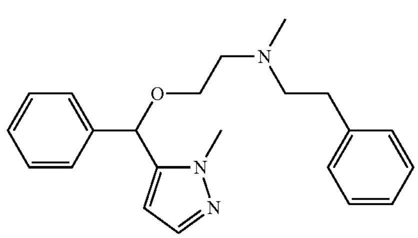 | N-methyl-2-((1-methyl-1H-pyrazol-5-yl)(phenyl)methoxy)-N-phenethylethanamine | A | 3.32 | 350.2 |

-continued

| EX | Structure | Chemical name | Method | Ret (min) | MS (M + H) |
|---|---|---|---|---|---|
| 8 | 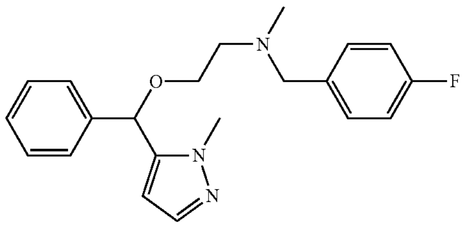 [SMILES: CN(CCOC(c1ccccc1)c1ccnn1C)Cc1ccc(F)cc1] | N-(4-fluorobenzyl)-N-methyl-2-((1-methyl-1H-pyrazol-5-yl)(phenyl)methoxy)ethanamine | A | 3.44 | 354.2 |
| 9 | 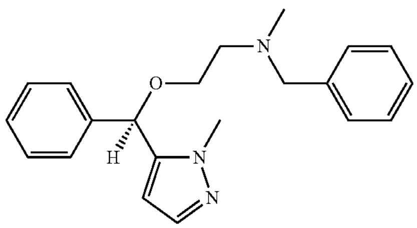 [SMILES: CN(CCO[C@H](c1ccccc1)c1ccnn1C)Cc1ccccc1] | (R)-N-benzyl-N-methyl-2-((1-methyl-1H-pyrazol-5-yl)(phenyl)methoxy)ethanamine | A | 3.39 | 336.2 |
| 10 | 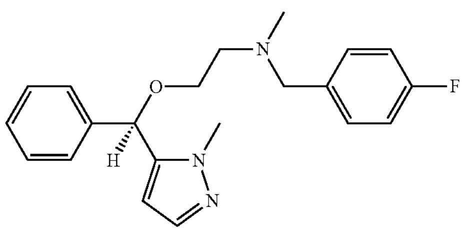 [SMILES: CN(CCO[C@H](c1ccccc1)c1ccnn1C)Cc1ccc(F)cc1] | (R)-N-(4-fluorobenzyl)-N-methyl-2-((1-methyl-1H-pyrazol-5-yl)(phenyl)methoxy)ethanamine | A | 3.44 | 354.3 |
| 11 | 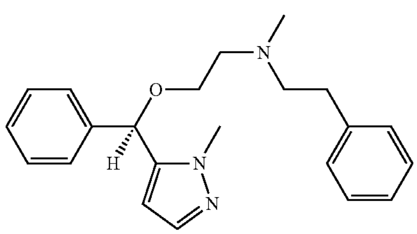 [SMILES: CN(CCO[C@H](c1ccccc1)c1ccnn1C)CCc1ccccc1] | (R)-N-methyl-2-((1-methyl-1H-pyrazol-5-yl)(phenyl)methoxy)-N-phenethylethanamine | A | 3.32 | 350.3 |
| 12 | 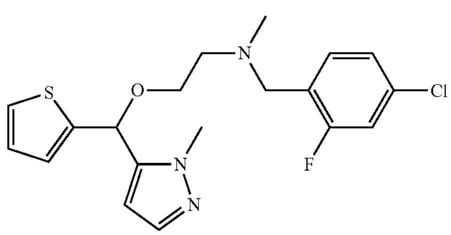 [SMILES: CN(CCOC(c1cccs1)c1ccnn1C)Cc1ccc(Cl)cc1F] | N-(4-chloro-2-fluorobenzyl)-N-methyl-2-((1-methyl-1H-pyrazol-5-yl)(thiophen-2-yl)methoxy)ethanamine | A | 3.64 | 394.2 |
| 13 | 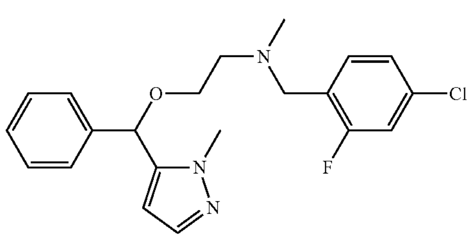 [SMILES: CN(CCOC(c1ccccc1)c1ccnn1C)Cc1ccc(Cl)cc1F] | N-(4-chloro-2-fluorobenzyl)-N-methyl-2-((1-methyl-1H-pyrazol-5-yl)(phenyl)methoxy)ethanamine | A | 3.74 | 388.2 |

-continued

| EX | Structure | Chemical name | Method | Ret (min) | MS (M + H) |
|---|---|---|---|---|---|
| 14 | 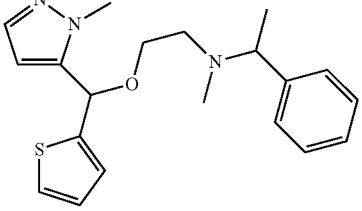 | N-methyl-2-((1-methyl-1H-pyrazol-5-yl)(thiophen-2-yl)methoxy)-N-(1-phenylethyl)ethanamine | A | 3.42 | 356.2 |
| 15 | 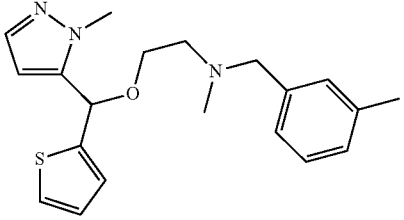 [SMILES: Cc1cccc(CN(C)CCOC(c2cccs2)c2ccnn2C)c1] | N-methyl-2-((1-methyl-1H-pyrazol-5-yl)(thiophen-2-yl)methoxy)-N-(3-methylbenzyl)ethanamine | A | 3.49 | 356.2 |
| 16 | 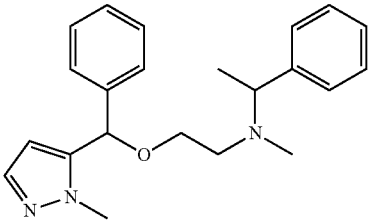 [SMILES: CC(c1ccccc1)N(C)CCOC(c1ccccc1)c1ccnn1C] | N-methyl-2-((1-methyl-1H-pyrazol-5-yl)(phenyl)methoxy)-N-(1-phenylethyl)ethanamine | A | 3.52 | 350.2 |
| 17 | 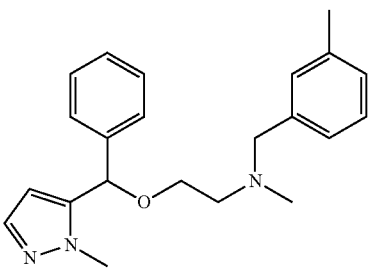 [SMILES: Cc1cccc(CN(C)CCOC(c2ccccc2)c2ccnn2C)c1] | N-methyl-2-((1-methyl-1H-pyrazol-5-yl)(phenyl)methoxy)-N-(3-methylbenzyl)ethanamine | A | 3.59 | 350.2 |
| 18 | 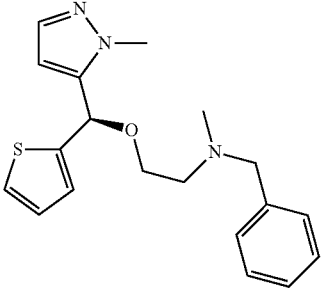 [SMILES: CN(CCO[C@@H](c1cccs1)c1ccnn1C)Cc1ccccc1] | (R)-N-benzyl-N-methyl-2-((1-methyl-1H-pyrazol-5-yl)(thiophen-2-yl)methoxy)ethanamine | A | 3.31 | 342.2 |
| 19 | 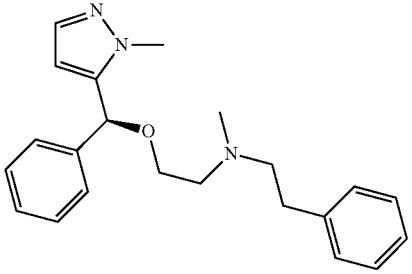 [SMILES: CN(CCO[C@@H](c1ccccc1)c1ccnn1C)CCc1ccccc1] | (S)-N-methyl-2-((1-methyl-1H-pyrazol-5-yl)(phenyl)methoxy)-N-phenethylethanamine | A | 3.34 | 350.3 |

| EX | Structure | Chemical name | Method | Ret (min) | MS (M + H) |
|---|---|---|---|---|---|
| 20 | 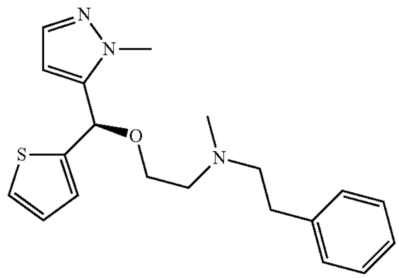 [SMILES: CN(CCO[C@@H](c1cccs1)c1ccnn1C)CCc1ccccc1] | (R)-N-methyl-2-((1-methyl-1H-pyrazol-5-yl)(thiophen-2-yl)methoxy)-N-phenethylethanamine | A | 3.24 | 356.3 |
| 21 | 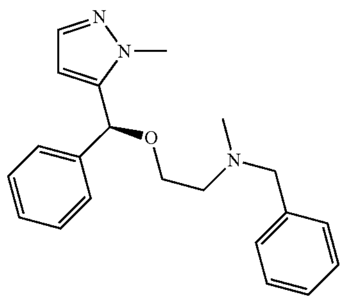 [SMILES: CN(CCO[C@@H](c1ccccc1)c1ccnn1C)Cc1ccccc1] | (S)-N-benzyl-N-methyl-2-((1-methyl-1H-pyrazol-5-yl)(phenyl)methoxy)ethanamine | A | 3.40 | 336.2 |
| 22 | 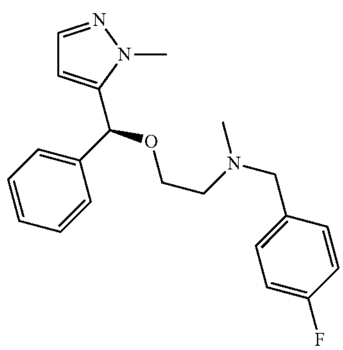 [SMILES: CN(CCO[C@@H](c1ccccc1)c1ccnn1C)Cc1ccc(F)cc1] | (S)-N-(4-fluorobenzyl)-N-methyl-2-((1-methyl-1H-pyrazol-5-yl)(phenyl)methoxy)ethanamine | A | 3.44 | 354.3 |
| 23 | 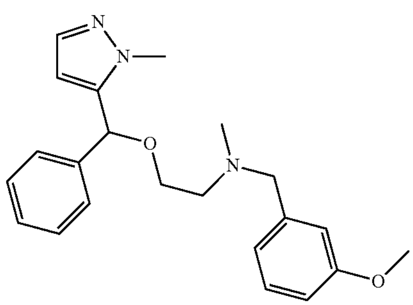 [SMILES: COc1cccc(CN(C)CCOC(c2ccccc2)c2ccnn2C)c1] | N-(3-methoxybenzyl)-N-methyl-2-((1-methyl-1H-pyrazol-5-yl)(phenyl)methoxy)ethanamine | A | 3.37 | 366.3 |
| 24 | 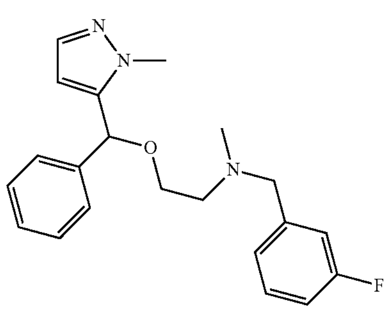 [SMILES: CN(CCOC(c1ccccc1)c1ccnn1C)Cc1cccc(F)c1] | N-(3-fluorobenzyl)-N-methyl-2-((1-methyl-1H-pyrazol-5-yl)(phenyl)methoxy)ethanamine | A | 3.49 | 354.2 |

-continued

| EX | Structure | Chemical name | Method | Ret (min) | MS (M + H) |
|---|---|---|---|---|---|
| 25 | 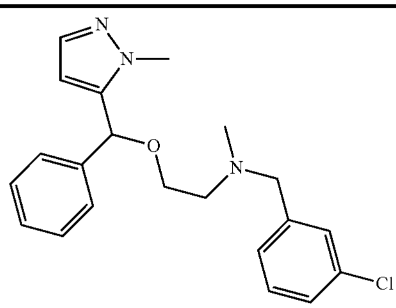 | N-(3-chlorobenzyl)-N-methyl-2-((1-methyl-1H-pyrazol-5-yl)(phenyl)methoxy) ethanamine | A | 3.70 | 370.2 |
| 26 | 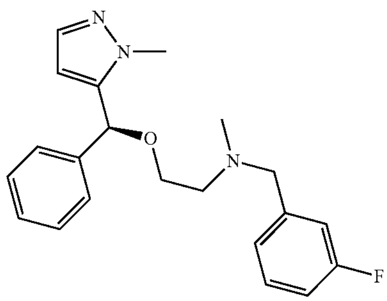 [SMILES: CN(CCO[C@@H](c1ccccc1)c1ccnn1C)Cc1cccc(F)c1] | (S)-N-(3-fluorobenzyl)-N-methyl-2-((1-methyl-1H-pyrazol-5-yl)(phenyl)methoxy) ethanamine | A | 3.47 | 354.3 |
| 27 | 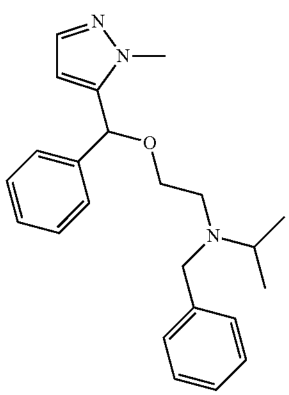 [SMILES: CC(C)N(CCOC(c1ccccc1)c1ccnn1C)Cc1ccccc1] | N-benzyl-N-(2-((1-methyl-1H-pyrazol-5-yl)(phenyl)methoxy)ethyl) propan-2-amine | B | 2.54 | 364.1 |
| 28 | 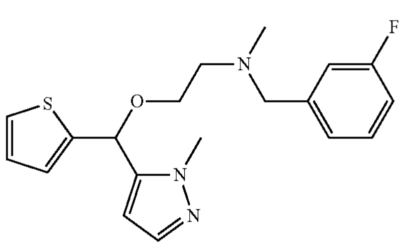 [SMILES: CN(CCOC(c1cccs1)c1ccnn1C)Cc1cccc(F)c1] | N-(3-fluorobenzyl)-N-methyl-2-((1-methyl-1H-pyrazol-5-yl)(thiophen-2-yl) methoxy) ethanamine | B | 2.13 | 360.1 |

-continued

| EX | Structure | Chemical name | Method | Ret (min) | MS (M + H) |
|---|---|---|---|---|---|
| 29 | 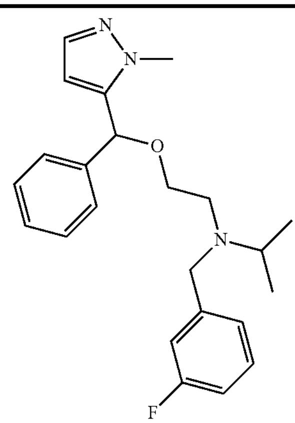 | N-(3-fluorobenzyl)-N-(2-((1-methyl-1H-pyrazol-5-yl)(phenyl)methoxy)ethyl)propan-2-amine | B | 2.57 | 382.1 |
| 30 | 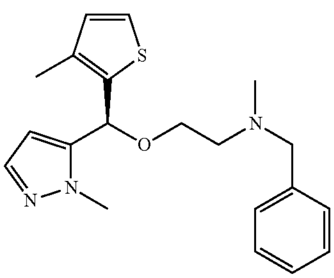 [SMILES: Cc1ccsc1[C@@H](OCCN(C)Cc1ccccc1)c1ccnn1C] | (S)-N-benzyl-N-methyl-2-((1-methyl-1H-pyrazol-5-yl)(3-methylthiophen-2-yl)methoxy)ethanamine | B | 2.17 | 356.1 |
| 31 | 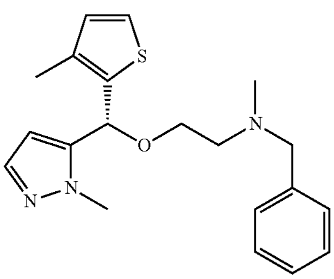 [SMILES: Cc1ccsc1[C@H](OCCN(C)Cc1ccccc1)c1ccnn1C] | (R)-N-benzyl-N-methyl-2-((1-methyl-1H-pyrazol-5-yl)(3-methylthiophen-2-yl)methoxy)ethanamine | B | 2.17 | 356.1 |

Example 32: N-(3,4-Dichlorophenethyl)-N-methyl-2-((1-methyl-1H-pyrazol-5-yl)(thiophen-2-yl)methoxy)ethanamine

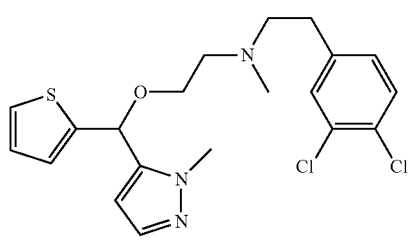 [SMILES: CN(CCOC(c1cccs1)c1ccnn1C)CCc1ccc(Cl)c(Cl)c1]

a) 2-(3,4-Dichlorophenyl)-N-methyl-N-(2-((1-methyl-1H-pyrazol-5-yl)(thiophen-2-yl)methoxy)ethyl)acetamide A mixture of N-methyl-2-((1-methyl-1H-pyrazol-5-yl)(thiophen-2-yl)methoxy)ethanamine (intermediate 2A, 126 mg, 0.5 mmol), 2-(3,4-dichlorophenyl)acetyl chloride (123 mg, 0.55 mmol) and DIPEA (216 μL, 1.25 mmol) in DCM (10 mL) was stirred at r.t in a sealed tube for 4 h. Water was added, and the reaction mixture was washed with saturated aqueous $K_2CO_3$ and HCl 1N. The organic layer was dried over $Na_2SO_4$, filtered and concentrated to obtain a crude compound that was purified by flash chromatography on silica gel, gradient chloroform to MeOH:chloroform (5:95) to afford the title compound (90 mg, yield 41%).

HPLC-MS (Method A): Ret, 3.21 min; ESI$^+$-MS m/z, 438.1 (M+1).

b) Title Compound 2-(3,4-Dichlorophenyl)-N-methyl-N-(2-((1-methyl-1H-pyrazol-5-yl)(thiophen-2-yl)methoxy)ethyl)acetamide (obtained in the previous step, 51.3 mg, 0.117 mmol) in THF (1 mL) was added dropwise to a stirred solution of freshly prepared aluminium hydride (590 μL, 0.59 mmol) in THF (5 mL). The reaction was maintained at 0° C. and stirred for 30 min and then a few drops of water were added to destroy the aluminum hydride excess. The solids were filtered off and washed with ethyl acetate and water. The filtrate was extracted with ethyl acetate and the organic layers were combined, washed with water, dried over $Na_2SO_4$, filtered and concentrated to dryness to afford the title compound as an oil (20 mg, yield 40%).

HPLC-MS (Method A): Ret, 3.74 min; $ESI^+$-MS m/z, 424 (M+1).

Example 33: N-benzyl-N-methyl-2-((1-methyl-1H-pyrazol-5-yl)(phenyl)methylthio)ethanamine

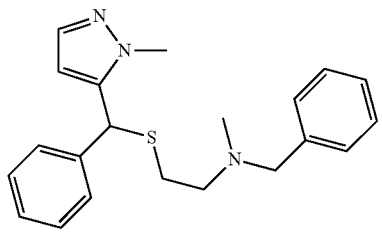 [SMILES: CN(CCSC(c1ccccc1)c1ccnn1C)Cc1ccccc1]

A solution of NaOH (72 mg, 1.8 mmol) in water (5 mL) was added to a solution of (1-methyl-1H-pyrazol-5-yl)(phenyl)methanethiol (intermediate 1L, 163 mg, 0.8 mmol) in EtOH (20 mL). The mixture was stirred 5 minutes and then, N-benzyl-2-chloro-N-methylethanamine hydrochloride (176 mg, 0.8 mmol) was added. The reaction mixture was stirred overnight at room temperature. The solvents were concentrated off and the residue was diluted with water. The aqueous layer was extracted with DCM and the combined organic layers were dried over $Na_2SO_4$, filtered and concentrated to obtain a crude that was purified by flash chromatography on silica gel, gradient chloroform to MeOH:chloroform (5:95) to afford the title compound as a colourless oil (230 mg, yield 82%).

HPLC-MS (Method A): Ret, 4.53 min; $ESI^+$-MS m/z, 352.1 (M+1).

Example 34: N-Benzyl-N-methyl-2-((1-methyl-1H-pyrazol-5-yl)(phenyl)methylsulfinyl)ethanamine

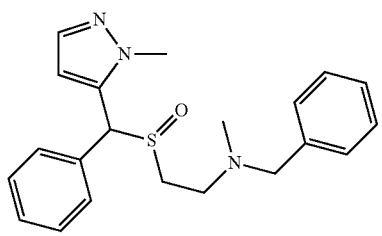 [SMILES: CN(CCS(=O)C(c1ccccc1)c1ccnn1C)Cc1ccccc1]

Hydrogen peroxide (26 µL, 0.857 mmol) was added to a solution of N-benzyl-N-methyl-2-((1-methyl-1H-pyrazol-5-yl)(phenyl)methylthio)ethanamine (example 33, 70 mg, 0.3 mmol) in MeOH (5 mL). The reaction mixture was stirred at r.t. for 6 h. Additional hydrogen peroxide (26 µL, 0.857 mmol) was added and the reaction was stirred at r.t. for additional 24 h. Then, the solvent was concentrated off and the residue was purified by flash chromatography on silica gel, gradient chloroform to MeOH:chloroform (5:95) to afford the title compound (19 mg, yield 26%).

HPLC-MS (Method A): Ret, 1.48 min; $ESI^+$-MS m/z, 368.1 (M+1).

Example 35: N-Benzyl-N-methyl-2-((1-methyl-1H-pyrazol-5-yl)(3-methylthiophen-2-yl)methoxy)ethanamine

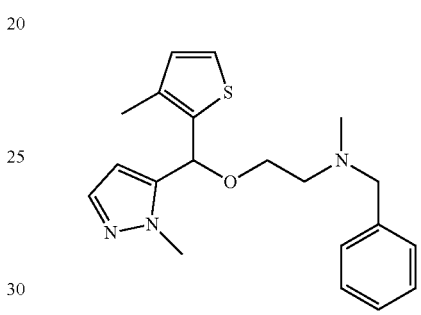

A mixture of (1-methyl-1H-pyrazol-5-yl)(3-methylthiophen-2-yl)methanol (intermediate 1A, 208.3 mg, 1 mmol), N-benzyl-2-chloro-N-methylethanamine hydrochloride (242 mg, 1.1 mmol) and tetrabutylammonium bromide (5 mg, 0.015 mmol) in 6 ml of NaOH (40% solution, 6 mL) and toluene (6 mL) was stirred vigorously and heated at 80° C. overnight. Then, the aqueous layer was separated and the organic layer was washed with water, dried over $Na_2SO_4$, filtered and concentrated to obtain a crude that was purified by flash chromatography on silica gel, gradient chloroform to MeOH:chloroform (5:95) to afford the title compound as a colorless oil (160 mg, yield 45%).

HPLC-MS (Method A): Ret, 4.46 min; $ESI^+$-MS m/z, 356.5 (M+1).

A similar method was used for the preparation of examples 36-46, using the corresponding intermediates 1 as starting materials and suitable alkylating agents:

| EX | Structure | Chemical name | Method | Ret (min) | MS (M + H) |
|---|---|---|---|---|---|
| 36 | 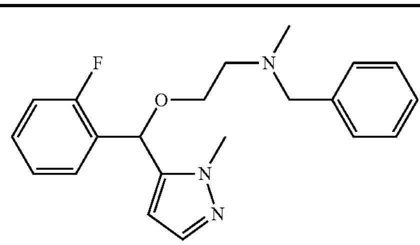 | N-benzyl-2-((2-fluorophenyl)(1-methyl-1H-pyrazol-5-yl)methoxy)-N-methylethanamine | A | 1.84 | 354.3 |

-continued

| EX | Structure | Chemical name | Method | Ret (min) | MS (M + H) |
|---|---|---|---|---|---|
| 37 | 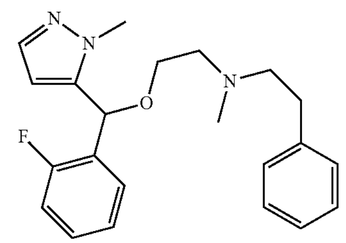 [SMILES: CN(CCOC(c1ccccc1F)c1ccnn1C)CCc1ccccc1] | 2-((2-fluorophenyl)(1-methyl-1H-pyrazol-5-yl)methoxy)-N-methyl-N-phenethylethanamine | A | 2.12 | 368.3 |
| 38 | 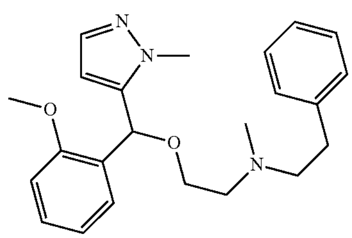 [SMILES: COc1ccccc1C(OCCN(C)CCc1ccccc1)c1ccnn1C] | 2-((2-methoxyphenyl)(1-methyl-1H-pyrazol-5-yl)methoxy)-N-methyl-N-phenethylethanamine | A | 2.09 | 380.3 |
| 39 | 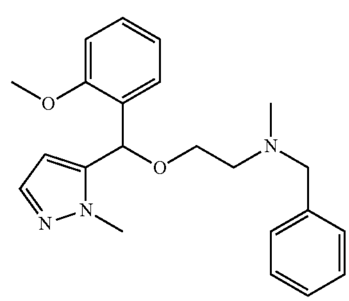 [SMILES: COc1ccccc1C(OCCN(C)Cc1ccccc1)c1ccnn1C] | N-benzyl-2-((2-methoxyphenyl)(1-methyl-1H-pyrazol-5-yl)methoxy)-N-methylethanamine | A | 2.14 | 366.3 |
| 40 | 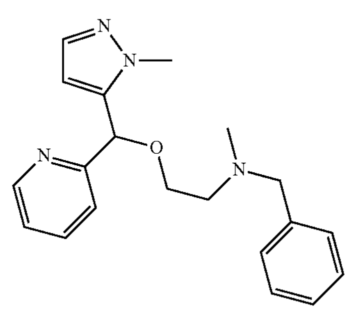 [SMILES: CN(CCOC(c1ccccn1)c1ccnn1C)Cc1ccccc1] | N-benzyl-N-methyl-2-((1-methyl-1H-pyrazol-5-yl)(pyridin-2-yl)methoxy)ethanamine | A | 1.69 | 337.2 |
| 41 | 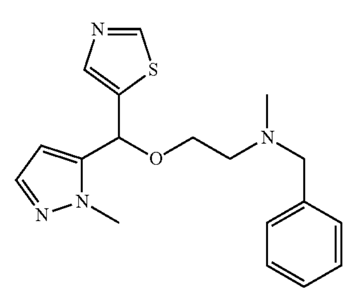 [SMILES: CN(CCOC(c1cncs1)c1ccnn1C)Cc1ccccc1] | N-benzyl-N-methyl-2-((1-methyl-1H-pyrazol-5-yl)(thiazol-5-yl)methoxy)ethanamine | B | 1.67 | 343.1 |

| EX | Structure | Chemical name | Method | Ret (min) | MS (M + H) |
|---|---|---|---|---|---|
| 42 | 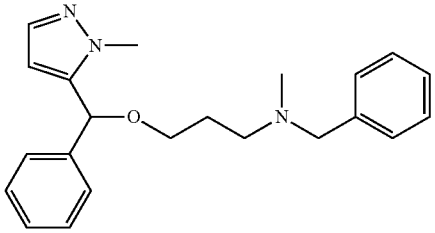 [SMILES: CN(CCCOC(c1ccccc1)c1ccnn1C)Cc1ccccc1] | N-benzyl-N-methyl-3-((1-methyl-1H-pyrazol-5-yl)(phenyl)methoxy)propan-1-amine | B | 2.74 | 350.1 |
| 43 | 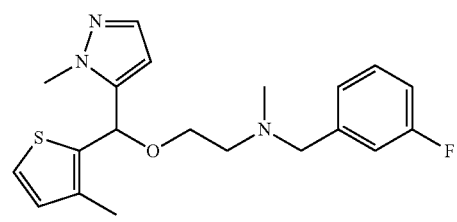 [SMILES: Cc1ccsc1C(OCCN(C)Cc1cccc(F)c1)c1ccnn1C] | N-(3-fluorobenzyl)-N-methyl-2-((1-methyl-1H-pyrazol-5-yl)(3-methylthiophen-2-yl)methoxy)ethanamine | B | 2.22 | 374.1 |
| 44 | 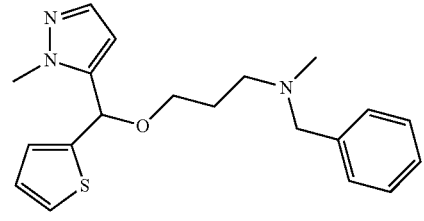 [SMILES: CN(CCCOC(c1cccs1)c1ccnn1C)Cc1ccccc1] | N-benzyl-N-methyl-3-((1-methyl-1H-pyrazol-5-yl)(thiophen-2-yl)methoxy)propan-1-amine | B | 2.08 | 356.1 |
| 45 | 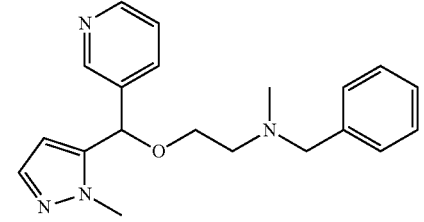 [SMILES: CN(CCOC(c1cccnc1)c1ccnn1C)Cc1ccccc1] | N-benzyl-N-methyl-2-((1-methyl-1H-pyrazol-5-yl)(pyridin-3-yl)methoxy)ethanamine | B | 1.64 | 337.3 |
| 46 | 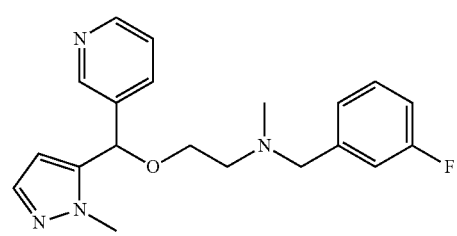 [SMILES: CN(CCOC(c1cccnc1)c1ccnn1C)Cc1cccc(F)c1] | N-(3-fluorobenzyl)-N-methyl-2-((1-methyl-1H-pyrazol-5-yl)(pyridin-3-yl)methoxy)ethanamine | B | 1.72 | 355.2 |

Example 47: N-(3-Fluorobenzyl)-2-((2-fluorophenyl)(1-methyl-1H-pyrazol-5-yl)methoxy)-N-methyl-ethanamine

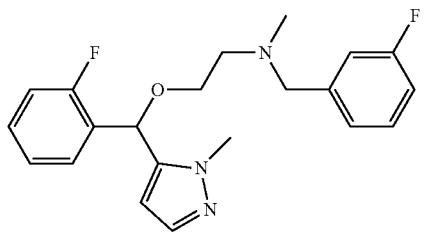 [SMILES: CN(CCOC(c1ccccc1F)c1ccnn1C)Cc1cccc(F)c1]

1-(3-Fluorophenyl)-N-methylmethanamine (40 μl, 0.277 mmol) was added to a solution of 5-((2-chloroethoxy)(2-fluorophenyl)methyl)-1-methyl-1H-pyrazole (intermediate 3A, 62 mg, 0.231 mmol) and $K_2CO_3$ (95 mg, 0.692 mmol) in DMF (1 mL). The reaction mixture was stirred at 130° C. for 6 h. After removal of the solvent in vacuo the residue was partioned between water and ethyl acetate. The aqueous layer was extracted three times with EtOAc and the combined organic layers were washed with water, dried over $Na_2SO_4$, filtered and concentrated. The resulting oil was purified by flash chromatography on silica gel, gradient cyclohexane to ethyl acetate from (90:10) to (0:100) to afford the title compound as a colorless oil (10 mg, yield 12%).

HPLC-MS (Method A): Ret, 3.79 min; ESI$^+$-MS m/z, 372.2 (M+1).

A similar method was used for the preparation of examples 48-49, using intermediates 3 as starting material:

| EX | Structure | Chemical name | Method | Ret (min) | MS (M + H) |
|---|---|---|---|---|---|
| 48 | 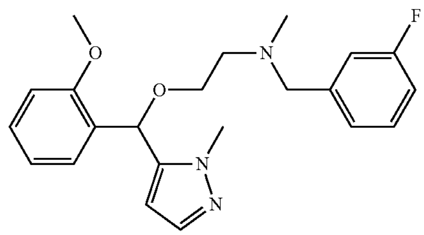 [SMILES: COc1ccccc1C(OCCN(C)Cc1cccc(F)c1)c1ccnn1C] | N-(3-fluorobenzyl)-2-((2-methoxyphenyl)(1-methyl-1H-pyrazol-5-yl)methoxy)-N-methylethanamine | A | 2.21 | 384.2 |
| 49 | 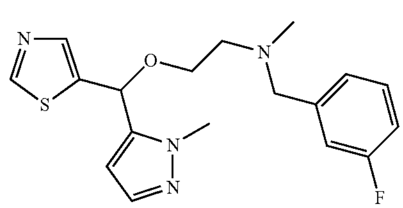 [SMILES: CN(CCOC(c1cncs1)c1ccnn1C)Cc1cccc(F)c1] | N-(3-fluorobenzyl)-N-methyl-2-((1-methyl-1H-pyrazol-5-yl)(thiazol-5-yl)methoxy)ethanamine | B | 1.75 | 361.1 |

Example 50: N1-benzyl-N1,N$_2$-dimethyl-N2-((1-methyl-1H-pyrazol-5-yl)(phenyl)methyl)ethane-1,2-diamine

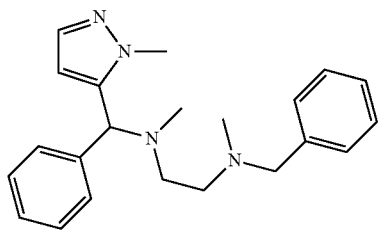 [SMILES: CN(CCN(C)C(c1ccccc1)c1ccnn1C)Cc1ccccc1]

a) 2-((1-Methyl-1H-pyrazol-5-yl)(phenyl)methylamino)etanol (1-Methyl-1H-pyrazol-5-yl)(phenyl)methanol (intermediate 1C, 1.5 g, 7.9 mmol) was dissolved in 33% HBr in AcOH (15 mL). The reaction was stirred at room temperature for 1 h and then the solvent was removed in vacuo. Ethanolamine (10 mL) was added to the residue and the mixture was stirred at 50° C. for 14 h. After cooling to r.t. water (25 mL) was added. The aqueous layer was extracted with DCM and the organic layers were combined, washed with water, dried over Na$_2$SO$_4$, filtered and concentrated. The crude compound was purified by flash chromatography on silica gel, gradient chloroform to MeOH from (99:1) to (96:4) to afford the title compound as yellow oil (260 mg, yield 14%).

HPLC-MS (Method B): Ret, 1.10 min; ESI$^+$-MS m/z, 232.1 (M+1).

b) 2-(Methyl((1-methyl-1H-pyrazol-5-yl)(phenyl)methyl)amino)ethanol 2-((1-Methyl-1H-pyrazol-5-yl)(phenyl)methylamino)etanol (obtained in step a, 231 mg, 1 mmol) was dissolved in DCE (5 mL). DIPEA (171 µl, 1 mmol) and formaldehyde (37% aqueous solution, 112 µL, 1.5 mmol) was added and the solution was cooled to 0° C. Sodium triacetoxyborohydride was added (848 mg, 4 mmol) and the reaction mixture was stirred at r.t. overnight. Then, NaHCO$_3$ saturated aqueous solution (10 mL) was added and the crude compound was extracted with DCM. The combined organic layers were washed with water, dried with Na$_2$SO$_4$, filtered and concentrated to afford the title compound as an oil (223 mg, yield 91%).

HPLC-MS (Method B): Ret, 1.29 min; ESI$^+$-MS m/z, 246.1 (M+1).

c) 2-Chloro-N-methyl-N-((1-methyl-1H-pyrazol-5-yl)(phenyl)methyl)ethanamine

Thionyl chloride (183 mg, 1.54 mmol) was added to a solution of 2-(methyl((1-methyl-1H-pyrazol-5-yl)(phenyl)methyl)amino)ethanol (obtained in step b, 190 mg, 0.77 mmol) in toluene (5 mL) and the reaction mixture was stirred at r.t. for 3 h. The solvent was concentrated off and the crude product was re-crystallized from ethanol to give the title compound (98 mg, 48% yield) that was used in the next step without further purification.

d) Title Compound

K$_2$CO$_3$ (152 mg, 1.1 mmol), KI (20 mg, 0.12 mmol) and methyl benzylamine (48 mg, 0.4 mmol) were added to a solution of 2-chloro-N-methyl-N-((1-methyl-1H-pyrazol-5-yl)(phenyl)methyl)ethanamine (obtained in step c, 98 mg, 0.37 mmol) in ACN (8 mL). The reaction mixture was refluxed for 20 h and then, the solvents were concentrated off and the residue was poured into water and extracted with DCM. The combined organic layers were dried over Na$_2$SO$_4$, filtered and concentrated. The crude compound was purified by flash chromatography on silica gel, gradient chloroform to MeOH from (99:1) to (95:5) to afford the title compound as white oil (14 mg, yield 11%).

HPLC-MS (Method B): Ret, 2.11 min; ESI$^+$-MS m/z, 349.2 (M+1).

Example 51: 4-((2-(benzyl(methyl)amino)ethoxy)(1-methyl-1H-pyrazol-5-yl)methyl)phenol

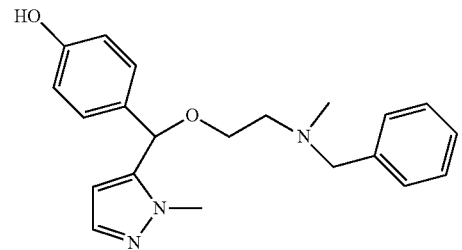 [SMILES: CN(CCOC(c1ccc(O)cc1)c1ccnn1C)Cc1ccccc1]

N-benzyl-N-methyletanolamine (79 µl, 0.478 mmol) and two drops of H$_2$SO$_4$ were added to a solution of 4-(hydroxy(1-methyl-1H-pyrazol-5-yl)methyl)phenol (intermediate 1K, 80 mg, 0.392 mmol) in toluene (20 mL). The reaction was refluxed for 4 h, the water formed being removed by azeotropic distillation with Dean-Stark. Then, the solvent was removed in vacuo and the residue was partioned between water and DCM; the aqueous layer was extracted with DCM, and the combined organic layers were washed with 5% NaHCO$_3$ and water again, dried over Na$_2$SO$_4$, filtered and concentrated. The resulting oil was purified by flash chromatography on silica gel, gradient cyclohexane to ethyl acetate from (80:20) to (0:100) to afford the title compound as a colorless oil (20 mg, yield 15%).

HPLC-MS (Method B): Ret, 1.72 min; ESI$^+$-MS m/z, 352.2 (M+1).

A similar method was used for the preparation of examples 52-53, using intermediate 1J as starting material and suitable ethanolamines:

| EX | Structure | Chemical name | Method | Ret (min) | MS (M + H) |
|---|---|---|---|---|---|
| 52 | 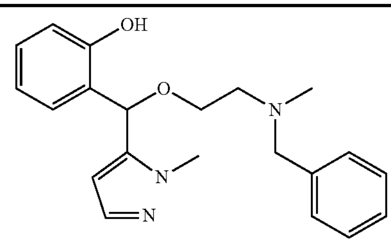 | 2-((2-(benzyl(methyl)amino)ethoxy)(1-methyl-1H-pyrazol-5-yl)methyl)phenol | B | 1.93 | 352.3 |
| 53 | 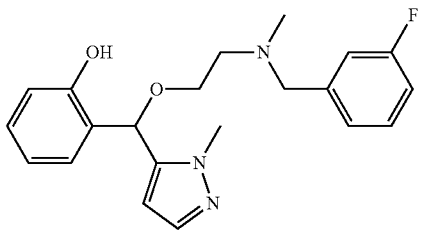 [SMILES: CN(CCOC(c1ccccc1O)c1ccnn1C)Cc1cccc(F)c1] | 2-((2-((3-fluorobenzyl)(methyl)amino)ethoxy)(1-methyl-1H-pyrazol-5-yl)methyl)phenol | B | 2.00 | 370.3 |

Table of Examples with Binding to the µ-opioid Receptor and the σ1-Receptor

Biological Activity

Pharmacological Study

Human σ₁ Receptor Radioligand Assay

To investigate binding properties of test compounds to human σ₁ receptor, transfected HEK-293 membranes and [³H](+)-pentazocine (Perkin Elmer, NET-1056), as the radioligand, were used. The assay was carried out with 7 µg of membrane suspension, 5 nM of [³H](+)-pentazocine in either absence or presence of either buffer or 10 µM Haloperidol for total and non-specific binding, respectively. Binding buffer contained Tris-HCl 50 mM at pH 8. Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH7.4). Filters were dried and counted at approximately 40% efficiency in a MicroBeta scintillation counter (Perkin-Elmer) using EcoScint liquid scintillation cocktail Human µ-Opioid Receptor Radioligand Assay To investigate binding properties of test compounds to human µ-opioid receptor, transfected CHO-K1 cell membranes and [³H]-DAMGO (Perkin Elmer, ES-542-C), as the radioligand, were used. The assay was carried out with 20 µg of membrane suspension, 1 nM of [³H]-DAMGO in either absence or presence of either buffer or 10 µM Naloxone for total and non-specific binding, respectively. Binding buffer contained Tris-HCl 50 mM, MgCl2 5 mM at pH 7.4. Plates were incubated at 27° C. for 60 minutes. After the incubation period, the reaction mix was then transferred to MultiScreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail.

Results

As this invention is aimed at providing a compound or a chemically related series of compounds which act as dual ligands of the σ₁ receptor and the µ-opiod receptor it is a very preferred embodiment in which the compounds are selected which act as dual ligands of the σ₁ receptor and the µ-opiod receptor and especially compounds which have a binding expressed as $K_i$ which is preferably <1000 nM for both receptors, more preferably <500 nM, even more preferably <100 nM.

The following scale as been adopted for representing the binding to the the σ₁ receptor and the µ-opioid receptor expressed as $K_i$:
+ Both $K_i$-µ and $K_i$-σ₁ >=500 nM
++ One $K_i$<500 nM while the other $K_i$ is >=500 nM
+++ Both $K_i$-µ and $K_i$-σ₁ <500 nM
++++ Both $K_i$-µ and $K_i$-σ₁ <100 nM All compounds prepared in the present application exhibit binding to the σ₁ receptor and the µ-opiod receptor, in particular the following binding results are shown:

| EX | µ and σ₁ dual binding |
|---|---|
| 1 | ++++ |
| 2 | + |
| 3 | + |
| 4 | ++++ |
| 5 | +++ |
| 6 | +++ |
| 7 | +++ |
| 8 | ++ |
| 9 | ++ |
| 10 | ++ |
| 11 | ++ |
| 12 | +++ |
| 13 | +++ |
| 14 | +++ |
| 15 | ++++ |
| 16 | ++ |
| 17 | +++ |
| 18 | ++++ |
| 19 | +++ |
| 20 | +++ |
| 21 | +++ |
| 22 | +++ |

-continued

| EX | μ and σ₁ dual binding |
|---|---|
| 23 | ++ |
| 24 | +++ |
| 25 | +++ |
| 26 | +++ |
| 27 | ++ |
| 28 | +++ |
| 29 | ++ |
| 30 | ++ |
| 31 | +++ |
| 32 | ++++ |
| 33 | +++ |
| 34 | + |
| 35 | +++ |
| 36 | +++ |
| 37 | +++ |
| 38 | +++ |
| 39 | ++ |
| 40 | + |
| 41 | + |
| 42 | +++ |
| 43 | +++ |
| 44 | ++++ |
| 45 | +++ |
| 46 | ++ |
| 47 | +++ |
| 48 | ++ |
| 49 | ++ |
| 50 | +++ |
| 51 | ++ |
| 52 | +++ |
| 53 | +++ |

The invention claimed is:

1. A compound of Formula (I):

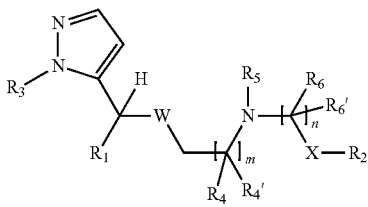

(I)

wherein
n is 1;
m is 1;
W is —O—, —NR$_w$—, —S— or —S(O)—;
X is a bond;
R$_1$ is substituted or unsubstituted cycloalkyl, substituted or unsubstituted aryl, or substituted or unsubstituted heterocyclyl;
  wherein said cycloalkyl, aryl or heterocyclyl in R$_1$, if substituted, is substituted with one or more substituent/s selected from halogen, —R$_8$, —OR$_8$, —NO$_2$, —NR$_8$R$_{8'''}$, NR$_8$C(O)R$_{8'}$, —NR$_8$S(O)$_2$R$_{8'}$, —S(O)$_2$NR$_8$R$_{8'}$, —NR$_8$C(O)NR$_8$R$_{8''}$, —SR$_8$, —S(O)R$_8$, S(O)$_2$R$_8$, —CN, haloalkyl, haloalkoxy, —C(O)OR$_8$, —C(O)NR$_8$R$_{8'}$, —OCH$_2$CH$_2$OH, —NR$_8$S(O)$_2$NR$_8$R$_{8''}$, and C(CH$_3$)$_2$OR$_8$;
  wherein R$_8$, R$_{8'}$ and R$_{8''}$ are independently selected from hydrogen, unsubstituted C$_{1-6}$ alkyl, unsubstituted C$_{2-6}$ alkenyl, unsubstituted C$_{2-6}$ alkynyl, unsubstituted aryl, unsubstituted alkylaryl, unsubstituted cycloalkyl, unsubstituted alkylcycloalkyl, unsubstituted heterocyclyl, and unsubstituted alkylheterocylcyl;
  and wherein R$_{8'''}$ is selected from hydrogen, unsubstituted C$_{1-6}$ alkyl, unsubstituted C$_{2-6}$ alkenyl, unsubstituted C$_{2-6}$ alkynyl, and -Boc;
R$_2$ is substituted or unsubstituted cycloalkyl, substituted or unsubstituted aryl, or substituted or unsubstituted heterocyclyl;
  wherein said cycloalkyl, aryl or heterocyclyl in R$_2$, if substituted, is substituted with one or more substituent/s selected from halogen, —R$_9$, —OR$_9$, —NO$_2$, —NR$_9$R$_{9'''}$, NR$_9$C(O)R$_{9'}$, —NR$_9$S(O)$_2$R$_{9'}$, —S(O)$_2$NR$_9$R$_{9'}$, —NR$_9$C(O)NR$_9$R$_{9''}$, —SR$_9$, —S(O)R$_9$, S(O)$_2$R$_9$, —CN, haloalkyl, haloalkoxy, —C(O)NR$_9$R$_{9'}$, —OCH$_2$CH$_2$OH, —NR$_9$S(O)$_2$NR$_9$R$_{9''}$, and C(CH$_3$)$_2$OR$_9$;
  wherein R$_9$, R$_{9'}$ and R$_{9''}$ are independently selected from hydrogen, unsubstituted C$_{1-6}$ alkyl, unsubstituted C$_{2-6}$ alkenyl, and unsubstituted C$_{2-6}$ alkynyl;
  and wherein R$_{9'''}$ is selected from hydrogen, unsubstituted C$_{1-6}$ alkyl, unsubstituted C$_{2-6}$ alkenyl, unsubstituted C$_{2-6}$ alkynyl, and -Boc;
R$_3$ is hydrogen, or substituted or unsubstituted C$_{1-6}$ alkyl, substituted or unsubstituted C$_{2-6}$ alkenyl, or substituted or unsubstituted C$_{2-6}$ alkynyl;
R$_4$ and R$_{4'}$ are independently selected from hydrogen, unsubstituted C$_{1-6}$ alkyl, unsubstituted C$_{2-6}$ alkenyl, and unsubstituted C$_{2-6}$ alkynyl;
R$_5$ is selected from hydrogen, substituted or unsubstituted C$_{1-6}$ alkyl, substituted or unsubstituted C$_{2-6}$ alkenyl, and substituted or unsubstituted C$_{2-6}$ alkynyl;
R$_6$ and R$_{6'}$ are independently selected from hydrogen, substituted or unsubstituted C$_{1-6}$ alkyl, substituted or unsubstituted C$_{2-6}$ alkenyl, substituted or unsubstituted C$_{2-6}$ alkynyl, —C(O)OR$_{10}$, and —C(O)NR$_{10}$R$_{10'}$;
  wherein R$_{10}$ and R$_{10'}$ are independently selected from hydrogen, unsubstituted C$_{1-6}$ alkyl, unsubstituted C$_{2-6}$ alkenyl, and unsubstituted C$_{2-6}$ alkynyl;
R$_w$ is selected from hydrogen, substituted or unsubstituted C$_{1-6}$ alkyl, substituted or unsubstituted C$_{2-6}$ alkenyl, and substituted or unsubstituted C$_{2-6}$ alkynyl, —C(O)R$_{12}$, —C(O)OR$_{12}$, and —C(O)NR$_{12}$R$_{12'}$;
  wherein R$_{12}$ and R$_{12'}$ are independently selected from hydrogen, unsubstituted C$_{1-6}$ alkyl, unsubstituted C$_{2-6}$ alkenyl, and unsubstituted C$_{2-6}$ alkynyl;
and/or
wherein the alkyl, alkylene or alkynyl, other than those defined in R$_1$ or R$_2$, if substituted, is substituted with one or more substituents selected from —OR$_{13}$, halogen, —CN, haloalkyl, haloalkoxy, —NR$_{13}$R$_{13'''}$, —SR$_{13}$, —S(O)R$_{13}$, and —S(O)$_2$R$_{13}$;
  wherein R$_{13}$ is selected from hydrogen, unsubstituted C$_{1-6}$ alkyl, unsubstituted C$_{2-6}$ alkenyl, and unsubstituted C$_{2-6}$ alkynyl;
  and wherein R$_{13'''}$ is selected from hydrogen, unsubstituted C$_{1-6}$ alkyl, unsubstituted C$_{2-6}$ alkenyl, unsubstituted C$_{2-6}$ alkynyl, and -Boc;
and/or
wherein the aryl, heterocyclyl or cycloalkyl, also in alkylaryl, alkylcycloalkyl and alkylheterocyclyl, other than those defined in R$_1$ or R$_2$, if substituted, is substituted with one or more substituents selected from halogen, —R$_{14}$, —OR$_{14}$, —NO$_2$, —NR$_{14}$R$_{14'''}$, NR$_{14}$C(O)R$_{14'}$, —NR$_{14}$S(O)$_2$R$_{14'}$, —S(O)$_2$NR$_{14}$R$_{14'}$, —NR$_{14}$C(O)NR$_{14}$R$_{14''}$, —SR$_{14}$, —S(O)R$_{14}$, S(O)$_2$R$_{14}$, —CN, haloalkyl, haloalkoxy, —C(O)OR$_{14}$, —C(O)NR$_{14}$R$_{14'}$, —OCH$_2$CH$_2$OH, —NR$_{14}$S(O)$_2$NR$_{14}$R$_{14''}$, and C(CH$_3$)$_2$OR$_{14}$;

wherein R$_{14}$, R$_{14'}$ and R$_{14''}$ are independently selected from hydrogen, unsubstituted C$_{1-6}$ alkyl, unsubstituted C$_{2-6}$ alkenyl, unsubstituted C$_{2-6}$ alkynyl, unsubstituted aryl, unsubstituted alkylaryl, unsubstituted cycloalkyl, unsubstituted alkylcycloalkyl, unsubstituted heterocyclyl, and unsubstituted alkyheterocylcyl;

and wherein R$_{14'''}$ is selected from hydrogen, unsubstituted C$_{1-6}$ alkyl, unsubstituted C$_{2-6}$ alkenyl, unsubstituted C$_{2-6}$ alkynyl, and -Boc;

optionally as a stereoisomer, including enantiomers and diastereomers, a racemate or a mixture of at least two stereoisomers, including enantiomers and/or diastereomers, in any mixing ratio, or a corresponding salt thereof, or a corresponding solvate thereof.

2. The compound according to claim 1, wherein W is —O—.

3. The compound according to claim 1, wherein R$_2$ is substituted or unsubstituted phenyl.

4. The compound according to claim 1, wherein R$_1$ is substituted or unsubstituted phenyl and R$_2$ is substituted or unsubstituted phenyl.

5. The compound according to claim 1, wherein R$_1$ is substituted or unsubstituted thiophene and R$_2$ is substituted or unsubstituted phenyl.

6. The compound according to claim 1, which is selected from:
N-benzyl-N-methyl-2-((1-methyl-1H-pyrazol-5-yl)(thiophen-2-yl)methoxy)ethanamine,
N-((6-methoxypyridin-3-yl)methyl)-N-methyl-2-((1-methyl-1H-pyrazol-5-yl)(phenyl)methoxy)ethanamine,
N-methyl-2-((1-methyl-1H-pyrazol-5-yl)(phenyl)methoxy)-N-((6-(trifluoromethyl)pyridin-3-yl)methyl)ethanamine,
N-(4-fluorobenzyl)-N-methyl-2-((1-methyl-1H-pyrazol-5-yl)(thiophen-2-yl)methoxy)ethanamine,
N-benzyl-N-methyl-2-((1-methyl-1H-pyrazol-5-yl)(phenyl)methoxy)ethanamine,
N-(4-fluorobenzyl)-N-methyl-2-((1-methyl-1H-pyrazol-5-yl)(phenyl)methoxy)ethanamine,
(R)-N-benzyl-N-methyl-2-((1-methyl-1H-pyrazol-5-yl)(phenyl)methoxy)ethanamine,
(R)-N-(4-fluorobenzyl)-N-methyl-2-((1-methyl-1H-pyrazol-5-yl)(phenyl)methoxy)ethanamine,
N-(4-chloro-2-fluorobenzyl)-N-methyl-2-((1-methyl-1H-pyrazol-5-yl)(thiophen-2-yl)methoxy)ethanamine,
N-(4-chloro-2-fluorobenzyl)-N-methyl-2-((1-methyl-1H-pyrazol-5-yl)(phenyl)methoxy)ethanamine,
N-methyl-2-((1-methyl-1H-pyrazol-5-yl)(thiophen-2-yl)methoxy)-N-(1-phenylethyl)ethanamine,
N-methyl-2-((1-methyl-1H-pyrazol-5-yl)(thiophen-2-yl)methoxy)-N-(3-methylbenzyl)ethanamine,
N-methyl-2-((1-methyl-1H-pyrazol-5-yl)(phenyl)methoxy)-N-(1-phenylethyl)ethanamine,
N-methyl-2-((1-methyl-1H-pyrazol-5-yl)(phenyl)methoxy)-N-(3-methylbenzyl)ethanamine,
(R)-N-benzyl-N-methyl-2-((1-methyl-1H-pyrazol-5-yl)(thiophen-2-yl)methoxy)ethanamine,
(S)-N-benzyl-N-methyl-2-(1-methyl(1-methyl-1H-pyrazol-5-yl)(phenyl)methoxy)ethanamine,
(S)-N-(4-fluorobenzyl)-N-methyl-2-((1-methyl-1H-pyrazol-5-yl)(phenyl)methoxy)ethanamine,
(N-(3-fluorobenzyl)-N-methyl-2-((1-methyl-1H-pyrazol-5-yl)(phenyl)methoxy)ethanamine,
N-(3-chlorobenzyl)-N-methyl-2-((1-methyl-1H-pyrazol-5-yl)(phenyl)methoxy)ethanamine,
(N-(3-fluorobenzyl)-N-methyl-2-((1-methyl-1H-pyrazol-5-yl)(phenyl)methoxy)ethanamine,
(S)-N-(3-fluorobenzyl)-N-methyl-2-((1-methyl-1H-pyrazol-5-yl)(phenyl)methoxy)ethanamine,
N-benzyl-N-(2-((1-methyl-1H-pyrazol-5-yl)(phenyl)methoxy)ethyl)propan-2-amine,
N-(3-fluorobenzyl)-N-methyl-2-((1-methyl-1H-pyrazol-5-yl)(thiophen-2-yl)methoxy)ethanamine,
N-(3-fluorobenzyl)-N-(2-((1-methyl-1H-pyrazol-5-yl)(phenyl)methoxy)ethyl)propan-2-amine,
(S)-N-benzyl-N-methyl-2-((1-methyl-1H-pyrazol-5-yl)(3-methylthiophen-2-yl)methoxy)ethanamine,
(R)-N-benzyl-N-methyl-2-((1-methyl-1H-pyrazol-5-yl)(3-methylthiophen-2-yl)methoxy)ethanamine,
N-benzyl-N-methyl-2-((1-methyl-1H-pyrazol-5-yl)(phenyl)methylthio)ethanamine,
N-benzyl-N-methyl-2-((1-methyl-1H-pyrazol-5-yl)(phenyl)methylsulfinyl)ethanamine,
N-benzyl-N-methyl-2-((1-methyl-1H-pyrazol-5-yl)(3-methylthiophen-2-yl)methoxy)ethanamine,
N-benzyl-2-((2-fluorophenyl)(1-methyl-1H-pyrazol-5-yl)methoxy)-N-methylethanamine,
N-benzyl-2-((2-methoxyphenyl)(1-methyl-1H-pyrazol-5-yl)methoxy)-N-methylethanamine,
N-benzyl-N-methyl-2-((1-methyl-1H-pyrazol-5-yl)(pyridin-2-yl)methoxy)ethanamine,
N-benzyl-N-methyl-2-((1-methyl-1H-pyrazol-5-yl)(thiazol-5-yl)methoxy)ethanamine,
N-(3-fluorobenzyl)-N-methyl-2-((1-methyl-1H-pyrazol-5-yl)(3-methylthiophen-2-yl)methoxy)ethanamine,
N-benzyl-N-methyl-2-((1-methyl-1H-pyrazol-5-yl)(pyridin-3-yl)methoxy)ethanamine,
N-(3-fluorobenzyl)-N-methyl-2-((1-methyl-1H-pyrazol-5-yl)(pyridin-3-yl)methoxy)ethanamine,
N-(3-fluorobenzyl)-2-((2-fluorophenyl)(1-methyl-1H-pyrazol-5-yl)methoxy)-N-methylethanamine,
N-(3-fluorobenzyl)-2-((2-methoxyphenyl)(1-methyl-1H-pyrazol-5-yl)methoxy)-N-methylethanamine,
N-(3-fluorobenzyl)-N-methyl-2-((1-methyl-1H-pyrazol-5-yl)(thiazol-5-yl)methoxy)ethanamine,
N1-benzyl-N1,N2-dimethyl-N2-((1-methyl-1H-pyrazol-5-yl)(phenyl)methyl)ethane-1,2-diamine,
4-((2-(benzyl(methyl)amino)ethoxy)(1-methyl-1H-pyrazol-5-yl)methyl)phenol,
2-((2-(benzyl(methyl)amino)ethoxy)(1-methyl-1H-pyrazol-5-yl)methyl)phenol, and
2-((2-((3-fluorobenzyl)(methyl)amino)ethoxy)(1-methyl-1H-pyrazol-5-yl)methyl)phenol, optionally as a stereoisomer, including enantiomers and diastereomers, a racemate or a mixture of at least two of stereoisomers, including enantiomers and/or diastereomers, in any mixing ratio, or a corresponding salt thereof, or a corresponding solvate thereof.

7. A process for preparing a compound of Formula (I) according to claim 1,

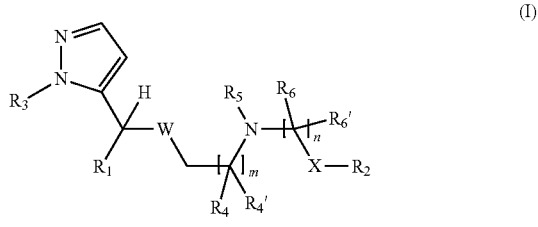

(I)

which process comprises:

a) alkylating a compound of Formula (XIII)

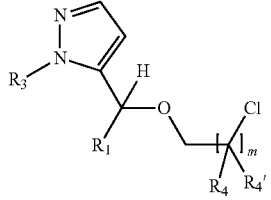
(XIII)

with a compound of Formula (XIV)

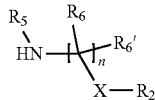
(XIV)

Or b) reacting a carbinol of Formula (IIa)

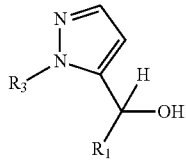
(IIa)

with a compound of general Formula (XV)

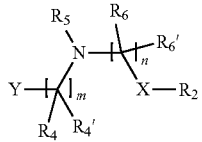
(XV)

Or c) reacting a compound of general Formula (V)

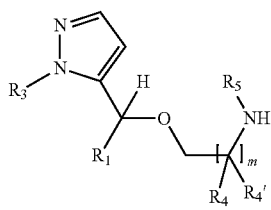
(V)

with a suitable reagent of Formula (VIa) or (VIb)

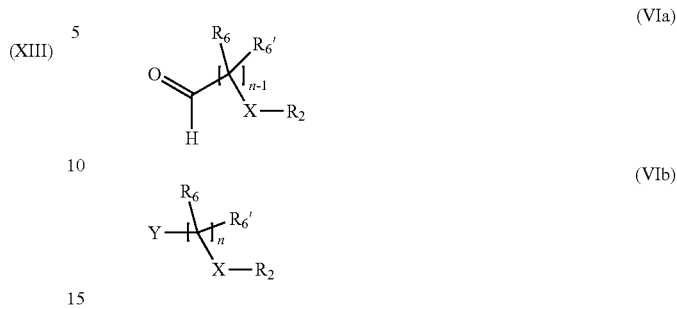
(VIa)

(VIb)

Or d) the reduction of a compound of Formula (VIII)

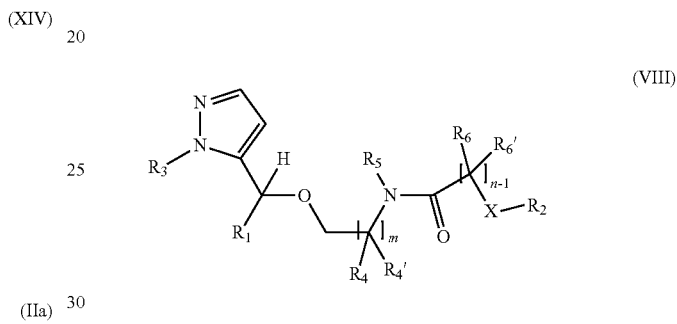
(VIII)

wherein m, n, $R_1$, $R_2$, $R_3$, $R_4$, $R_{4'}$, $R_5$, $R_6$, $R_{6'}$ and X have the meanings as defined in claim 1 for the compound of formula (I), W is —O—, and Y is a hydroxyl group or a leaving group, including chloro, bromo, mesylate and tosylate.

8. A process for the preparation of the compound of formula (I) according to claim 1 employing a compound of Formula (IIa), (III), (IV), (V), (VIa), (VIb), (VII), (VIII), (IX), (X), (XI), (XII), (XIII), (XIV) or (XV)

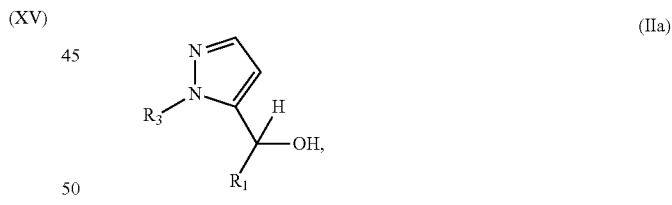
(IIa)

(III)

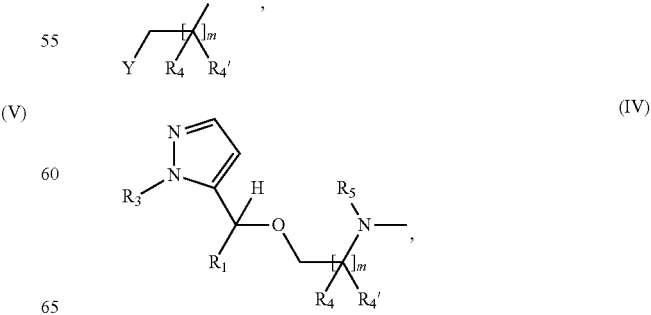
(IV)

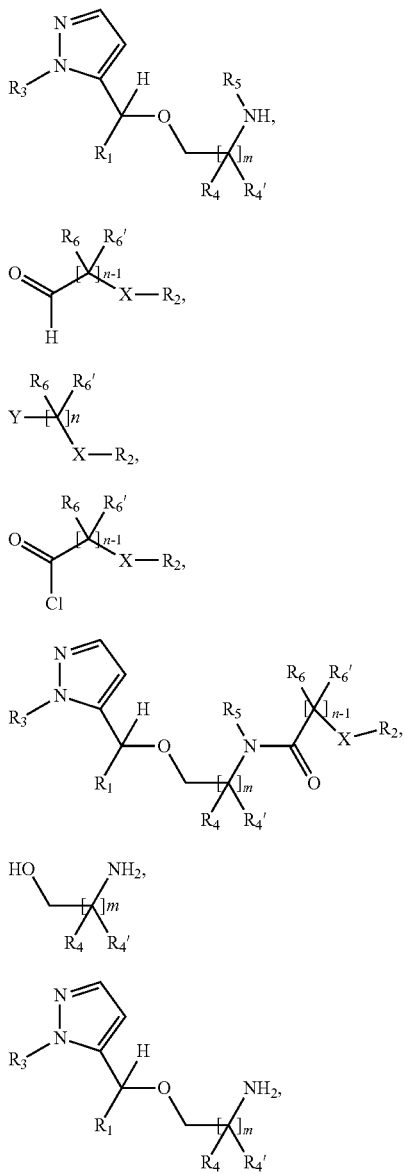

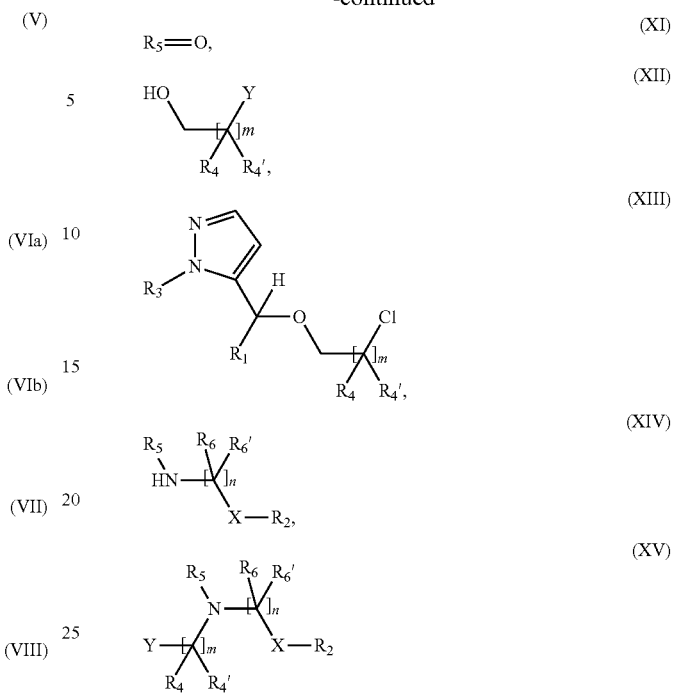

wherein m, n, $R_2$, $R_4$, $R_{4'}$, $R_5$, $R_6$, $R_{6'}$ and X have the meanings as defined in claim 1 for the compound of formula (I), and wherein Y is a hydroxyl group or a leaving group, including chloro, bromo, mesylate and tosylate.

9. A pharmaceutical composition comprising the compound according to claim 1, or a pharmaceutically acceptable salt thereof, and a pharmaceutically acceptable carrier, adjuvant or vehicle.

10. A method of treating pain in a subject in need thereof, comprising administration of an effective amount of the compound according to claim 1.

11. The method according to claim 10, wherein the pain is selected from medium to severe pain, visceral pain, chronic pain, cancer pain, migraine, inflammatory pain, acute pain, neuropathic pain, allodynia, and hyperalgesia.

* * * * *

UNITED STATES PATENT AND TRADEMARK OFFICE
CERTIFICATE OF CORRECTION

PATENT NO. : 10,071,968 B2
APPLICATION NO. : 15/531810
DATED : September 11, 2018
INVENTOR(S) : Antoni Torrens-Jover et al.

Page 1 of 1

It is certified that error appears in the above-identified patent and that said Letters Patent is hereby corrected as shown below:

In the Claims

Column 107, Line 60: "-2-(1-methyl(1-methyl-1H" should read -- -2-((1-methyl-1H --.

Column 107, between Line 63 and Line 64: Add as a new line -- N-(3-methoxybenzyl)-N-methyl-2-((1-methyl-1H-pyrazol-5-yl)(phenyl)methoxy)ethanamine, --.

Column 107, Line 64: "(N-(3-" should read -- N-(3- --.

Column 108, delete Line 1 and Line 2.

Signed and Sealed this
Sixteenth Day of October, 2018

Andrei Iancu
*Director of the United States Patent and Trademark Office*